(12) United States Patent
Fukushima et al.

(10) Patent No.: US 11,732,191 B2
(45) Date of Patent: *Aug. 22, 2023

(54) COMPOUND, POLYMERIZABLE COMPOSITION, CURED PRODUCT, OPTICAL FILM, POLARIZING PLATE, AND IMAGE DISPLAY DEVICE

(71) Applicant: FUJIFILM Corporation, Tokyo (JP)

(72) Inventors: Yuki Fukushima, Kanagawa (JP);
Hiroshi Inada, Kanagawa (JP);
Toshikazu Sumi, Kanagawa (JP);
Shunya Katoh, Kanagawa (JP);
Mitsuyoshi Ichihashi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/486,096

(22) Filed: Sep. 27, 2021

(65) Prior Publication Data

US 2022/0010209 A1 Jan. 13, 2022

Related U.S. Application Data

(63) Continuation of application No. PCT/JP2020/013119, filed on Mar. 24, 2020.

(30) Foreign Application Priority Data

Mar. 29, 2019 (JP) .................................. 2019-068589
Dec. 4, 2019 (JP) .................................. 2019-219424

(51) Int. Cl.
| | | |
|---|---|---|
| G02F 1/1333 | (2006.01) | |
| C09K 19/30 | (2006.01) | |
| C09K 19/34 | (2006.01) | |
| G02B 5/30 | (2006.01) | |
| C09K 19/04 | (2006.01) | |

(52) U.S. Cl.
CPC ...... *C09K 19/3068* (2013.01); *C09K 19/3497* (2013.01); *G02B 5/3016* (2013.01); *C09K 2019/0448* (2013.01); *C09K 2019/3075* (2013.01); *C09K 2219/03* (2013.01)

(58) Field of Classification Search
CPC ............ C09K 19/3068; C09K 19/3497; C09K 19/3491; C09K 19/3003; C09K 19/3001; C09K 2019/0448; C09K 2019/0444; C09K 2019/3075; C09K 2219/03; G02B 5/3016; G02F 1/1333
See application file for complete search history.

(56) References Cited

U.S. PATENT DOCUMENTS

| | | | | |
|---|---|---|---|---|
| 8,565,058 B2 * | 10/2013 | Shiono | .............. | G02F 1/133788 428/1.2 |
| 10,048,416 B2 * | 8/2018 | Muramatsu | ........ | C09K 19/3491 |
| 2013/0163399 A1 | 6/2013 | Shiono et al. | | |
| 2015/0079380 A1 | 3/2015 | Muramatsu et al. | | |
| 2022/0010209 A1* | 1/2022 | Fukushima | ........ | C09K 19/3068 |
| 2022/0213384 A1* | 7/2022 | Katoh | ................ | C09K 19/3491 |

FOREIGN PATENT DOCUMENTS

| | | |
|---|---|---|
| JP | 2013-152439 A | 8/2013 |
| JP | 2013-216591 A | 10/2013 |
| JP | 2015-200861 A | 11/2015 |
| JP | 2017-226616 A | 12/2017 |

OTHER PUBLICATIONS

International Search Report issued in PCT/JP2020/013119 dated Jun. 16, 2020.
Written Opinion issued in PCT/JP2020/013119 dated Jun. 16, 2020.
International Preliminary Report on Patentability completed by WIPO dated Sep. 28, 2021 in connection with International Patent Application No. PCT/JP2020/013119.
CAS Registry No. 566947-31-7, Database Registry, (online), Aug. 15, 2003, (retrieved on May 29, 2020), Retrieved from: STN, Entire Text.
Office Action, issued by the Japanese Patent Office dated Oct. 25, 2022, in connection with Japanese Patent Application No. 2021-511510.

* cited by examiner

*Primary Examiner* — Geraldina Visconti
(74) *Attorney, Agent, or Firm* — Edwards Neils LLC; Jean C. Edwards, Esq.

(57) ABSTRACT

Provided is a compound which is capable of reducing a tilt angle of a liquid crystal molecule, and a polymerizable composition, a cured product, an optical film, a polarizing plate, and an image display device, each using the compound. The compound is represented, for example, by Formula (I), P-Sp-Z-$G^1$-($X^1$-$Cy^1$)n-($X^2$-$A^1$)m-$X^3$-$A^2$.

25 Claims, 1 Drawing Sheet

COMPOUND, POLYMERIZABLE COMPOSITION, CURED PRODUCT, OPTICAL FILM, POLARIZING PLATE, AND IMAGE DISPLAY DEVICE

CROSS-REFERENCE TO RELATED APPLICATIONS

This application is a Continuation of PCT International Application No. PCT/JP2020/013119 filed on Mar. 24, 2020, which was published under PCT Article 21(2) in Japanese, and which claims priority under 35 U.S.C. § 119(a) to Japanese Patent Application No. 2019-068589 filed on Mar. 29, 2019 and Japanese Patent Application No. 2019-219424 filed on Dec. 4, 2019. The above is applications are hereby expressly incorporated by reference, in their entirety, into the present application.

BACKGROUND OF THE INVENTION

1. Field of the Invention

The present invention relates to a compound, a polymerizable composition, a cured product, an optical film, a polarizing plate, and an image display device.

2. Description of the Related Art

Optical films such as an optical compensation sheet and a phase difference film are used in various image display devices in order to eliminate image coloration or expand a viewing angle.

A stretched birefringent film has been used as the optical film, but in recent years, it has been proposed to use an optical film having an optically anisotropic layer consisting of a liquid crystalline compound instead of the stretched birefringent film.

As such an optically anisotropic layer, for example, "an optically anisotropic layer in which a polymerizable composition including one or more polymerizable rod-shaped liquid crystal compounds exhibiting a smectic phase is immobilized in a state of exhibiting a smectic phase, and in which an inclination with respect to a surface of the optically anisotropic layer in a direction in which a refractive index of the optically anisotropic layer is maximized is 10° or less" is described in JP2015-200861A" ([Claim 1]).

SUMMARY OF THE INVENTION

The present inventors have examined the optically anisotropic layer described in Patent Document 1, and have thus found that there is room for making it possible to reduce an angle (hereinafter abbreviated as a "tilt angle") between a director direction of a liquid crystal molecule and a layer plane of the optically anisotropic layer by selecting a compound to be blended together with a polymerizable liquid crystal compound.

Therefore, an object of the present invention is to provide a compound which is capable of reducing a tilt angle of a liquid crystal molecule; and a polymerizable composition, a cured product, an optical film, a polarizing plate, and an image display device, each using the compound.

The present inventors have conducted intensive studies to accomplish the object, and as a result, they have found that a tilt angle of a liquid crystal molecule can be reduced by using a compound having a predetermined structure, thereby completing the present invention.

That is, the present inventors have found that the object can be accomplished by the following configurations.

[1] A compound represented by Formula (I).

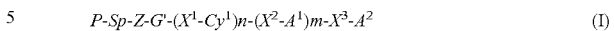

$$P\text{-}Sp\text{-}Z\text{-}G^1\text{-}(X^1\text{-}Cy^1)n\text{-}(X^2\text{-}A^1)m\text{-}X^3\text{-}A^2 \quad \text{(I)}$$

Here, in Formula (I),

Sp represents a single bond, a linear or branched alkylene group having 1 to 12 carbon atoms, or a divalent linking group obtained by substituting one or more of —$CH_2$—'s constituting the linear or branched alkylene group having 1 to 12 carbon atoms with —O—, —S—, —NH—, —N(Q)-, —CO—, —COO—, —OCO—, —CO—NH—, or —NH—CO—, and Q represents a substituent.

Z represents a single bond, —O—, —S—, —NH—, —N(Q)-, —CO—, —COO—, —OCO—, —CO—NH—, or —NH—CO—, and Q represents a substituent.

$X^1$, $X^2$, and $X^3$ each independently represent a single bond, —COO—, —OCO—, —CO—NH—, or —NH—CO—.

$G^1$ represents an aromatic ring which may have a substituent or a 1,4-cyclohexylene group which may have a substituent.

$Cy^1$ represents a 1,4-cyclohexylene group which may have a substituent.

$A^1$ represents an aromatic ring which may have a substituent.

$A^2$ represents an aromatic ring which may have a substituent R, or a cyclohexane ring, the substituent R represents a linear or branched alkoxy group having 1 to 11 carbon atoms, a linear or branched alkyl group having 1 to 12 carbon atoms, or -Z-Sp-P, and Z and Sp are each the same as described above. It should be noted that in a case where $A^2$ is a 6-membered aromatic ring, $A^2$ has no substituent R at the para position with respect to a bonding position with $X^3$. In addition, M a case where the substituent R is -Z-Sp-P, two Z's, two Sp's, and two P's which are present in the formula may be the same as or different from each other.

n represents 0 or 1, m represents an integer of 0 to 2, and n in represents an integer of 1 to 3. In a case where m is 2, both of two $X^2$'s and two $A^1$'s which are present in the formula may be the same as or different from each other.

P represents a polymerizable group. It should be noted that in a case where $A^2$ is the aromatic ring having -Z-Sp-P as the substituent R, one of the two P's which are present in the formula represents a polymerizable group and the other represents a hydrogen atom or a polymerizable group.

It should be noted that in a case where $G^1$ is the aromatic ring which may have a substituent, n is 0, and in is 1, $X^3$ represents —COO—, —OCO—, —CO—NH—, or —NH—CO—.

In addition, in a case where $G^1$ is the aromatic ring which may have a substituent, n is 1, m is 0, and $A^2$ is the aromatic ring which may have the substituent R, Z represents a single bond, —S—, —N(Q)-, —CO—, —COO—, —OCO—, —CO—NH—, or —NH—CO—, and Q represents a substituent. It should be noted that in a case where Z is the single bond, an atom adjacent to $G^1$ among the divalent linking groups constituting Sp is not an oxygen atom.

[2] The compound as described in [1],
in which a total of n and m in Formula (I) is 1.
[3] The compound as described in [1] or [2],
in which Sp in Formula (1) is a linear or branched alkylene group having 1 to 3 carbon atoms.
[4] The compound as described in any one of [1] to [3],
in which $A^2$ in Formula (1) is the aromatic ring which may have the substituent R.

[5] The compound as described in any one of [1] to [4], in which $A^2$ in Formula (1) is a 6-membered aromatic ring having the substituent R at an Rothko position or meta position with respect to a bonding position with $X^3$.
[6] The compound as described in any one of [1] to [5], in which the substituent R is -Z-Sp-P.
[7] The compound as described in any one of [1] to [3], in which $A^2$ in Formula (1) is an unsubstituted 6-membered aromatic ring.
[8] The compound as described in any one of [1] to [7], in which $A^2$ in Formula (1) is a benzene ring which may have the substituent R.
[9] The compound as described in any one of [1] to [8], in which m in Formula (1) is 0.
[10] The compound as described in any one of [1] to [9], in which n in Formula (1) is 1.
[11] The compound as described in any one of [1] to [8], in which n in Formula (1) is 0.
[12] The compound as described in any one of [1] to [11], in which P in Formula (1) is a polymerizable group represented by any of Formulae (P-1) to (P-9).

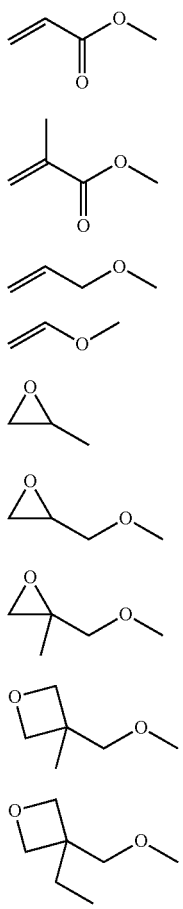

[13] The compound as described in any one of [1] to [12], in which $G^1$ in Formula (1) is a 1,4-cyclohexylene group which may have a substituent.
[14] The compound as described in any one of [1] to [12], in which $G^1$ in Formula (1) is an aromatic ring which may have a substituent.
[15] A polymerizable composition containing the compound as described in any one of [1] to [14].

[16] The polymerizable composition as described in [15], comprising a polymerizable liquid crystal compound different from the compound.
[17] The polymerizable composition as described in [16], in which the compound and the polymerizable liquid crystal compound have polymerizable groups that are different from each other.
[18] The polymerizable composition as described in any one of [15] to [17], comprising a polymerization initiator.
[19] A cured product obtained by curing the polymerizable composition as described in any one of [15] to [18].
[20] An optical film comprising the cured product as described in [19].
[21] A polarizing plate comprising:
the optical film as described in [20]; and
a polarizer.
[22] An image display device comprising the optical film as described in [20] or the polarizing plate as described in [21].

According to the present invention, it is possible to provide a compound which is capable of reducing a tilt angle of a liquid crystal molecule; and a polymerizable composition, a cured product, an optical film, a polarizing plate, and an image display device, each using the compound.

DESCRIPTION OF THE PREFERRED EMBODIMENTS

Figure 1A:
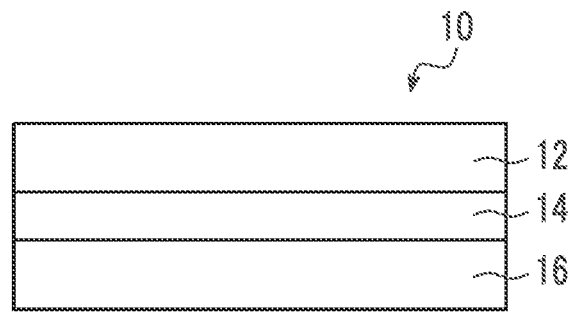
FIG. 1A is a schematic cross-sectional view showing an example of the optical film of the present invention.

Hereinafter, the present invention will be described in detail.
Descriptions on the configuration requirements which will be described later—are made based on representative embodiments of the present invention in some cases, but it should not be construed that the present invention is limited to such embodiments.
Furthermore, in the present specification, a numerical value range expressed using "to" means a range that includes the preceding and succeeding numerical values of "to" as the lower limit value and the upper limit value, respectively.
In addition, in the present specification, only one kind of the substance corresponding to each component may be used alone or two or more kinds thereof may also be used in combination, for each component. Here, in a case where the two or more substances are used in combination for each component, the content of the component refers to a total content of the substances used in combination unless otherwise specified.
[Compound]
The compound of an embodiment of the present invention is a compound represented by Formula (I) (hereinafter also simply referred to as a "compound (I)").

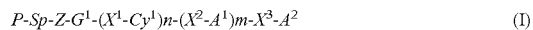

In the present invention, the tilt angle of a liquid crystal molecule care be reduced by using the compound (I) as mentioned above.

A reason thereof is not specifically clear, but is presumed to be as follows by the present inventors.

First, from the viewpoint of fixing an alignment state, the polymerizable liquid crystal compound is generally polymerized after the alignment but it is considered that curing shrinkage accompanying this polymerization causes distortion in the liquid crystal molecule, resulting in a reduction in the tilt angle.

Therefore, in the present invention, it is considered that the compound (I) enters a gap and a space between layers of the polymerizable liquid crystal compound and participates in the polymerization reaction after the alignment, whereby the distortion of a liquid crystal molecule observed during the polymerization of the liquid crystal compound alone can be suppressed, and therefore, the tilt angle of the liquid crystal molecule could be reduced.

Hereinafter, the configuration of Formula (I) will be described in detail with respect to the compound of the embodiment of the present invention.

The compound of the embodiment of the present invention is a compound represented by Formula (I), as mentioned above.

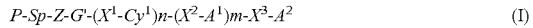

$$P\text{-}Sp\text{-}Z\text{-}G'\text{-}(X^1\text{-}Cy^1)n\text{-}(X^2\text{-}A^1)m\text{-}X^3\text{-}A^2 \quad (I)$$

In Formula (I), Sp represents a single bond, a linear or branched alkylene group having 1 to 12 carbon atoms, or a divalent linking group obtained by substituting one or more of —$CH_2$—'s constituting the linear or branched alkylene group having 1 to 12 carbon atoms with —O—, —S—, —NH—, —N(Q)-, —CO—, —COO—, —OCO—, —CO—NH—, or —NH—CO—, and Q represents a substituent.

Furthermore, in Formula (I), Z represents a single bond, —O—, —S—, —NH—, —N(Q)-, —CO—, —COO—, —OCO—, —CO—NH—, or —NH—CO—, and Q represents a substituent.

In addition, in Formula (I), $X^1$, $X^2$, and $X^3$ each independently represent a single bond, —COO—, —OCO—, —CO—NH—, or —NH—CO—.

Moreover, in Formula (I), $G^1$ represents an aromatic ring which may have a substituent or a 1,4-cyclohexylene group which may have a substituent.

In addition, in Formula (I), $Cy^1$ represents a 1,4-cyclohexylene group which may have a substituent.

Furthermore, in Formula (I), $A^1$ represents an aromatic ring which may have a substituent.

In addition, in Formula (I), $A^2$ represents an aromatic ring which may have a substituent R, or a cyclohexane ring, the substituent R represents a linear or branched alkoxy group having 1 to 11 carbon atoms, a linear or branched alkyl group having 1 to 12 carbon atoms, or -Z-Sp-P, and Z and Sp are each the same as described above. It should be noted that in a case where $A^2$ is a 6-membered aromatic ring, $A^2$ has no substituent R at the para position with respect to a bonding position with $X^3$. In addition, in a case where the substituent R is -Z-Sp-P, two Z's, two Sp's, and two P's which are present in the formula may be the same as or different from each other.

Furthermore, in Formula (1), n represents 0 or 1, m represents an integer of 0 to 2, and n×m represents an integer of 1 to 3. In a case where m is 2, both of two $X^2$'s and two $A^1$'s which are present in the formula may be the same as or different from each other.

Further, in Formula (I), P represents a polymerizable group. It should be noted that in a case where $A^2$ is the aromatic ring having -Z-Sp-P as the substituent R, one of the two P's which are present in the formula represents a polymerizable group and the other represents a hydrogen atom or a polymerizable group.

It should be noted that in a case where $G^1$ is the aromatic ring which may have a substituent, n is 0, and m is 1 in Formula (I), $X^3$ represents —COO—, —OCO—, —CO—NH—, or —NH—CO—.

In addition, in a case where $G^1$ is the aromatic ring which may have a substituent, n is 1, m is 0, and $A^2$ is the aromatic ring which may have the substituent R in Formula (I), Z represents a single bond, —S—, —NH—, —N(Q)-, —CO—, —COO—, —OCO—, —CO—NH—, or —NH—CO—, and Q represents a substituent. It should be noted that in a case where Z is the single bond, an atom adjacent to $G^1$ among the divalent linking groups constituting Sp is not an oxygen atom.

Suitable examples of the linear or branched alkylene group having 1 to 12 carbon atoms shown in one aspect of Sp in Formula (I) include a ethylene group, an ethylene group, a propylene group, a furylene group, a phenylene group, a xylene group, a methylhexylene group, and a heptylene group.

Incidentally, Sp may be a divalent linking group obtained by substituting one or more of —$CH_2$—'s constituting the linear or branched alkylene group having 1 to 12 carbon atoms with —O—, —S—, —NH—, —N(Q)-, —CO—, —COO—, —OCO—, —CO—NH—, or —NH—CO—, as mentioned above, and examples of the substituent represented by Q include the same ones as the substituents which may be contained in $G^1$ which will be described later.

In the present invention, it is preferable that Sp in Formula (I) is a linear or branched alkylene group having 1 to 3 carbon atoms for a reason that the tilt angle of the liquid crystal molecule can be reduced.

In Formula (I), Z represents a single bond, —O—, —S—, —NH—, —N(Q)-, —CO—, —COO—, —OCO—, —CO—NH—, or —NH—CO—, and Q represents a substituent. Incidentally, examples of the substituent represented by Q include the same substituents which may be contained in $G^1$ which will be described later.

Among these, the substituent is preferably the single bond, —CO—, —COO—, —OCO—, —CO—NH—, or —NH—CO—, for a reason of easy synthesis. In particular, in a case where $G^1$ which will be described later is the aromatic ring which may have a substituent, the substituent is preferably the single bond.

In Formula (I), $X^1$, $X^2$, and $X^3$ each independently represents a single bond, —COO—, —OCO—, —CO—NH—, or —NH—CO.

Among these, with respect to $X^1$, in a case where n in Formula (I) is 1 and $G^1$ which will be described later is the aromatic ring which may have a substituent, it is preferable that $X^1$ is the single bond or, alternatively, is —COO— or —OCO—.

In addition, in a case where m in Formula (I) is 1 or 2, it is preferable that $X^2$ is —COO— or —OCO—.

Furthermore, with respect to $X^3$, in a case where m in Formula (I) is 0, it is preferable that $X^3$ is —COO— or —OCO— regardless of the type of $G^1$ which will be described later, and in a case where in is 1 or 2, it is preferable that $X^3$ is the single bond.

In Formula (I), examples of the aromatic ring shown in one aspect of $G^1$ include aromatic hydrocarbon rings such as a benzene ring, a naphthalene ring, an anthracene ring, and a phenanthroline ring; and aromatic heterocycles such as a furan ring, a thiophene ring, a pyrrole ring, an oxazole ring, an isoxazole ring, an oxadiazole ring, a thiazole ring, an isothiazole ring, a thiadiazole ring, an imidazole ring, a pyrazole ring, a triazole ring, a furazan ring, a tetrazole ring, a pyridine ring, a pyridazine ring, a pyrimidine ring, a pyrazine ring, a triazole ring, a tetrazine ring, and a benzothiazole ring. Among these, the benzene ring (for example, a 1,4-phenyl group) is preferable.

In addition, with respect to $G^1$, examples of the substituent which may be contained in the aromatic ring or the 1,4-cyclohexylene group include an alkyl group, an alkoxy group, and a halogen atom.

As the alkyl group, for example, a linear, branched, or cyclic alkyl group having 1 to 18 carbon atoms is preferable, an alkyl group having 1 to 8 carbon atoms (for example, a methyl group, an ethyl group, a propyl group, an isopropyl group, an n-butyl group, an isobutyl group, a sec-butyl group, a t-butyl group, and a cyclohexyl group) is more preferable, an alkyl group having 1 to 4 carbon atoms is still more preferable, and the methyl group or the ethyl group is particularly preferable.

As the alkoxy group, for example, an alkoxy group having 1 to 18 carbon atoms is preferable, an alkoxy group having 1 to 8 carbon atoms (for example, a methoxy group, an ethoxy group, an n-butoxy group, and a methoxy ethoxy group) is more preferable, an alkoxy group having 1 to 4 carbon atoms is still more preferable, and the methoxy group or the ethoxy group is particularly preferable.

Examples of the halogen atom include a fluorine atom, a chlorine atom, a bromine atom, and an iodine atom, and among these, the fluorine atom or the chlorine atom is preferable.

In the present invention, it is preferable that $G^1$ is the 1,4-cyclohexylene group which may have a substituent for a reason that the tilt angle of the liquid crystal molecule can be reduced.

In addition, it is preferable that $G^1$ is the aromatic ring which may have a substituent for a reason that the tilt angle of the liquid crystal molecule can be reduced.

In Formula (1), $Cy^1$ represents a 1,4-cyclohexylene group which may have a substituent. Further, examples of the substituent include the same ones as the substituents which may be contained in $G^1$ as described above.

In Formula (I), examples of the aromatic ring represented by $A^1$ include the same ones of the aromatic ring shown in one aspect of $G^1$ described above.

In addition with respect to $A^1$, examples of the substituent which may be contained in the aromatic ring include the same ones as the substituent which may be contained in $G^1$ as described above.

In Formula (I), $A^2$ represents an aromatic ring which may have a substituent R, or a cyclohexane ring but is preferably the aromatic ring which may have the substituent R, and more preferably a benzene ring which may have the substituent R for a reason that the tilt angle of the liquid crystal molecule can be reduced.

Here, examples of the aromatic ring shown in one aspect of $A^2$ include the same ones as the aromatic ring shown in one aspect of $A^1$ described above. Further, in a case where $A^2$ is a 6-membered aromatic ring, $A^2$ has no substituent R at the para position with respect to a bonding position with $X^3$.

In addition, the substituent R which may be contained in the aromatic ring shown in one aspect of $A^2$ represents a linear or branched alkoxy group having 1 to 11 carbon atoms, a linear or branched alkyl group having 1 to 12 carbon atoms, or -Z-Sp-P, as described above. Further, Z and Sp are each the same as those described above, and P will be described later.

Here, specific examples of the linear or branched alkoxy group having 1 to 11 carbon atoms include a methoxy group, an ethoxy group, a propoxy group, a butoxy group, a pentyloxy group, a hexyloxy group, a heptyloxy group, an octyloxy group, and a decyloxy group.

In addition, specific examples of the linear or branched alkyl group having 1 to 12 carbon atoms include a methyl group, an ethyl group, a propyl group, an isopropyl group, an n-butyl group, an isobutyl group, a sec-butyl group, a t-butyl group, and a cyclohexyl group.

Among these substituents R, -Z-Sp-P is preferable for a reason that the durability of the cured product of the embodiment of the present invention, which will be described later, is improved. Further, in a case where the substituent R is -Z-Sp-P, two Z's, two Sp's, and two P's which are present in Formula (I) may be the same as or different from each other.

In the present invention, it is preferable that $A^2$ is a 6-membered aromatic ring having the substituent R at the ortho position or meta position with respect to a bonding position with $X^3$.

In addition, it is preferable that $A^2$ is an unsubstituted 6-membered aromatic ring.

In Formula (I), n represents 0 or 1, m represents an integer of 0 to 2, and n+m represents an integer of 1 to 3. Further, in a case where m is 2, both of two $X^2$'s and two $A^1$'s which are present in the formula may be the same as or different from each other.

In the present invention, the total of n and m is preferably 1 or 2, and more preferably 1 for a reason that the tilt angle of the liquid crystal molecule can be reduced.

Furthermore, m is preferably 0 or 1, and more preferably 0 for the reason that the tilt angle of the liquid crystal molecule can be reduced.

In addition, n is preferably 0 or 1 for a reason that the tilt angle of the liquid crystal molecule can be reduced.

In Formula (1), P represents a polymerizable group. It should be noted that in a case where $A^2$ is the aromatic ring having -Z-Sp-P as the substituent R, one of the two P's which are present in the formula represents a polymerizable group and the other represents a hydrogen atom or a polymerizable group.

Here, as the polymerizable group, a polymerizable group that is radically polymerizable or cationically polymerizable is preferable.

A generally known radically polymerizable group can be used as the radically polymerizable group, and suitable examples thereof include an acryloyloxy group and a methacryloyloxy group. In this case, it is known that the acryloyloxy group generally has a high polymerization rate, and from the viewpoint of improvement of productivity, the acryloyloxy group is preferable but the methacryloyloxy group can also be used in the same manner as the polymerizable group.

A generally known cationically polymerizable group can be used as the canonically polymerizable group, and specific examples thereof include an alicyclic ether group, a cyclic acetal group, a cyclic lactone group, a cyclic thioether group, a spiroorthoester group, and a vinyloxy group. Among those, the alicyclic ether group or the vinyloxy group is suitable, and an epoxy group, an oxetanyl group, or the vinyloxy group is particularly preferable.

In the present invention, the polymerizable group is preferably a polymerizable group represented by any of Formulae (P-1) to (P-9).

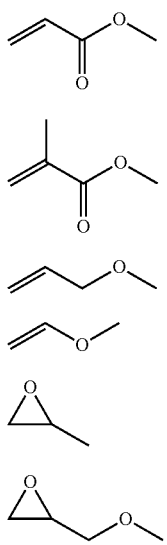
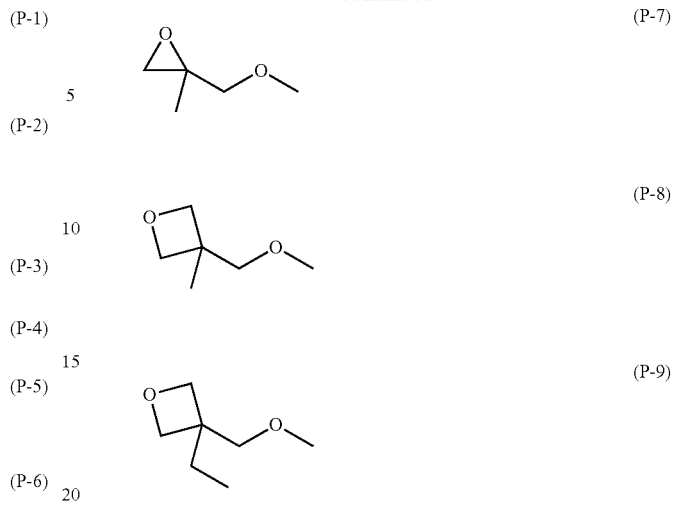
Suitable specific examples of the compound (I) include the compounds shown below
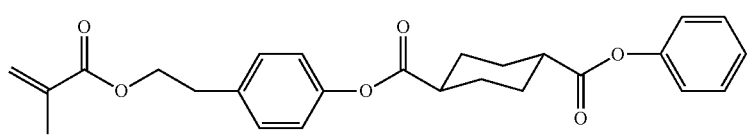
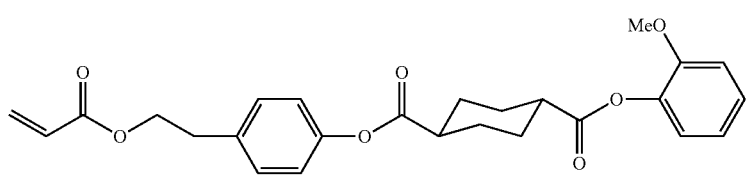
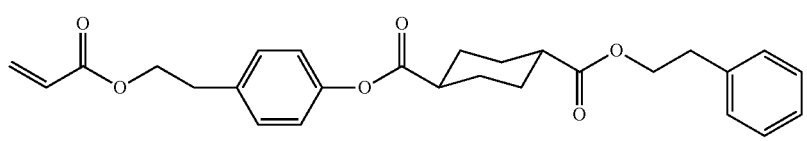
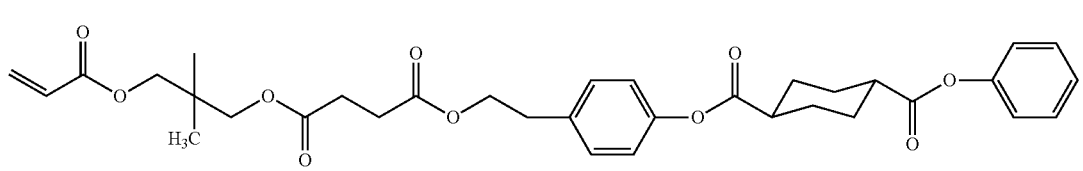
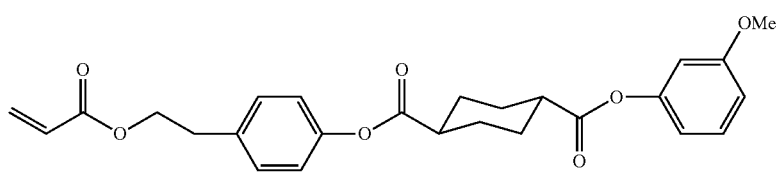
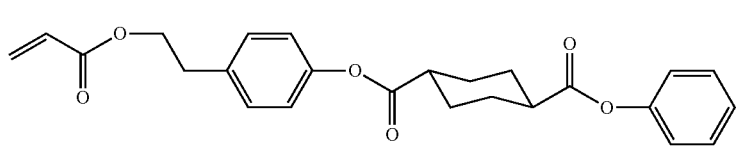

-continued
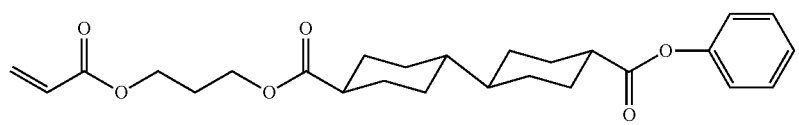
D-1
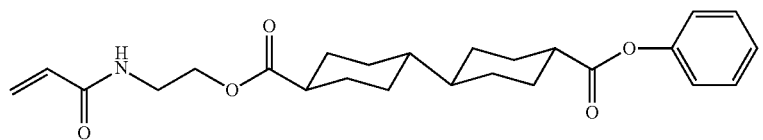
D-2
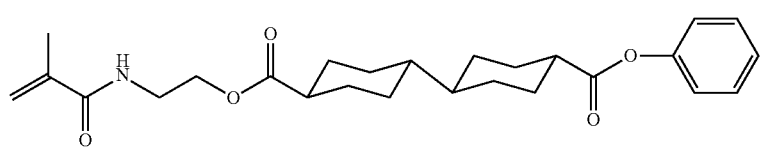
D-3
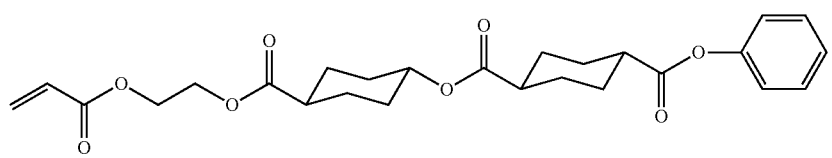
D-4
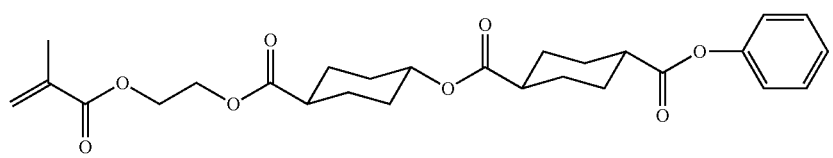
D-5
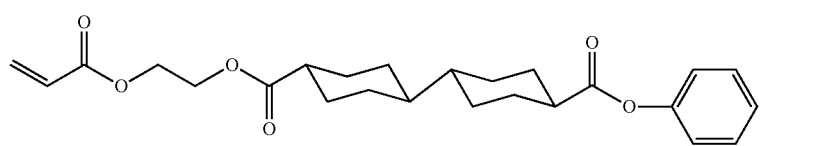
D-6
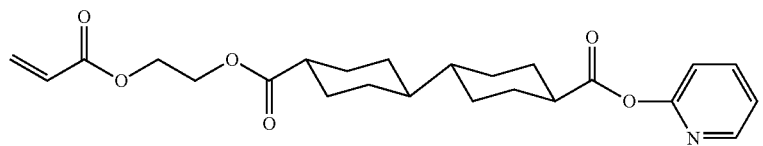
D-7
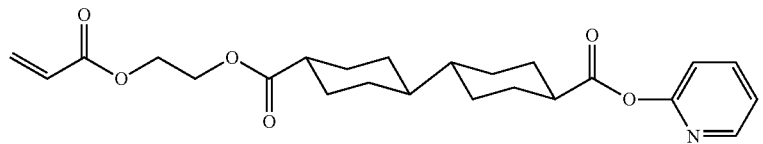
D-8
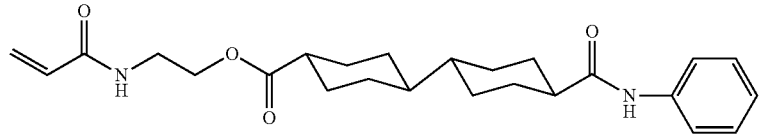
D-9
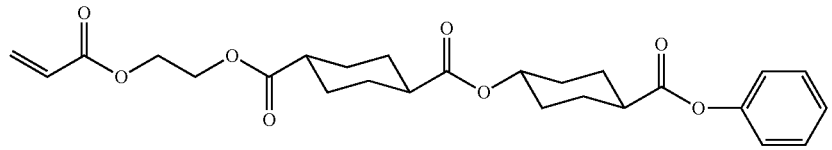
D-10

-continued
D-11
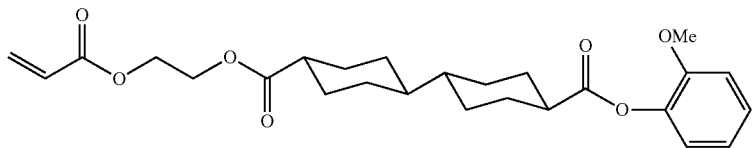
D-12
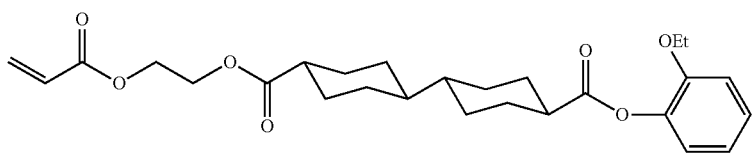
D-13
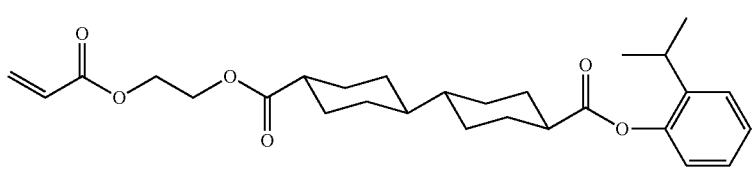
D-14
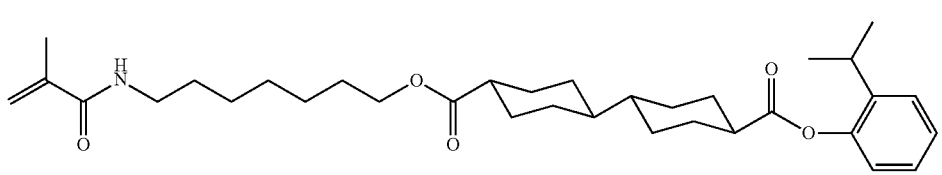
D-15
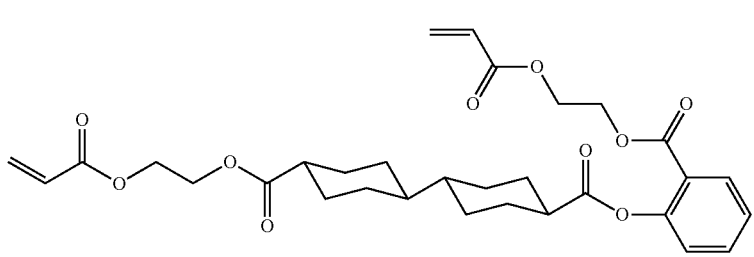
D-16
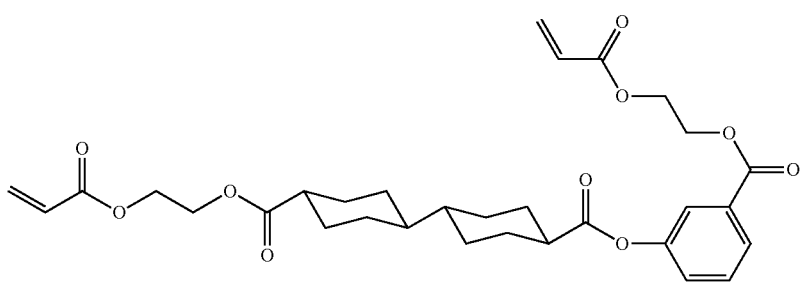
D-17
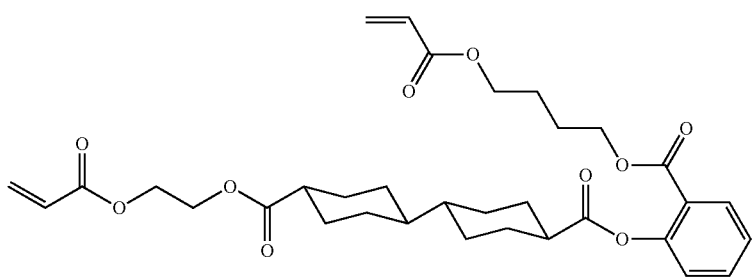

D-18
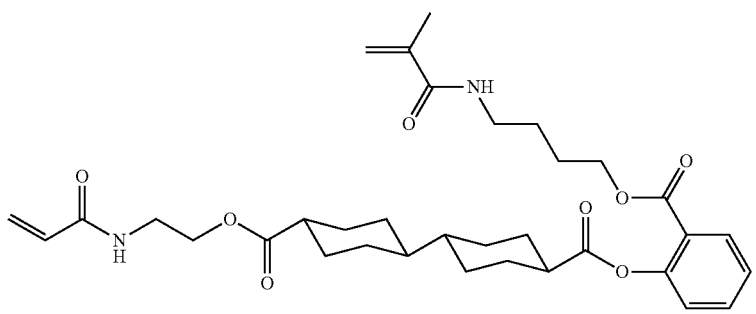
D-19
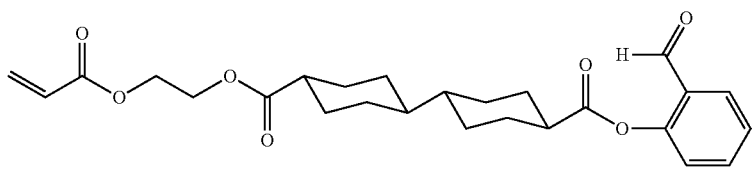
D-20
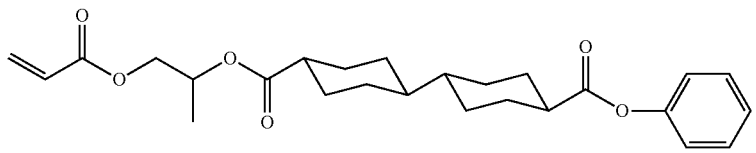
D-21
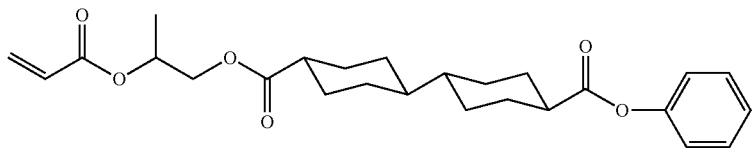
D-22
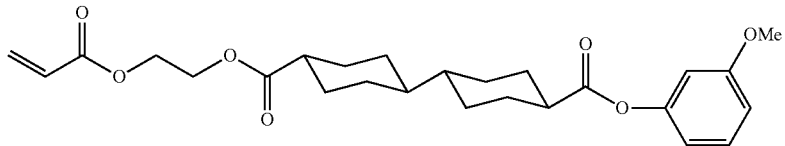
D-23
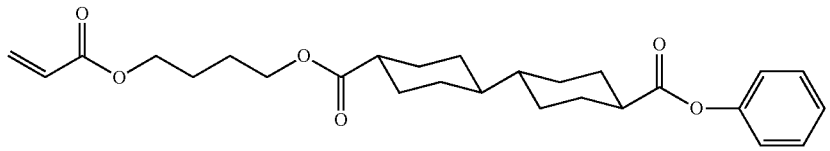
D-24
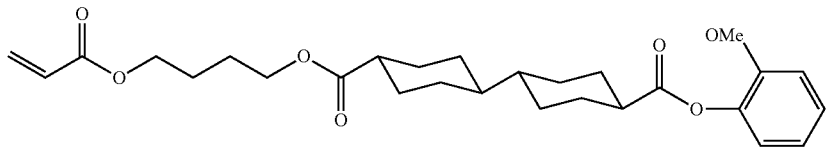
D-25
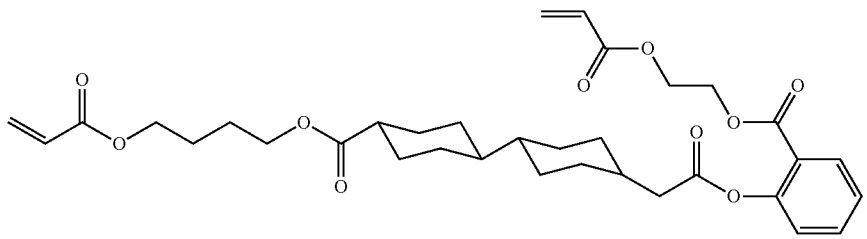

-continued
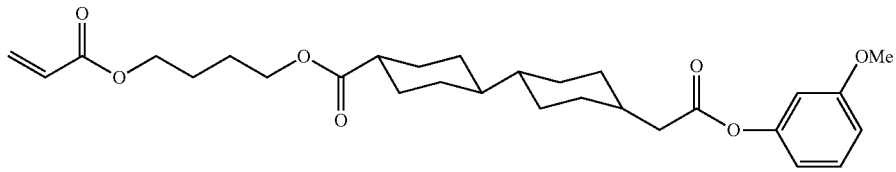
D-26
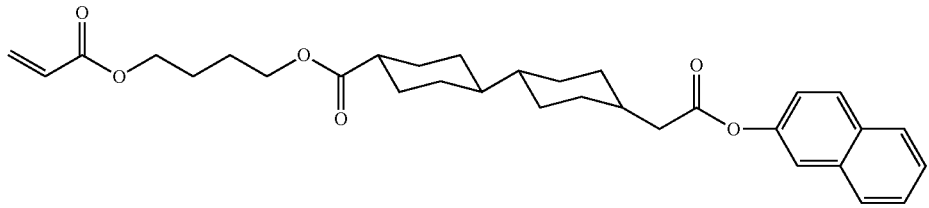
D-27
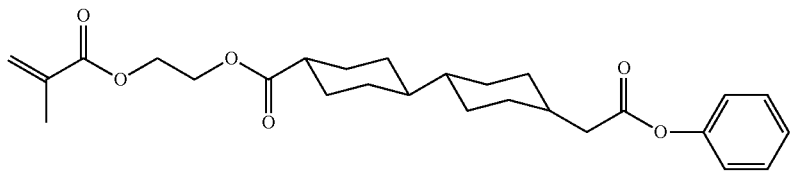
D-28
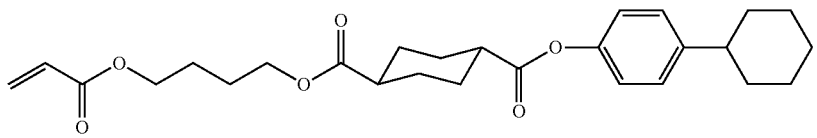
P-1
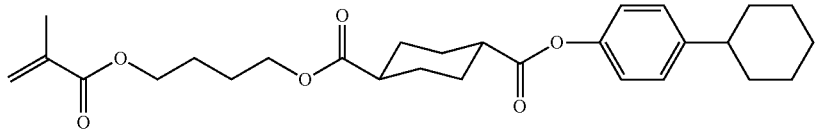
P-2
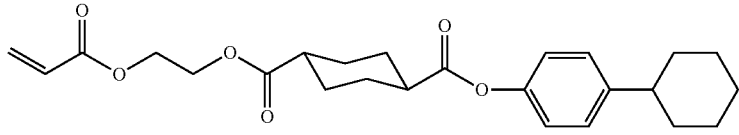
P-3
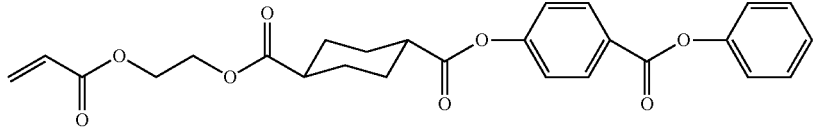
O-1
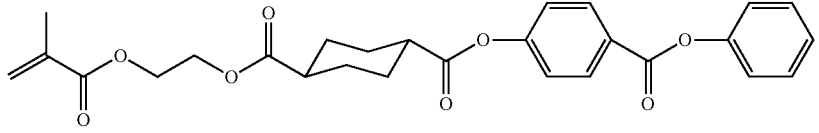
O-2
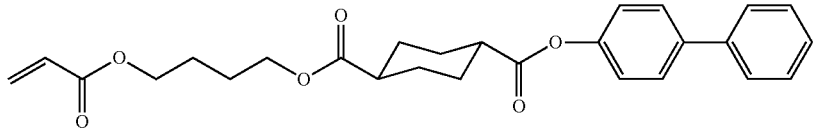
O-3
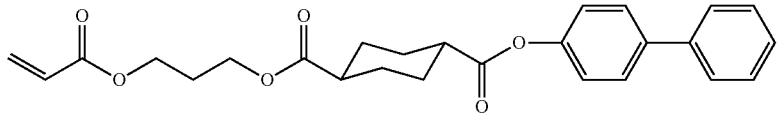
O-4

-continued
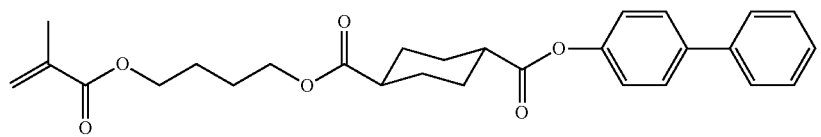
O-5
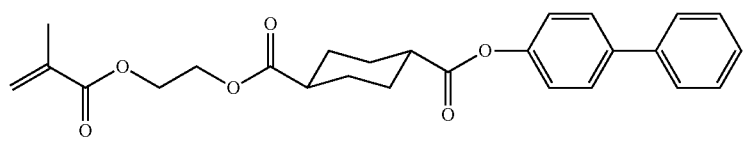
O-6
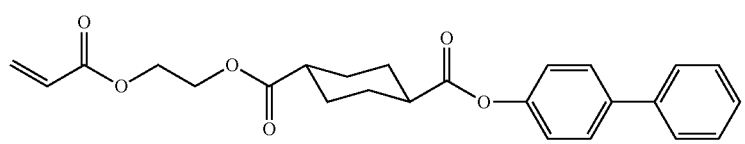
O-7
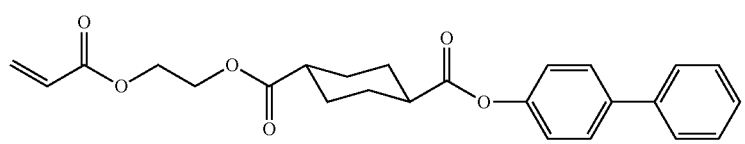
O-8
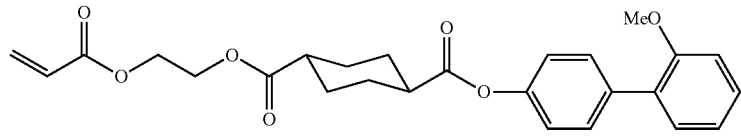
O-9
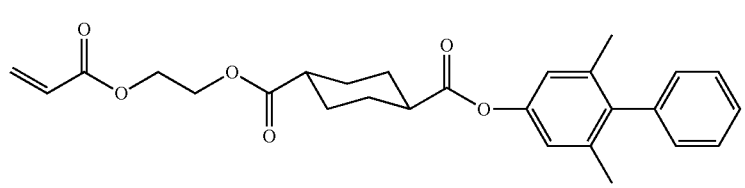
O-10
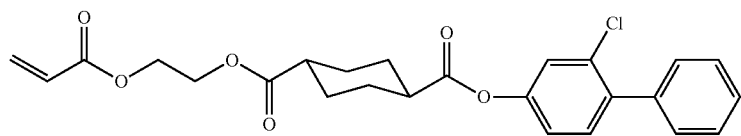
O-11
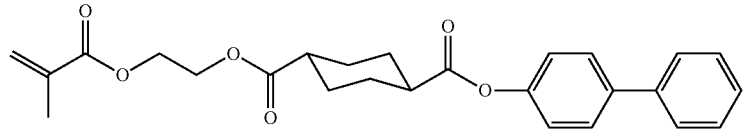
Q-1
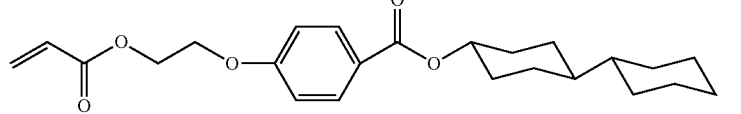
Q-2
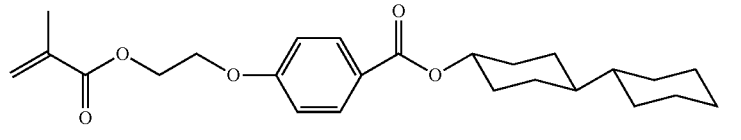
Q-3
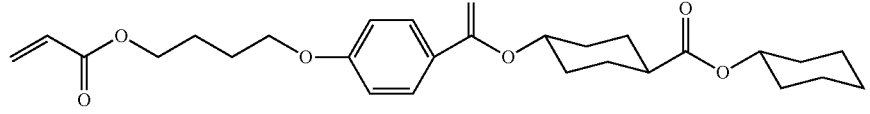
Q-4
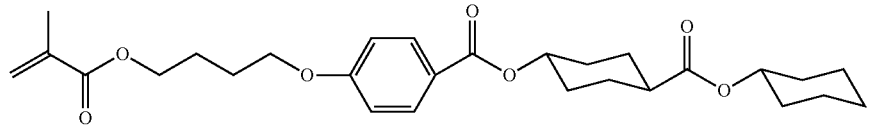

-continued
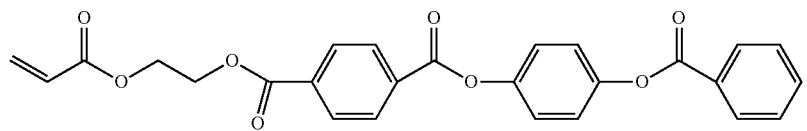
R-1
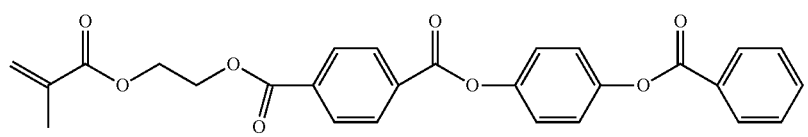
R-2
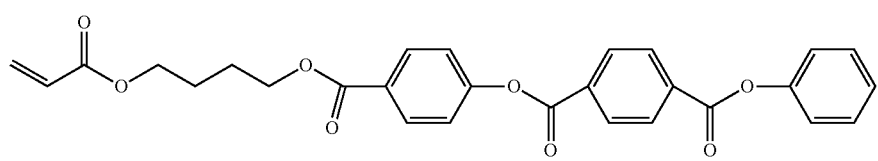
R-3
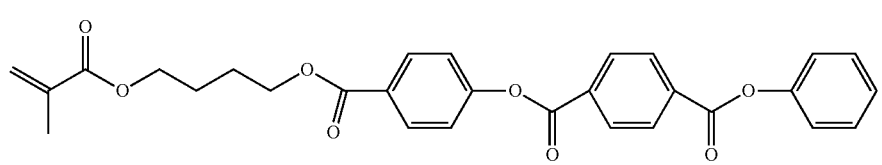
R-4
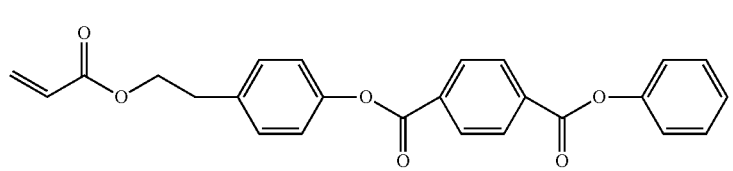
R-5
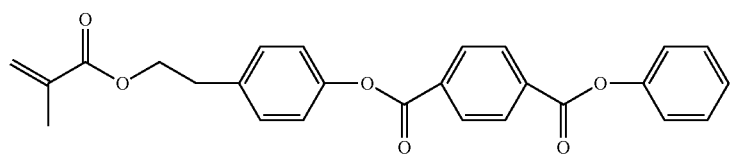
R-6
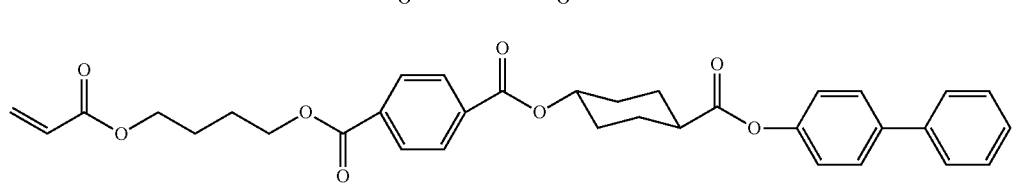
S-1
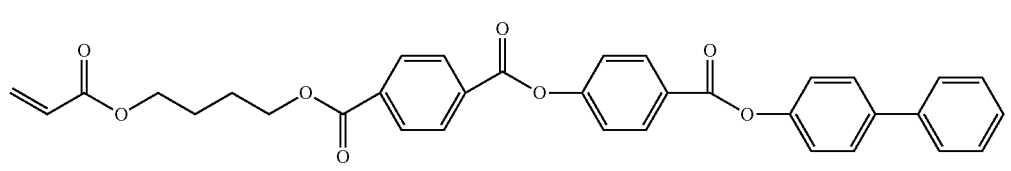
S-2
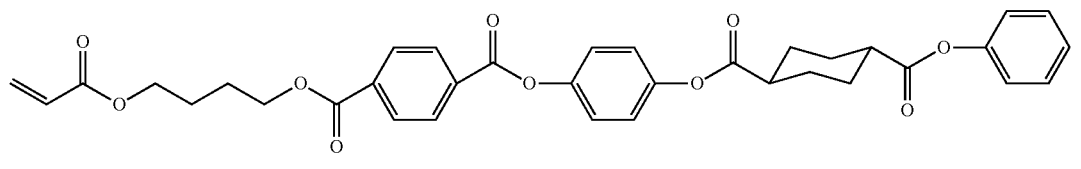
S-3
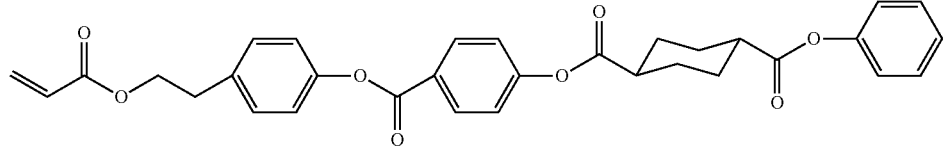
S-4

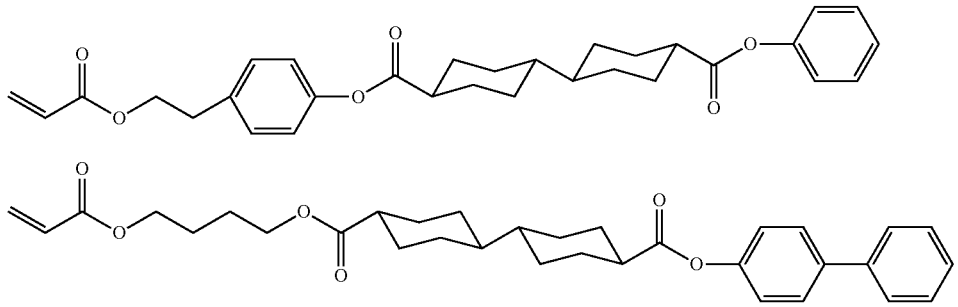

The method for synthesizing the compound (I) is not particularly limited, and a general synthesis method can be adopted. For example, in a case where an esterification reaction is used, examples of the method include a method using an alcohol as a raw material, in which acid chlorination, tosylation, benzenesulfonylation, mesylation, or a condensing agent is used, and in a case where an amidation reaction is used, examples of the method include a method using an amine instead of alcohol as a raw material.

Examples of a solvent used for the reaction or the post-treatment and purification include general-purpose solvents, such as ester-based solvents such as methyl acetate, ethyl acetate, and butyl acetate; ether-based solvents such as tetrahydrofuran, dioxane, and diethyl ether; hydrocarbon-based solvents such as toluene, xylene, n-hexane, n-heptane, and cyclohexane; halogen-based solvents such as ethylene chloride and chloroform; alcohol-based solvents such as methanol, ethanol, and isopropyl alcohol; and water.

Examples of a base used in the reaction include triethylamine, diisopropylethylamine, pyridine, dimethylaminopyridine, and N-methylimidazole.

In the post-treatment step, isolation and purification can be performed using a general method such as liquid separation, crystallization, recrystallization, and silica gel column chromatography.

In a method for removing impurities in the liquid separation and the purification, separation and purification can be performed using aqueous hydrochloric acid, aqueous sodium bicarbonate, saline, or the like.

In the crystallization purification, isolation and purification can be performed using the general-purpose solvent described above.

[Polymerizable Composition]

The polymerizable composition of an embodiment of the present invention is a polymerizable composition containing the above-mentioned compound (I).

[Polymerizable Liquid Crystal Compound]

The polymerizable composition of the embodiment of the present invention preferably contains a polymerizable liquid crystal compound different from the above-mentioned compound (I).

Here, the polymerizable liquid crystal compound means a liquid crystal compound having a polymerizable group.

The liquid crystal compounds can be generally classified into a rod-shaped type and a disk-shaped type according to the shape thereof. Each of the types can further be classified into a low-molecular-weight type and a high-molecular-weight type. The expression, being high-molecular, generally refers to having a degree of polymerization of 100 or more (Polymer Physics Phase Transition Dynamics, by Masao Doi, page 2, published by Iwanami Shoten, Publishers, 1992).

In the present invention, any of liquid crystal compounds can be used, but a rod-shaped liquid crystalline compound or a discotic liquid crystalline compound (disk-shaped liquid crystalline compound) is more preferably used.

In the present invention, the polymerizable liquid crystal compound preferably has two or more polymerizable groups in one molecule from the viewpoint of immobilization of the above-mentioned liquid crystal compound.

The type of the polymerizable group is not particularly limited, a functional group capable of performing an addition polymerization reaction is preferable, and an ethylenically unsaturated polymerizable group or a polymerizable ring group is more preferable. More specifically, preferred examples of the polymerizable group include an acryoly group, a methacryloyl group, a vinyl group, a styryl group, and an allyl group, and the acryloyl group or the methacryloyl group is more preferable.

Among these polymerizable groups, the polymerizable group contained in the polymerizable liquid crystal compound is preferably a polymerizable group different from the polymerizable group contained in the above-mentioned compound (for a reason that the tilt angle of the liquid crystal molecule can be reduced.

As the rod-shaped liquid crystalline compound, for example, the rod-shaped liquid crystalline compounds described in claim 1 of JP1999-513019A (JP-H11-513019A) or paragraphs [0026] to [0098] of JP2005-289980A can be preferably used, and as the discotic liquid crystal compound, for example, the discotic liquid crystalline compounds described in paragraphs [0020] to [0067] of JP2007-108732A and paragraphs [0013] to [0108] of JP2010-244038A can be preferably used, but the rod-shaped liquid crystalline compound is not limited thereto.

In the present invention, it is preferable to use a polymerizable smectic liquid crystal compound as the polymerizable liquid crystal compound.

Here, the "polymerizable smectic liquid crystal compound" is a compound having a polymerizable group and exhibiting a liquid crystal state of the smectic phase.

The liquid crystal state exhibited by the polymerizable smectic liquid crystal compound is preferably a higher-order smectic phase. The higher-order smectic phase as mentioned herein is a smectic A phase, a smectic B phase, a smectic D phase, a smectic E phase, a smectic F phase, a smectic G phase, a smectic H phase, a smectic I phase, a smectic J phase, a smectic K phase, or a smectic L phase, and among these, the smectic A phase, the smectic B phase, the smectic F phase, the smectic I phase, the slanted smectic F phase, or the slanted smectic I phase is preferable, and the smectic A phase or the smectic B phase is more preferable.

Examples of such a polymerizable smectic liquid crystal compound include the compounds described in paragraphs [0043] to [0055] of JP2013-033249A.

In addition, in the present invention, the reverse wavelength dispersible liquid crystal compound can be used as the polymerizable liquid crystal compound.

Here, in the present specification, the "liquid crystal compound exhibiting reverse wavelength dispersibility" means that in a case where an in-plane retardation (Re) value at a specific wavelength (visible light range) of a phase difference film manufactured using the polymerizable liquid crystal compound is measured, the Re value is equal or higher as a measurement wavelength is increased.

In addition, the reverse wavelength dispersible liquid crystal compound is not particularly limited as long as it can form the reverse wavelength dispersible film as described above, and for example, the compound represented by General Formula (I) described in JP2008-297210A (in particular, the compounds described in paragraph Nos. [0034] to [0039]), the compounds represented by General Formula (1) described in JP2010-084032A (in particular, the compounds described in paragraph Nos. [0067] to [0073]), the compound represented by General Formula (II) described in JP2016-053709A (in particular, the compounds described in paragraph Nos. [0036] to [0043]), the compounds represented by General Formula (1) described in JP2016-081035A (in particular, the compounds described in paragraph Nos. [0043] to [0055]), or the like can be used.

In addition, for a reason that the reverse wavelength dispersibility is improved, suitable examples of the polymerizable liquid crystal compound include compounds represented by Formulae (I) to (22), and specifically include the compounds having side chain structures shown in Tables 1 to 3 below as K (side chain structure) in Formulae (1) to (22).

Furthermore, in Tables 1 to 3 below, "*" shown in the side chain structure of K represents a bonding position to an aromatic ring.

In addition, in the side chain structure shown in 1-2 in Table 2 below and 2-2 in Table 3 below, a group adjacent to each of the acryloyloxy group and the methacryloyl group represents a propylene group (a group in which a methyl group is substituted with an ethylene group), and represents a mixture of regioisomers in which the positions of the methyl groups are different.

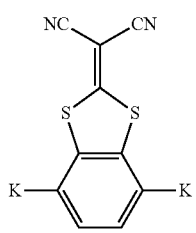

(1)

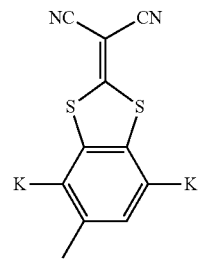

(2)

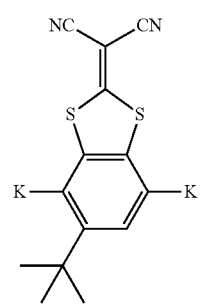

(3)

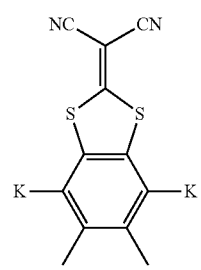

(4)

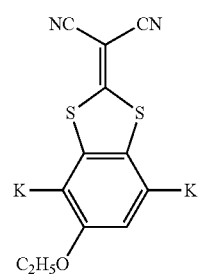

(5)

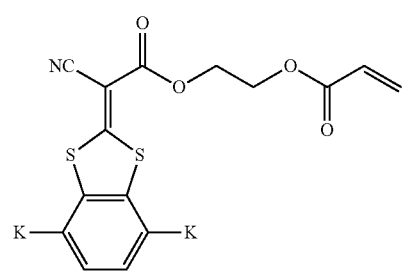

(6)

(7)
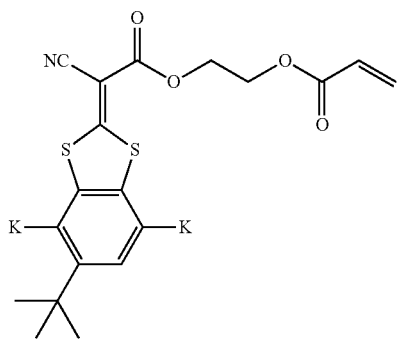
(8)
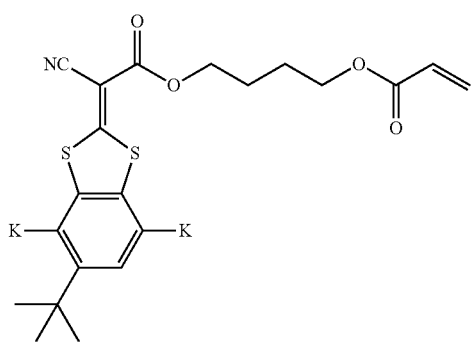
(9)
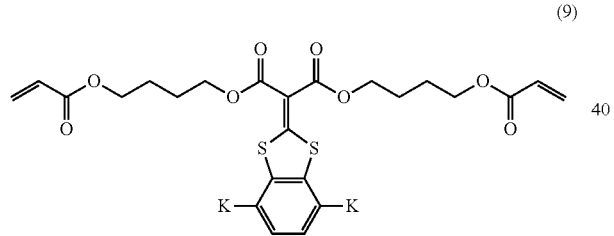
(10)
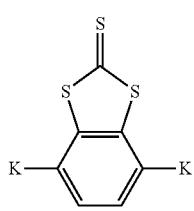
(11)
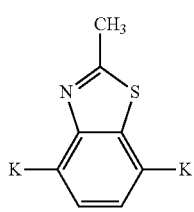
(12)
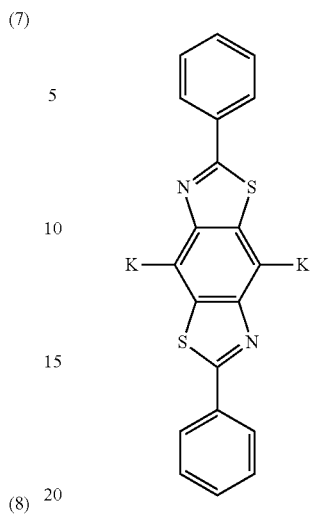
(13)
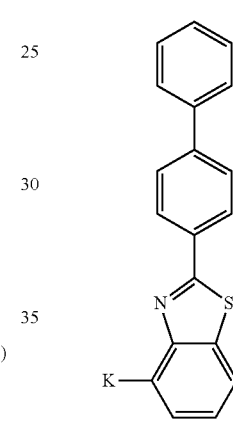
(14)
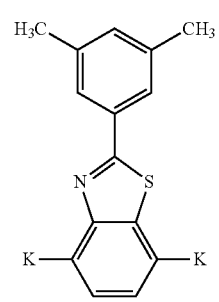
(15)
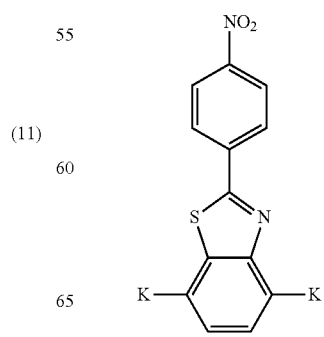

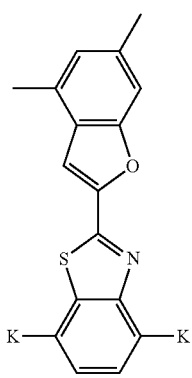
(16)
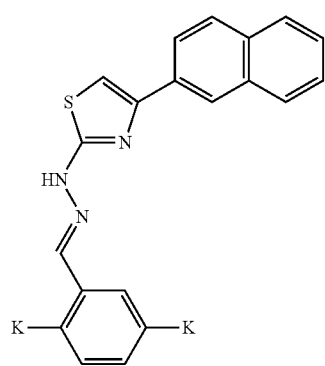
(20)
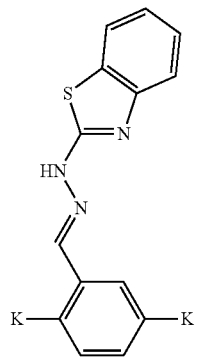
(17)
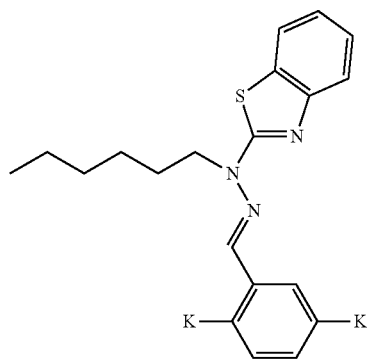
(18)
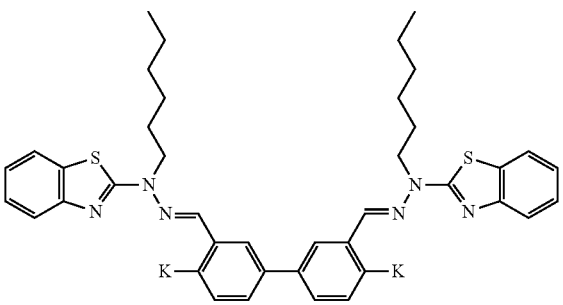
(21)
(19)
(22)

TABLE 1

Table 1  K (side chain structure)

| | |
|---|---|
| 1-1 | *—O—C(=O)—[cyclohexane-1,4-diyl]—C(=O)—O—[1,4-phenylene]—O—C$_6$H$_{12}$—O—C(=O)—CH=CH$_2$ |
| 1-2 | *—O—C(=O)—[cyclohexane-1,4-diyl]—C(=O)—O—[1,4-phenylene]—O—C$_{11}$H$_{22}$—O—C(=O)—CH=CH$_2$ |
| 1-3 | *—O—C(=O)—[cyclohexane-1,4-diyl]—C(=O)—O—[1,4-phenylene]—O—CH$_2$CH$_2$—O—CH$_2$CH$_2$—O—CH$_2$CH$_2$—O—C(=O)—CH=CH$_2$ |
| 1-4 | *—O—C(=O)—[cyclohexane-1,4-diyl]—C(=O)—O—[1,4-phenylene]—O—CH$_2$CH$_2$—O—CH$_2$CH$_2$—O—C(=O)—CH=CH$_2$ |
| 1-5 | *—O—C(=O)—[1,4-phenylene]—O—(CH$_2$)$_6$—O—C(=O)—CH=CH$_2$ |
| 1-6 | *—O—C(=O)—[cyclohexane-1,4-diyl]—C(=O)—O—[1,4-phenylene]—O—C(=O)—(CH$_2$)$_4$—O—C(=O)—CH=CH$_2$ |

TABLE 2

Table 2  K (side chain structure)

| | |
|---|---|
| 2-1 | *—O—C(=O)—[cyclohexane-1,4-diyl]—[cyclohexane-1,4-diyl]—C(=O)—O—CH$_2$CH$_2$—O—C(=O)—CH=CH$_2$ |
| 2-2 | *—O—C(=O)—[cyclohexane-1,4-diyl]—[cyclohexane-1,4-diyl]—C(=O)—O—CH$_2$—C(CH$_3$)$_2$—CH$_2$—O—C(=O)—CH=CH$_2$ |
| 2-3 | *—O—C(=O)—[cyclohexane-1,4-diyl]—[cyclohexane-1,4-diyl]—C(=O)—O—CH$_2$CH$_2$CH$_2$—O—C(=O)—CH=CH$_2$ |

TABLE 2-continued
Table 2 K (side chain structure)
2-4
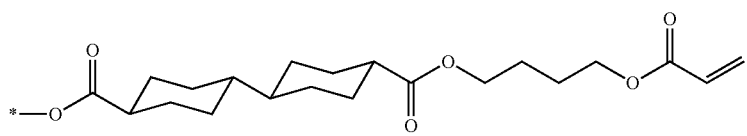 [SMILES: *OC(=O)C1CCC(C2CCC(C(=O)OCCCCOC(=O)C=C)CC2)CC1]
2-5
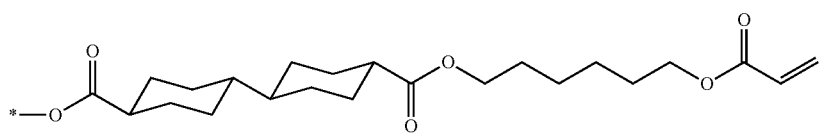 [SMILES: *OC(=O)C1CCC(C2CCC(C(=O)OCCCCCCOC(=O)C=C)CC2)CC1]
2-6
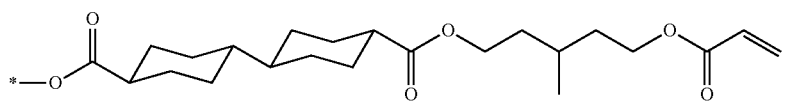 [SMILES: *OC(=O)C1CCC(C2CCC(C(=O)OCCC(C)CCOC(=O)C=C)CC2)CC1]
2-7
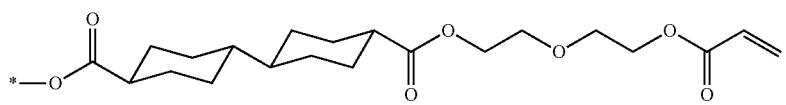 [SMILES: *OC(=O)C1CCC(C2CCC(C(=O)OCCOCCOC(=O)C=C)CC2)CC1]
2-8
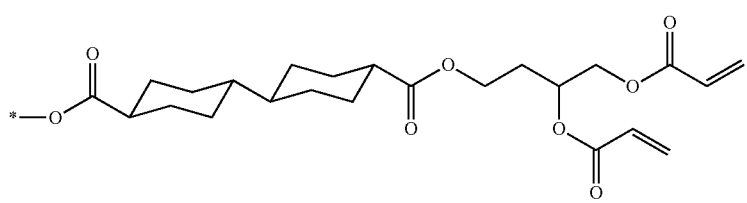 [SMILES: *OC(=O)C1CCC(C2CCC(C(=O)OCCC(COC(=O)C=C)OC(=O)C=C)CC2)CC1]
2-9
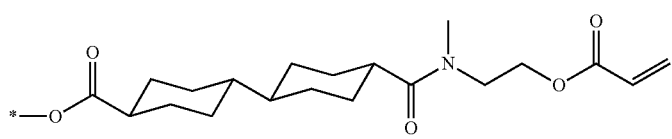 [SMILES: *OC(=O)C1CCC(C2CCC(C(=O)N(C)CCOC(=O)C=C)CC2)CC1]
2-10
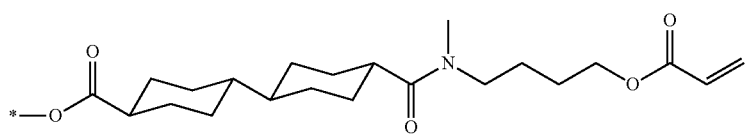 [SMILES: *OC(=O)C1CCC(C2CCC(C(=O)N(C)CCCCOC(=O)C=C)CC2)CC1]
2-11
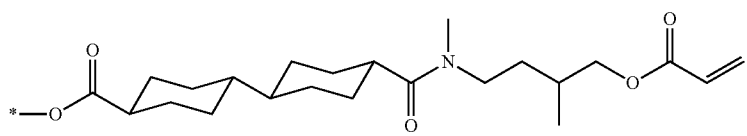 [SMILES: *OC(=O)C1CCC(C2CCC(C(=O)N(C)CCC(C)COC(=O)C=C)CC2)CC1]
2-12
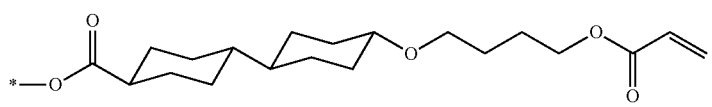 [SMILES: *OC(=O)C1CCC(C2CCC(OCCCCOC(=O)C=C)CC2)CC1]
2-13
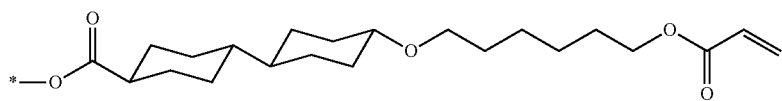 [SMILES: *OC(=O)C1CCC(C2CCC(OCCCCCCOC(=O)C=C)CC2)CC1]
2-14

TABLE 3
Table 3 K (side chain structure)
3-1
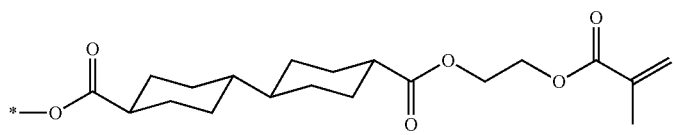
3-2
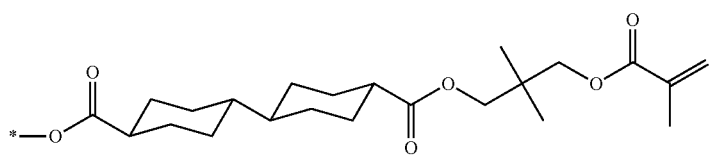 [SMILES: *OC(=O)C1CCC(C2CCC(C(=O)OCC(C)(C)COC(=O)C(=C)C)CC2)CC1]
3-3
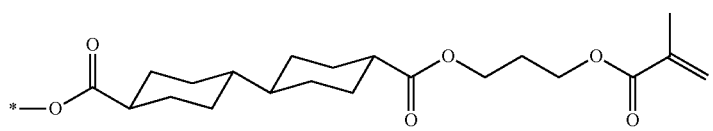 [SMILES: *OC(=O)C1CCC(C2CCC(C(=O)OCCCOC(=O)C(=C)C)CC2)CC1]
3-4
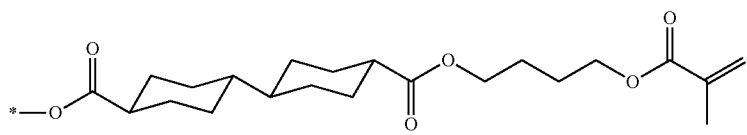 [SMILES: *OC(=O)C1CCC(C2CCC(C(=O)OCCCCOC(=O)C(=C)C)CC2)CC1]
3-5
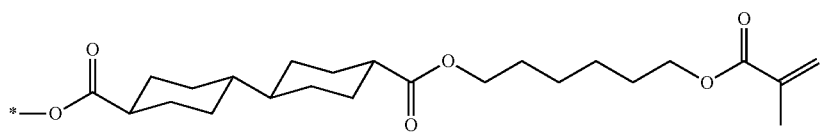 [SMILES: *OC(=O)C1CCC(C2CCC(C(=O)OCCCCCCOC(=O)C(=C)C)CC2)CC1]
3-6
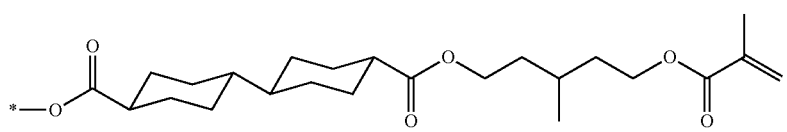 [SMILES: *OC(=O)C1CCC(C2CCC(C(=O)OCCC(C)CCOC(=O)C(=C)C)CC2)CC1]
3-7
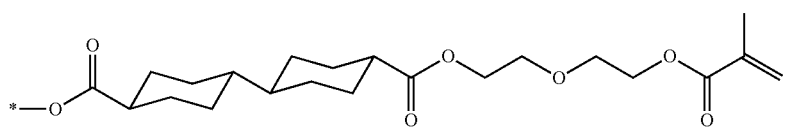
3-8
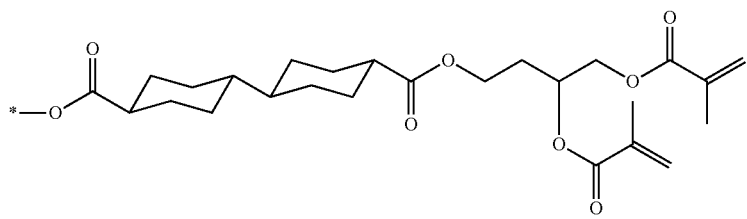 [SMILES: *OC(=O)C1CCC(C2CCC(C(=O)OCCC(COC(=O)C(=C)C)OC(=O)C(=C)C)CC2)CC1]
3-9
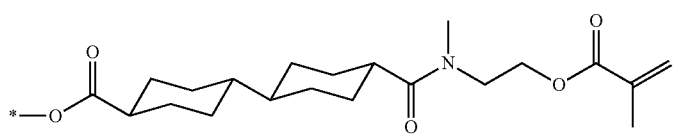
3-10
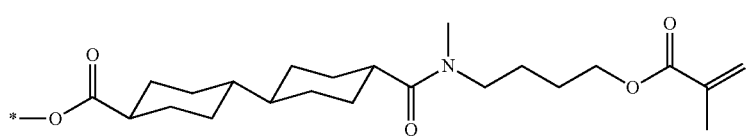

TABLE 3-continued

Table 3 K (side chain structure)

3-11 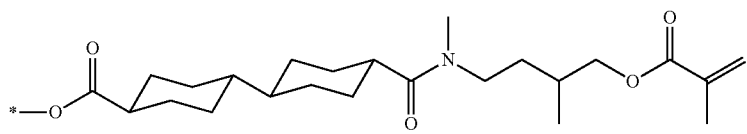 [SMILES: *OC(=O)C1CCC(C2CCC(C(=O)N(C)CCC(C)COC(=O)C(=C)C)CC2)CC1]

3-12 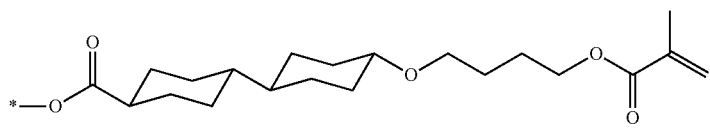 [SMILES: *OC(=O)C1CCC(C2CCC(OCCCCOC(=O)C(=C)C)CC2)CC1]

3-13 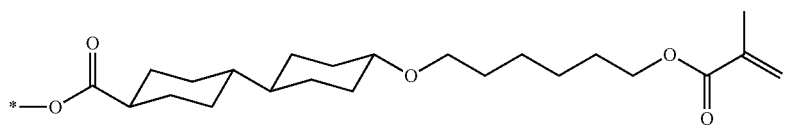 [SMILES: *OC(=O)C1CCC(C2CCC(OCCCCCCOC(=O)C(=C)C)CC2)CC1]

3-14 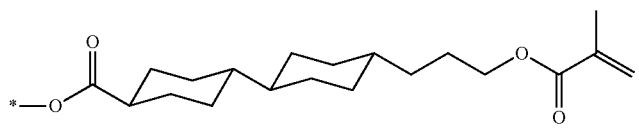 [SMILES: *OC(=O)C1CCC(C2CCC(CCCOC(=O)C(=C)C)CC2)CC1]

In addition, in the present invention, a forward wavelength dispersible liquid crystal compound can be used as the polymerizable liquid crystal compound. In particular, it is preferable to use the forward wavelength dispersible liquid crystal compound together with the above-mentioned reverse wavelength dispersible liquid crystal compound.

Here, the liquid crystal compound exhibiting "forward wavelength dispersibility" the present specification means that in a case where an in-plane retardation (Re) value at a specific wavelength (visible light range) of a phase difference film manufactured using the liquid crystal compound is measured, the Re value is decreased as a measurement wavelength is increased.

Suitable examples of the forward wavelength dispersible liquid crystal compound include compounds represented by Formulae (30) to (53), and specifically include the compounds having side chain structures shown in Tables 2 and 3 below as K (side chain structure) in Formulae (30) to (53).

Further, in Tables 2 and 3, "*" shown in the side chain structure of K represents a bonding position with a benzene ring, a piperazine ring, or a cyclohexane ring in Formulae (30) to (53).

In addition, in the side chain structure shown in 1-2 in Table 2 below and 2-2 in Table 3 below, a group adjacent to each of the acryloyloxy group and the methacryloyl group represents a propylene group (a group in which a methyl group is substituted with an ethylene group), and represents a mixture of position isomers in which the positions of the methyl groups are different.

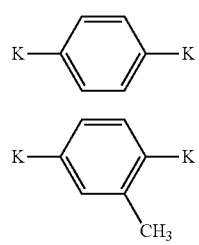 (30)

(31)

(32) 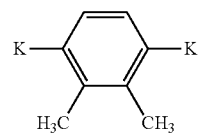

(33) 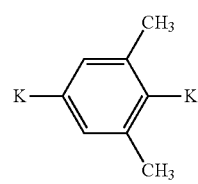

(34) 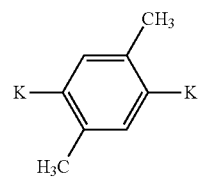

(35) 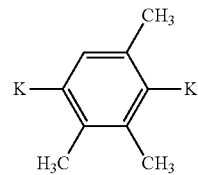

(36) 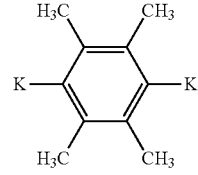

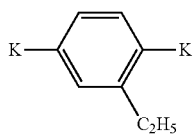 (37)

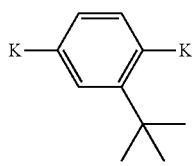 (38)

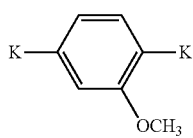 (39)

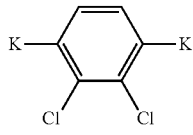 (40)

 (41)

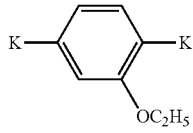 (42)

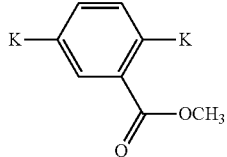 (43)

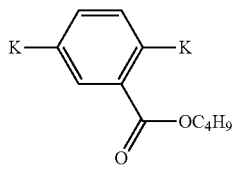 (44)

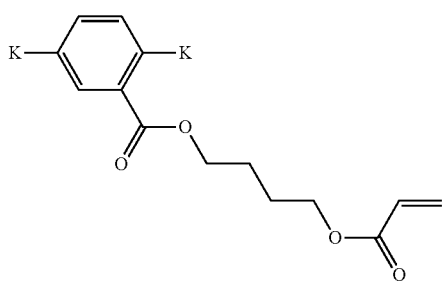 (45)

(46)

(47)

(48)

(49)

(50)

(51)

(52)

(53)

[Polymerization Initiator]

The polymerizable composition of the embodiment of the present invention preferably contains a polymerization initiator.

The polymerization initiator to be used is preferably a photopolymerization initiator capable of initiating a polymerization reaction upon irradiation with ultraviolet rays.

Examples of the photopolymerization initiator include α-carbonyl compounds (described in each of the specifications of U.S. Pat. Nos. 2,367,661A and 2,367,670A), acyloin ethers (described in the specification of U.S. Pat. No. 2,448,828A), α-hydrocarbon-substituted aromatic acyloin compounds (described in the specification of U.S. Pat. No. 2,722,512A), multinuclear quinone compounds (described in each of the specifications of U.S. Pat. Nos. 3,046,127A and 2,951,758A), combinations of a triarylimidazole dimer and a p-aminophenyl ketone (described in the specification of U.S. Pat. No. 3,549,367A), acridine and phenazine compounds (described in JP1985-105667A (JP-S60-105667A) and the specification of U.S. Pat. No. 4,239,850A), oxadiazole compounds (described in the specification of U.S. Pat. No. 4,212,970A), and acyl phosphine oxide compounds (described in JP1988-40799B (JP-S63-40799B), JP1993-29234B (JP-H05-29234B), JP1998-95788A (JP-H10-95788A), and JP1998-29997A (JP-H10-29997A)).

In addition, in the present invention, it is also preferable that the polymerization initiator is an oxime-type polymerization initiator, and specific examples of the polymerization initiator include the initiators described in paragraphs [0049] to [0052] of WO2017/170443A.

[Solvent]

It is preferable that the polymerizable composition of the embodiment of the present invention contains a solvent from the viewpoint of workability for forming a cured product (for example, an optically anisotropic layer) of an embodiment of the present invention, which will be described later.

Specific examples of the solvent include ketones (for example, acetone, 2-butanone, methyl isobutyl ketone, cyclohexanone, and cyclopentanone), ethers (for example, dioxane and tetrahydrofuran), aliphatic hydrocarbons (for example, hexane), alicyclic hydrocarbons (for example, cyclohexane), aromatic hydrocarbons (for example, toluene, xylene, and trimethylbenzene), halogenated carbons (for example, dichloromethane, dichloroethane, dichlorobenzene, and chlorotoluene), esters (for example, methyl acetate, ethyl acetate, and butyl acetate), water, alcohols (for example, ethanol, isopropanol, butanol, and cyclohexanol), cellosolves (for example, methyl cellosolve and ethyl cellosolve), cellosolve acetates, sulfoxides (for example, dimethyl sulfoxide), and amides (for example, dimethylformamide and dimethylacetamide), and these may be used singly or in combination of two or more kinds thereof

[Leveling Agent]

It is preferable that the polymerizable composition of the embodiment of the present invention contains a leveling agent from the viewpoint that the surface of a cured product of the embodiment of the present invention, which will be described later, is maintained smooth and the alignment is easily controlled.

Such a leveling agent is preferably a fluorine-based leveling agent or a silicon-based leveling agent for a reason that it has a high leveling effect on the addition amount, and the leveling agent is more preferably a fluorine-based leveling agent from the viewpoint that it is less likely to cause bleeding (bloom or bleed).

Specific example of the leveling agent include the compounds described in paragraphs [0079] to [0102] of JP2007-069471A, the compound represented by General Formula (I) described in JP2013-047204A (in particular, the compounds described in paragraphs [0020] to [0032]), the compound represented by General Formula (I) described in JP2012-211306A (in particular, the compounds described in paragraphs [0022] to [0029]), the liquid crystal alignment accelerator represented by General Formula (I) described in JP2002-129162A (in particular, the compounds described in paragraphs [0076] to [0078] and [0082] to [0084]), and the compounds represented by General Formulae (I), (II), and (III) described in JP2005-099248A (in particular, the compounds described in paragraphs [0092] to [0096]). In addition, the leveling agent may also function as an alignment control agent which will be described later.

[Alignment Control Agent]

The polymerizable composition of the embodiment of the present invention can contain an alignment control agent, as desired.

With the alignment control agent, various alignment states such as homeotropic alignment (vertical alignment), tilt alignment, hybrid alignment, and cholesteric alignment can be formed, in addition to the homogeneous alignment, and specific alignment states can be controlled and achieved more uniformly and more accurately.

As an alignment control agent which accelerates the homogeneous alignment, for example, a low-molecular-weight alignment control agent or a high-molecular-weight alignment control agent can be used.

With regard to the low-molecular-weight alignment control agent, reference can be made to the description in, for example, paragraphs [0009] to [0083] of JP2002-20363A, paragraphs [0111] to [0120] of JP2006-106662A, and paragraphs [0021] to [0029] of JP2012-211306A, the contents of which are hereby incorporated by reference.

In addition, with regard to the high-molecular-weight alignment control agent, reference can be made to the description in, for example, paragraphs [0021.] to [0057] of JP2004-198511A and paragraphs [0121] to [0167] of JP2006-106662A, the contents of which are hereby incorporated by reference.

Furthermore, examples of the alignment control agent that forms or accelerates the homeotropic alignment include a boronic acid compound and an onium salt compound, and specifically, reference can be made to the compounds described in paragraphs [0023] to [0032] of JP2008-225281A, paragraphs [0052] to [0058] of JP2012-208397A, paragraphs [0024] to of JP2008-026730A, paragraphs [0043] to [0055] of JP2016-193869A, and the like, the contents of which are hereby incorporated by reference.

On the other hand, the cholesteric alignment can be achieved by adding a chiral agent to the composition of the embodiment of the present invention, and it is possible to control the direction of revolution of the cholesteric alignment by its chiral direction.

Incidentally, it is possible to control the pitch of the cholesteric alignment in accordance with the alignment regulating force of the chiral agent.

In a case where an alignment control agent is contained, a content thereof is preferably 0.01% to 10% by mass, and more preferably 0.05% to 5% by mass with respect to the mass of the total solid content of the composition. In a case where the content is within the range, it is possible to obtain a cured product which has no precipitation or phase separation, alignment defects, or the like, and is uniform and highly transparent while achieving a desired alignment state.

These alignment control agents can further impart a polymerizable functional group, in particular, a polymerizable functional group that is polymerizable with the compound (I) included in the composition of the embodiment of the present invention.

[Other Components]

The polymerizable composition of the embodiment of the present invention may contain components other than the above-mentioned components, and examples of such other components include a surfactant, a tilt angle control agent, an alignment assistant, a plasticizer, and a crosslinking agent.

[Cured Product]

The cured product of the embodiment of the present invention is a cured product obtained by curing the above-mentioned polymerizable composition of the embodiment of the present invention.

Here, in a case where the polymerizable composition of the embodiment of the present invention contains, for example, a polymerizable liquid crystal compound different from the above-mentioned compound (I) together with the compound (I), it is possible to form an optically anisotropic layer as a cured product by polymerizing the polymerizable composition of the embodiment of the present invention.

Examples of a method for forming the cured product include a method in which the above-mentioned polymerizable composition of the embodiment of the present invention is used to cause a desired alignment state, and then fixed by polymerization.

Here, the polymerization conditions are not particularly limited, but in the polymerization by irradiation with light, ultraviolet rays are preferably used. The irradiation dose is preferably 10 mJ/cm$^2$ to 50 J/cm$^2$, more preferably 20 mJ/cm$^2$ to 5 J/cm$^2$, still more preferably 30 mJ/cm$^2$ to 3 J/cm$^2$, and particularly preferably 50 mJ/cm$^2$ to 1,000 mJ/cm$^2$. In addition, the polymerization may be carried out under a heating condition in order to accelerate the polymerization reaction.

In addition, in the present invention, the cured product can be formed on any of supports in the optical film of the embodiment of the present invention, which will be described later or a polarizer in the polarizing plate of an embodiment of the present invention, which will be described later.

The cured product of the embodiment of the present invention is preferably an optically anisotropic layer satisfying Formula (II).

$$0.50 < Re(450)/Re(550) < 1.00 \quad \text{(II)}$$

Here, in Formula (II), Re(450) represents an in-plane retardation at a wavelength of 450 nm of the optically anisotropic layer, and Re(550) represents an in-plane retardation at a wavelength of 550 nm of the optically anisotropic layer. In addition, in the present specification, in a case where the measurement wavelength of the retardation is not specified, the measurement wavelength is 550 nm.

Furthermore, the values of the in-plane retardation and the thickness-direction retardation refer to values measured with light at the measurement wavelength using AxoScan OPMF-1 (manufactured by Opto Science, Inc.).

Specifically, by inputting the average refractive index ((Nx+Ny+Nz)/3) and the film thickness (d (μm)) to AxoScan OPMF-1, it is possible to calculate:

Slow axis direction (°)

$$Re(\lambda) = R0(\lambda)$$

$$Rth(\lambda) = ((nx+ny)/2 - nz) \times d.$$

In addition, R0(λ) is expressed in a numerical value calculated with AxoScan OPMF-1, but means Re(λ).

In addition, such an optically anisotropic layer is preferably a positive A-plate or a positive C-plate, and more preferably the positive A-plate.

Here, the positive A-plate (A-plate which is positive) and the positive C-plate (C-plate which is positive) are defined as follows.

In a case where a refractive index in a film in-plane slow axis direction (in a direction in which an in-plane refractive index is maximum) is defined as nx, a refractive index in an in-plane direction orthogonal to the in-plane slow axis is defined as ny, and a refractive index in a thickness direction is defined as nz, the positive A-plate satisfies the relationship of Formula (A1) and the positive C-plate satisfies the relationship of Formula (C1). In addition, the positive A-plate has an Rth showing a positive value and the positive C-plate has an Rth showing a negative value.

$$nx > ny \approx nz \quad \text{Formula (A1)}$$

$$nz > nx \approx ny \quad \text{Formula (C1)}$$

Furthermore, the symbol, "≈", encompasses not only a case where the both are completely the same as each other but also a case where the both are substantially the same as each other.

The expression, "substantially the same", means that with regard to the positive A-plate, for example, a case where (ny−nz)×d (in which d is the thickness of a film) is −10 to 10 nm, and preferably −5 to 5 nm is also included in "ny nz", and a case where (nx−nz)×d is −10 to 10 nm, and preferably −5 to 5 nm is also included in "nx≈nz". In addition, with regard to the positive C-plate, for example, a case where (nx−ny)×d (in which d is the thickness of a film) is 0 to 10 nm, and preferably 0 to 5 nm is also included in "nx≈ny".

In a case where the optically anisotropic layer is a positive A-plate, the Re(550) is preferably 100 to 180 nm, more preferably 120 to 160 nm, still more preferably 130 to 150 nm, and particularly preferably 130 to 140 nm, from the viewpoint that the optically anisotropic layer functions as a λ/4 plate.

Here, the "λ/4 plate" is a plate having a λ/4 function, specifically, a plate having a function of converting a linearly polarized light at a certain specific wavelength into a circularly polarized light (or converting a circularly polarized light to a linearly polarized light).

[Optical Film]

The optical film of the embodiment of the present invention is an optical film having the cured product of the embodiment of the present invention.

Figure 1B:
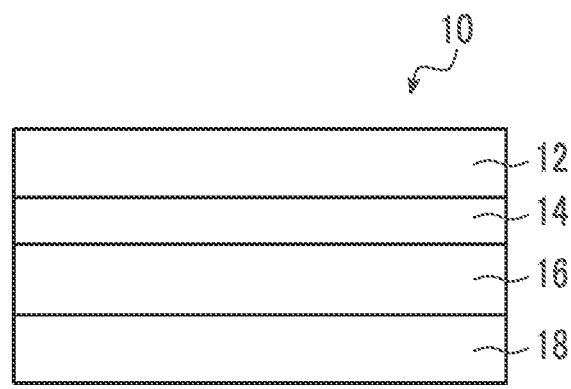
FIG. 1B is a schematic cross-sectional view showing an example of the optical film of the present invention.
Figure 1C:
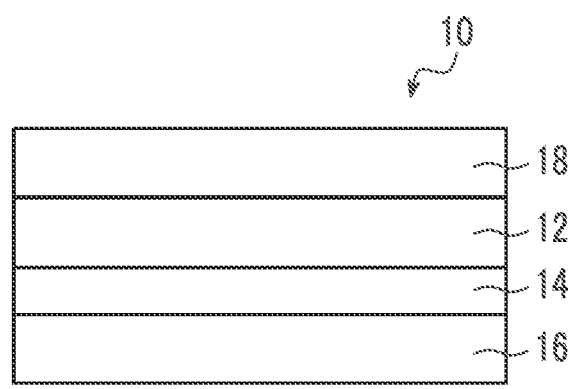
FIG. 1C is a schematic cross-sectional view showing an example of the optical film of the present invention.

FIG. 1A, FIG. 1B, and FIG. 1C (these drawings are hereinafter simply referred to as "FIG. 1" unless it is necessary that they are particularly distinguished from each other) are each a schematic cross-sectional view showing an example of the optical film of the embodiment of the present invention.

Furthermore, FIG. 1 is a schematic view, and the thicknesses relationship, the positional relationship, and the like among the respective layers are not necessarily consistent with actual ones, and any of the support, the alignment film, and the hard coat layer shown in FIG. 1 are optional constitutional members.

An optical film 10 shown in FIG. 1 has a support 16, an alignment film 14, and an optically anisotropic layer 12 as the cured product in this order.

In addition, the optical film 10 may have a hard coat layer 18 on the side of the support 16 opposite to the side on which the alignment film 14 is provided as shown in FIG. 1B, and may have the hard coat layer 18 on the side of the optically anisotropic layer 12 opposite to the side on which the alignment film 14 is provided as shown in FIG. 1C.

Hereinafter, various members used for the optical film of the embodiment of the present invention will be described in detail.

[Cured Product]

The cured product contained in the optical film of the embodiment of the present invention is the above-mentioned cured product of the embodiment of the present invention.

In the optical film of the embodiment of the present invention, the thickness of the cured product is not particularly limited, but in a case where the optical film functions as an optically anisotropic layer is preferably 0.1 to 10 μm, and more preferably 0.5 to 5 μm.

[Support]

The optical film of the embodiment of the present invention may have a support as a base material for forming a cured product as described above.

Such a support is preferably transparent, and specifically, it preferably has a light transmittance of 80% or more.

Examples of such a support include a glass substrate and a polymer film, and examples of the material for the polymer film include cellulose-based polymers; acrylic polymers having an acrylic ester polymer such as polymethyl methacrylate and a lactone ring-containing polymer; thermoplastic norbornene-based polymers; polycarbonate-based polymers; polyester-based polymers such as polyethylene terephthalate and polyethylene naphthalate; styrene-based polymers such as polystyrene and an acrylonitrile-styrene copolymer (AS resin); polyolefin-based polymers such as polyethylene, polypropylene, and an ethylene-propylene copolymer; vinyl chloride-based polymers; amide-based polymers such as nylon and aromatic polyamide; imide-based polymers; sulfone-based polymers; polyether sulfone-based polymers; polyether ether ketone-based polymers; polyphenylene sulfide-based polymers; vinylidene chloride-based polymers; vinyl alcohol-based polymers; vinyl butyral-based polymers; arylate-based polymers; polyoxymethylene-based polymers; epoxy-based polymers; and polymers obtained by mixing these polymers.

In addition, an aspect in which a polarizer which will be described later may also function as such a support is also available.

In the present invention, the thickness of the support is not particularly limited, but is preferably 5 to 60 μm, and more preferably 5 to 30 μm.

[Alignment Film]

In a case where the optical film of the embodiment of the present invention has any of the above-mentioned supports, it is preferable that the optical film has an alignment film between the support and the cured product. Further, an aspect in which the above-mentioned support may also function as an alignment film is also available.

The alignment film generally has a polymer as a main component. Polymer materials for an alignment film are described in many documents, and many commercially available products can be used.

The polymer material used in the present invention is preferably a polyvinyl alcohol or a polyimide, or a derivative thereof. Particularly, a modified or non-modified polyvinyl alcohol is preferable.

Examples of the alignment film that can be used in the present invention include the alignment films described for Line 24 on Page 43 to Line 8 on Page 49 of WO01/88574A; the modified polyvinyl alcohols described in paragraphs [0071] to [0095] of JP3907735B; and the liquid crystal alignment film formed by a liquid crystal alignment agent described in JP2012-155308A.

In the present invention, for a reason that it is possible to prevent deterioration in the surface condition by avoiding a contact with a surface of an alignment film upon formation of the alignment film, a photo-alignment film is also preferably used as the alignment film.

The photo-alignment film is not particularly limited, but the polymer materials such as a polyamide compound and a polyimide compound, described in paragraphs 0024 to 0043 of WO2005/096041A; the liquid crystal alignment film formed by a liquid crystal alignment agent having a photo-alignment group, described in JP2012-155308A; LPP-JP265CP, trade name, manufactured by Rolic Technologies Ltd.; or the like can be used.

In addition, in the present invention, the thickness of the alignment film is not particularly limited, but from the viewpoint of forming an optically anisotropic layer having a uniform film thickness by alleviating the surface roughness that can be present on the support, the thickness is preferably 0.01 to 10 μm, more preferably 0.01 to 1 μm, and still more preferably 0.01 to 0.5 μm.

[Hard Coat Layer]

It is preferable that the optical film of the embodiment of the present invention has a hard coat layer in order to impart physical strength to the film. Specifically; the optical film may have the hard coat layer on the side of the support opposite to the side on which the alignment film is provided see FIG. 1B) or the optical film may have the hard coat layer on the side of the optically anisotropic layer opposite to the side on which the alignment fill is provided (see FIG. 1C).

As the hard coat layer, those described in paragraphs [0190] to [0196] of JP2009-98658A can be used.

[Ultraviolet Absorber]

The optical film of the embodiment of the present invention preferably includes an ultraviolet (UV) absorber, taking an effect of external light (particularly ultraviolet rays) into consideration.

The ultraviolet absorber may be contained in the cured product of the embodiment of the present invention or may also be contained in a member other than the cured product constituting the optical film of the embodiment of the present invention. Suitable examples of the member other than the cured product include a support.

As the ultraviolet absorber, any one of ultraviolet absorbers known in the related art, which can express ultraviolet absorptivity, can be used, Among such the ultraviolet absorbers, a benzotriazole-based or hydroxyphenyltriazine-based ultraviolet absorber is preferably used from the viewpoint that it has high ultraviolet absorptivity and ultraviolet absorbing ability (ultraviolet-shielding ability) used for an image display device is obtained.

In addition, in order to broaden ultraviolet absorbing ranges, two or more of ultraviolet absorbers having different maximum absorption wavelengths can be used in combination.

Specific examples of the ultraviolet absorber include the compounds described in paragraphs [0258] and [0259] of JP2012-18395A and the compounds described in paragraphs [0055] to [0105] of JP2007-72163A.

In addition, as a commercially available product thereof, for example, Tinuvin 400, Tinuvin 405, Tinuvin 460, Tinuvin 477, Tinuvin 479, and Tinuvin 1577 (all manufactured by BASF), or the like can be used.

[Polarizing Plate]

A polarizing plate of an embodiment of the present invention has the above-mentioned optical film of the embodiment of the present invention and a polarizer.

Furthermore, in a case where the optically anisotropic layer as the above-mentioned cured product of the embodiment of the present invention is a λ/4 plate (positive A-plate), the polarizing plate of the embodiment of the present invention can be used as a circularly polarizing plate.

In addition, in a case where the optically anisotropic layer as the above-mentioned cured product of the embodiment of the present invention is a λ/4 plate (positive A-plate), an angle between the slow axis of the λ/4 plate and the absorption axis of a polarizer which will be described later is preferably 30° to 60°, more preferably 40° to 50°, still more preferably 42° to 48°, and particularly preferably 45° in the polarizing plate of the embodiment of the present invention.

Here, the "slow axis" of the λ/4 plate means a direction in which the refractive index in the plane of the λ/4 plate is a maximum, and the "absorption axis" of the polarizer means a direction in which the absorbance is highest.

[Polarizer]

A polarizer contained in a polarizing plate of an embodiment of the present invention is not particularly limited as long as it is a member having a function of converting light into specific linearly polarized light, and an absorptive type polarizer and a reflective type polarizer, which are known in the related art, can be used.

An iodine-based polarizer, a dye-based polarizer using a dichroic dye, a polyene-based polarizer, or the like is used as the absorptive type polarizer. The iodine-based polarizer and the dye-based polarizer are classified into a coating type polarizer and a stretching type polarizer, any of which can be applied, but a polarizer which is manufactured by allowing polyvinyl alcohol to adsorb iodine or a dichroic dye and performing stretching is preferable.

In addition, examples of a method of obtaining a polarizer by carrying out stretching and dyeing in a state of a laminated film in which a polyvinyl alcohol layer is formed on a base material include the methods disclosed in JP5048120B, JP5143918B, JP4691205B, JP4751481B, and JP4751486B, and known technologies relating to these polarizers can also be preferably used.

A polarizer in which thin films having different birefringence are laminated, a wire grid-type polarizer, a polarizer having a combination of a cholesteric liquid crystal having a selective reflection range and a ¼ wavelength plate, or the like is used as the reflective type polarizer.

Among those, a polymer containing a polyvinyl alcohol-based resin ($-CH_2-CHOH-$ as a repeating unit) since of its superior adhesion. In particular, a polarizer containing at least one selected from the group consisting of polyvinyl alcohol and an ethylene-vinyl alcohol copolymer) is preferable.

In the present invention, the thickness of the polarizer is not particularly limited, but is preferably 3 μm to 60 μm, more preferably 5 μm to 30 μm, and still more preferably 5 μm to 15 μm.

[Pressure Sensitive Adhesive Layer]

The polarizing plate of the embodiment of the present invention may have a pressure sensitive adhesive layer arranged between the cured product in the optical film of the embodiment of the present invention and the polarizer.

The pressure sensitive adhesive layer used for lamination of the cured product and the polarizer represents, for example, a substance in which a ratio ($\tan \delta = G''/G'$) between a storage elastic modulus G' and a loss elastic modulus G", each measured with a dynamic viscoelastometer, is 0.001 to 1.5, and examples thereof include a so-called pressure sensitive adhesive or a readily creepable substance. Examples of the pressure sensitive adhesive that can be used in the present invention include a polyvinyl alcohol-based pressure sensitive adhesive, but the pressure sensitive adhesive is not limited thereto.

[Image Display Device]

An image display device of an embodiment of the present invention is an image display device having the optical film of the embodiment of the present invention or the polarizing plate of the embodiment of the present invention.

A display element used in the image display device of the embodiment of the present invention is not particularly limited, and examples thereof include a liquid crystal cell, an organic electroluminescent (hereinafter simply referred to as "EL") display panel, and a plasma display panel.

Among those, the liquid crystal cell and the organic EL display panel are preferable, and the liquid crystal cell is more preferable. That is, as the image display device of the embodiment of the present invention, a liquid crystal display device using a liquid crystal cell as a display element or an organic EL display device using an organic EL display panel as a display element is preferable, and the liquid crystal display device is more preferable.

[Liquid Crystal Display Device]

A liquid crystal display device which is an example of the image display device of the embodiment of the present invention is a liquid crystal display device having the above-mentioned polarizing plate of the embodiment of the present invention and a liquid crystal cell.

In addition, in the present invention, it is preferable that the polarizing plate of the embodiment of the present invention is used as the polarizing plate of the front side, and it is more preferable that the polarizing plate of the embodiment of the present invention is used as the polarizing plates on the front and rear sides, among the polarizing plates provided on the both sides of the liquid crystal cell.

Hereinafter, the liquid crystal cell constituting the liquid crystal display device will be described in detail.

<Liquid Crystal Cell>

The liquid crystal cell used for the liquid crystal display device is preferably in a vertical alignment (VA) mode, an optically compensated bend (OCB) mode, an in-plane-switching (IPS) mode, or a twisted nematic (TN) mode, but is not limited thereto.

In a TN-mode liquid crystal cell, rod-shaped liquid crystal molecules are substantially horizontally aligned and are twist-aligned at 60° to 120° during no voltage application thereto. A TN-mode liquid crystal cell is most often used in a color TFT liquid crystal display device and described in numerous documents.

In a VA-mode liquid crystal cell, rod-shaped liquid crystal molecules are substantially vertically aligned during no voltage application thereto. Examples of the VA-mode liquid crystal cell include (1) a VA-mode liquid crystal cell in the narrow sense of the word, in which rod-shaped liquid crystal molecules are substantially vertically aligned during no voltage application thereto, but are substantially horizontally aligned during voltage application thereto (described in JP1990-176625A (JP-H02-176625A)), (2) an MVA-mode liquid crystal cell in which the VA mode is multi-domained for viewing angle enlargement (described in SID97, Digest of Tech. Papers (preprint), 28 (1997) 845), (3) a liquid crystal cell in a mode (n-ASM mode) in which rod-shaped liquid crystal molecules are substantially vertically aligned during no voltage application thereto and are multi-domain-aligned during voltage application thereto (described in Seminar of Liquid Crystals of Japan, Papers (preprint), 58-59 (1998)), and (4) a survival-mode liquid crystal cell (announced in LCD International 98). In addition, the liquid crystal cell may be of any of a patterned vertical alignment (PVA) type, an optical alignment type, and polymer-sustained alignment (PSA) type. Details of these modes are specifically described in JP2006-215326A and JP2008-538819A.

In an IPS-mode liquid crystal cell, rod-shaped liquid crystal molecules are aligned substantially parallel with respect to a substrate, and application of an electric field parallel to the substrate surface causes the liquid crystal molecules to respond planarly. The IPS mode displays black in a state where no electric field is applied and a pair of upper and lower polarizing plates have absorption axes which are orthogonal to each other. A method of improving the viewing angle by reducing light leakage during black display in an oblique direction using an optical compensation sheet is disclosed in JP1998-54982A (JP-H10-54982A), JP1999-202323A (JP-H11-202323A), JP1997-292522A (JP-H09-292522A), JP1999-133408A (JP-H11-133408A), JP1999-305217A (JP-H11-305217A), JP1998-307291A (JP-H10-307291A), and the like.

[Organic EL Display Device]

Suitable examples of the organic EL display device which is an example of the image display device of the embodiment of the present invention include an aspect which includes, from the visible side, a polarizer, a λ/4 plate (a positive A-plate) including the optically anisotropic layer of the embodiment of the present invention, and an organic EL display panel in this order.

Furthermore, the organic EL display panel is a display panel composed of an organic EL device in which an organic light emitting layer (organic electroluminescent layer) is sandwiched between electrodes (between a cathode and an anode). The configuration of the organic EL display panel is not particularly limited but a known configuration is adopted.

Examples

Hereinafter, the present invention will be described in more detail with reference to Examples. The materials, the amounts of materials used, the proportions, the treatment details, the treatment procedure, and the like shown in Examples below can be appropriately modified as long as the modifications do not depart from the spirit of the present invention. Therefore, the scope of the present invention should not be construed as being limited to Examples shown below.

Example 1

A compound A-1 represented by Formula A-1 was synthesized according to the following synthesis scheme.

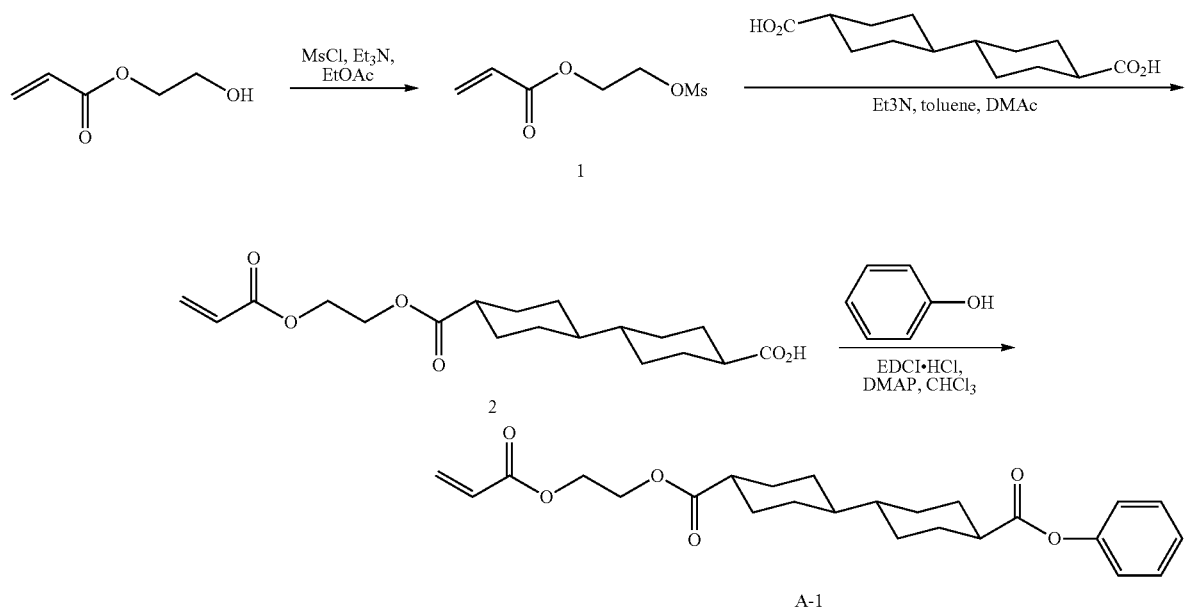

(1) Synthesis of Compound 1

2-Hydroxyethyl acrylate (50.0 g, 0.431 mol) and dibutylhydroxytoluene (190 mg, 0.862 mmol) were dissolved in ethyl acetate (250 mL), triethylamine (51.0 g, 0.504 mol) and methanesulfonic acid chloride (50.4 g, 0.440 mol) were added thereto under ice-cooling, and the mixture was stirred at room temperature for 5 hours, Water (125 mL) was added to the reaction solution and the mixture was extracted with ethyl acetate. The organic layer obtained by extraction was washed with saturated saline and mirabilite was added thereto. The obtained organic layer was filtered to recover the filtrate, dibutylhydroxytoluene (190 mg, 0.862 mmol) was then added thereto, and the solvent was evaporated under reduced pressure to obtain a compound 1 (80.9 g).

(2) Synthesis of Compound 2

The compound 1 (75.6 g, 0.354 mmol) and dibutylhydroxytoluene (0.78 g, 3.5 mmol) were dissolved in a mixed solvent of toluene (180 mL) and dimethylacetamide (200 mL), bicyclohexyl-1,1'-dicarboxylic acid (90.0 g, 0.354 mol) and triethylamine (71.6 g, 0.708 mol) were added thereto at room temperature, and the mixture was stirred at 90° C. for 5 hours. The reaction solution was cooled to room temperature, a mixed solution of concentrated hydrochloric acid (23.4 g) and water (130 mL) was then added thereto, the temperature was then raised to 45° C., and the aqueous layer was removed therefrom. The obtained organic layer was washed with a mixed solution of sodium bicarbonate (13.5 g) and water (260 mL), and a mixed solution of sodium bicarbonate (2.7 g) and water (270 mL) in this order, and magnesium sulfate was added thereto. The obtained organic layer was filtered through Celite to recover the filtrate, dibutylhydroxytoluene (0.78 g, 3.5 mmol) was then added thereto, and the solvent was evaporated from the filtrate under reduced pressure. The obtained residue was dissolved in toluene (360 mL) and hexane (830 mL) was added thereto at 40° C. The solution was cooled to 5° C. under stirring and stirred for 30 minutes. The produced crystals were filtered and washed with hexane to obtain a compound 2 (25.0 g).

(3) Synthesis of Compound A-1

Phenol (1.00 g, 10.6 mmol) and the compound 2 (4.68 g, 13.3 mmol) were dissolved in chloroform (10 mL), 1-(3-dimethylaminopropyl)-3-ethylcarbodiimide hydrochloride (2.75 g, 14.3 mmol) and dimethylaminopyridine (64.9 mg, 0.531 mmol) were added thereto at room temperature, and the mixture was stirred at room temperature for 4 hours. The reaction solution was purified by flash column chromatography to obtain a white solid. The obtained white solid was dissolved in ethyl acetate (10 mL) and hexane (100 mL) was added thereto. The solution was cooled to 0° C. under stirring and stirred for 1 hour. The produced crystals were filtered and washed with hexane to obtain a compound A-1 (0.80 g).

$^1$H-nuclear magnetic resonance (NMR) of the obtained compound A-1 is shown below.

$^1$H-NMR (CDCl$_3$): δ=7.36 (t, 2H), 7.23 (t, 1H), 7.04 (d, 2H), 6.43 (dd, 1H), 6.13 (dd, 1H), 5.88 (dd, 1H), 4.28-4.38 (m, 4H), 2.41-2.52 (m, 1H), 2.13-2.30 (m, 3H), 1.97-2.06 (m, 2H), 1.77-1.90 (m, 4H), 1.33-1.66 (m, 4H), 0.98-1.20 (m, 6H).

Example 2

A compound A-2 represented by Formula A-2 was synthesized according to the following synthesis scheme.

then added thereto, and the solvent was evaporated under reduced pressure to obtain a compound 3 (79.3 g).

(2) Synthesis of Compound 4

The compound 3 (76.6 g, 0.368 mol) and dibutylhydroxytoluene (0.74 g, 3.4 mmol) were dissolved in a mixed solvent of toluene (170 mL) and dimethylacetamide (190 mL), bicyclohexyl-1,1'-dicarboxylic acid (85.0 g, 0.334 mol) and triethylamine (67.6 g, 0.668 mol) were added thereto at room temperature, and the mixture was stirred at 90° C. for 5 hours. The reaction solution was cooled to room temperature, a mixed solution of concentrated hydrochloric acid (22.1 g) and water (120 mL) was then added thereto, the temperature was then raised to 45° C., and the aqueous layer was removed therefrom. The obtained organic layer was washed with a mixed solution of sodium bicarbonate (12.7 g) and water (240 mL), and a mixed solution of sodium bicarbonate (2.5 g), sodium chloride (10 g), and water (350 mL) in this order, and magnesium sulfate was added thereto. The obtained organic layer was filtered through Celite to recover the filtrate, dibutylhydroxytoluene (95.7 mg, 0.434 mmol) was then added thereto, and the solvent was evaporated from the filtrate under reduced pressure. The obtained residue was dissolved in toluene (340 mL) and hexane (630 mL) was added thereto at 40° C. The solution was cooled to 5° C. under stirring and stirred for 30 minutes. The produced crystals were filtered and washed with hexane to obtain a compound 4 (31.3 g).

(3) Synthesis of Compound A-2

Phenol (1.00 g, 10.6 mmol) and the compound 4 (4.87 g, 1.3.3 mmol) were dissolved in chloroform (10 mL), 1-(3-dimethylaminopropyl)-3-ethylcarbodiimide hydrochloride (2.75 g, 14.3 mmol) and dimethylaminopyridine (64.9 mg,

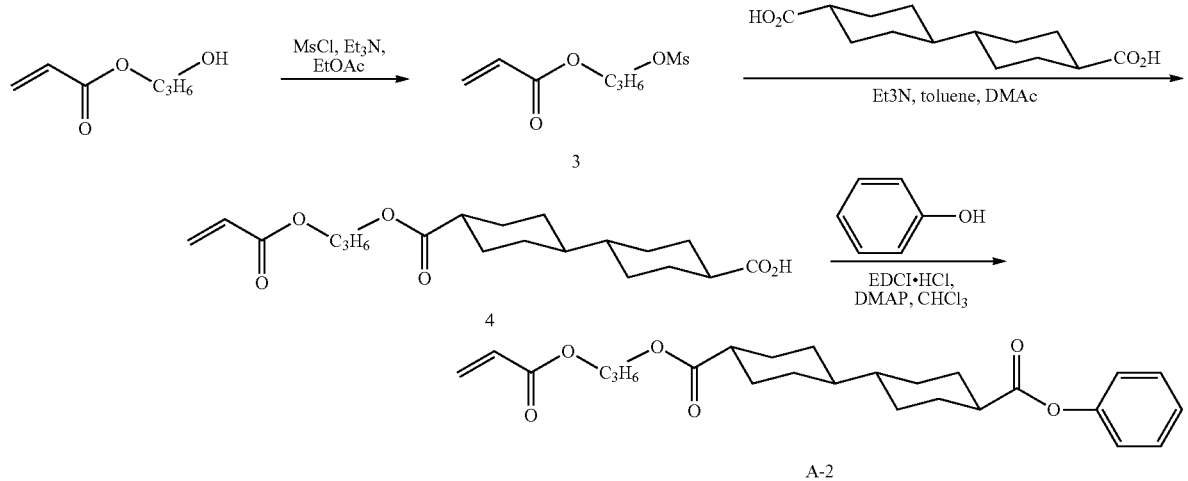

(1) Synthesis of Compound 3

Hydroxypropyl acrylate (50.0 g, 0.384 mol) and dibutylhydroxytoluene (1.69 g, 7.67 mmol) were dissolved in ethyl acetate (250 mL), triethylamine (45.5 g, 0.450 mol) and methanesulfulfonic acid chloride (46.7 g, 0.407 mol) were added thereto under ice-cooling, and the mixture was stirred at room temperature for 2 hours. Water (125 mL) was added to the reaction solution and the mixture was extracted with ethyl acetate. The organic layer obtained by extraction was washed with saturated saline and mirabilite was added thereto. The obtained organic layer was filtered to recover the filtrate, dibutylhydroxytoluene (0.34 g, 1.54 mmol) was 0.531 mmol) were added thereto at room temperature, and the mixture was stirred at room temperature for 4 hours. The compound 4 (4.87 g, 13.3 mmol), 1-(3-dimethylaminopropyl)-3-ethylcarbodiimide hydrochloride (2.75 g, 14.3 mmol) and dimethylaminopyridine (64.9 mg, 0.531 mmol) were added to the reaction solution at room temperature, and the mixture was stirred at room temperature for 4 hours. The reaction solution was purified by flash column chromatography to obtain a white solid. The obtained white solid was dissolved in chloroform (5 mL) and methanol (150 mL) was added thereto. The solution was cooled to 0° C. under stirring and stirred for 1 hour. The produced crystals were filtered and washed with methanol to obtain a compound A-2 (3.23 g).

The $^1$H-NMR of the obtained compound A-2 is shown below.

$^1$H-NMR (CDCl$_3$): δ=7.37 (t, 2H), 7.23 (t, 1H), 7.04 (d, 2H), 6.41 (dd, 1H), 6.12 (dd, 1H), 5.86 (dd, 5.15-5.28 (m, 1H), 4.10-4.23 (m, 2H), 2.46 (tt, 1H), 2. 13-2.29 (m, 3H), 1.95-2.07 (m, 2H), 1.22-1.61 (m, 7H), 0.96-1.19 (m, 6H).

Example 3

A white solid compound A-3 represented by Formula A-3 was Obtained according to the same procedure as in Example 1, except that 2-methoxyphenol was used instead of phenol.

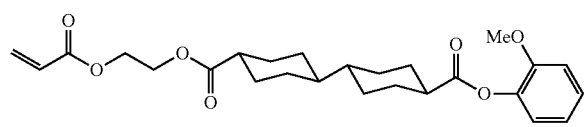

A-3

The $^1$H-NMR of the obtained compound A-3 is shown below.

$^1$H-NMR (CDCl$_3$): δ=7.18 (dt, 1H), 6.90-7.02 (m, 3H), 6.44 (d, 1H), 6.14 (dd, 1H), 5.88 (dd, 1H), 4.28-4.39 (m, 4H), 3.81 (s, 3H), 2.51 (tt, 1H), 2.12-2.31 (m, 3H), 1.95-2.07 (m, 2H), 1.77-1.92 (m, 4H), 1.34-1.63 (m, 4H), 0.97-1.20 (m, 6H).

Example 4

A white solid compound A-4 represented by Formula A-4 was obtained according to the same procedure as in Example 1, except that 2-ethoxyphenol was used instead of phenol.

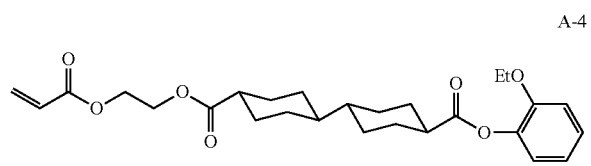 [SMILES: C=CC(=O)OCCOC(=O)C1CCC(C2CCC(C(=O)Oc3ccccc3OCC)CC2)CC1]

A-4

The $^1$H-NMR of the obtained compound A-4 is shown below. $^1$H-NMR (CDCl$_3$): δ=7.14 (dt, 1H), 7.01 (dd, 1H), 6.87-6.95 (m, 2H), 6.44 (dd, 1H), 6.1.4 (dd, 1H) 5.87 (dd, 1H), 4.28-4.39 (m, 4H), 4.02 (q, 2H), 2.50 (tt, 1H), 2.15-2.31 (m, 3H), 1.96-2.07 (m, 2H), 1.68-1.90 (m, 4H), 1.32-1.63 (m, 7H), 0.97-1.18 (m, 6H).

Example 5

A compound A-5 represented by Formula A-5 was synthesized according to the following synthesis scheme.

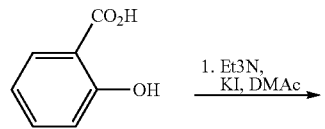

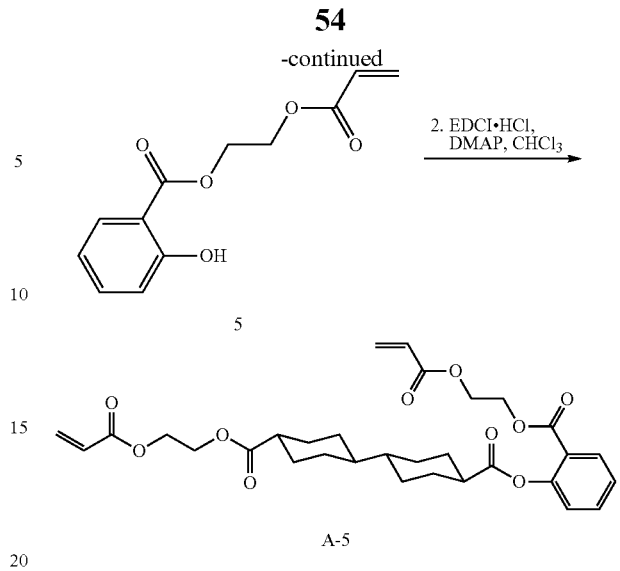

(1) Synthesis of Compound 5

2-Hydroxybenzoic acid (5.01 g, 36.3 mmol), the compound 1 (7.25 g, 37.3 mmol), dibutylhydroxytoluene (0.16 g, 0.73 mind), and potassium iodide (0.30 g, 1.8 mmol) were dissolved in dimethylacetamide (25 mL), triethylamine (4.05 g, 40.0 mmol) was added thereto at room temperature, and the mixture was stirred at 60° C. for 2 hours. The reaction solution was cooled under ice-cooling, 0.5 N hydrochloric acid (100 mL) was then added thereto, and the mixture was extracted with ethyl acetate. The obtained organic layer was washed with water (25 mL), 1 N hydrochloric acid (25 mL), saturated aqueous sodium bicarbonate (25 mL), and saturated saline (25 mL) in this order, and mirabilite was added thereto. The obtained organic layer was filtered to recover the filtrate, dibutylhydroxytoluene (0.16 g, 0.73 mmol) was then added thereto, and the solvent was evaporated from the filtrate under reduced pressure. The obtained residue was purified by flash column chromatography to obtain a compound 5 (6.55 g).

(2) Synthesis of Compound A-5

The compound 5 (1.00 g, 4.23 mmol) and the compound 1 (4.68 g, 5.28 mmol) wore dissolved in chloroform (10 mL), 1-(3-dimethylaminopropyl)-3-ethylcarbodiimide hydrochloride (1.10 g, 5.74 mmol) and dimethylaminopyridine (25.2 mg, 0.206 mmol) were added thereto at room temperature, and the mixture was stirred at room temperature for 3 hours. The compound 1 (2.34 g, 2.64 mmol). 1-(3-dimethylaminopropyl)-3-ethylcarbodiimide hydrochloride (0.55 g, 2.9 mmol), and dimethylaminopyridine (12.6 mg, 0.103 mmol) were added to the reaction solution at room temperature, and the mixture was stirred at room temperature for 3 hours. The reaction solution was purified by flash column chromatography to obtain a white solid. The obtained white solid was dissolved in ethyl acetate (2 mL) and hexane (40 mL) was added thereto. The solution was cooled to 0° C. under stirring and stirred for 1 hour. The produced crystals were filtered and washed with hexane to obtain a compound A-5 (1.31 g).

The $^1$H-NMR of the obtained compound A-5 is shown below.

$^1$H-NMR (CDCl$_3$): δ=7.99 (dd, 1H), 7.53 (dt, 1H), 7.33 (t, 1H), 7.04 (d, 1H), 6.43 (dd, 1H), 6.42 (dd, 1H), 6.14 (dd, 1H), 6.13 (dd, 1H), 5.89 (dd, 2H), 4A2-4.52 (m, 4H), 4.28-4.38 (m, 4H), 2.53 (t, 2H), 2.17-2.31 (m, 3H), 1.96-2.07 (m, 2H) 1.76-1.90 (m, 1.33-1.66 (m, 4H), 0.98-1.20 (m, 6H).

Example 6

A white solid compound A-6 represented by Formula A-6 was obtained according to the same procedure as in Example 1, except that 3-methoxyphenol was used instead of phenol.

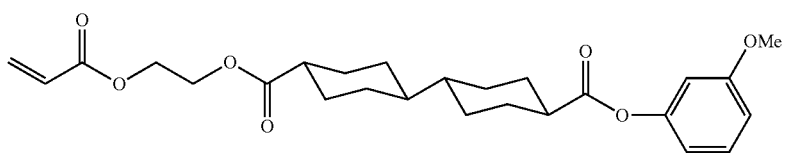

A-6

The $^1$H-NMR of the obtained compound A-6 is shown below.

$^1$H-NMR (CDCl$_3$): δ=7.26 (t, 1H), 6.78 (dd, 1H), 6.60-6.68 (m, 2H), 6.43 (dd, 1H), 6.16 (dd, 1H), 5.87 (dd, 1H), 4.29-4.39 (m, 4H), 3.78 (s, 3H), 2.46 (tt, 1H), 2.12-2.31 (m, 3H), 1.96-2.07 (n, 2H), 1.77-1.91 (m, 4H), 1.35-1.61 (m, 4H), 0.96-1.19 (m, 6H).

Example 7

A compound A-7 represented by Formula A-7 was synthesized according to the following synthesis scheme.

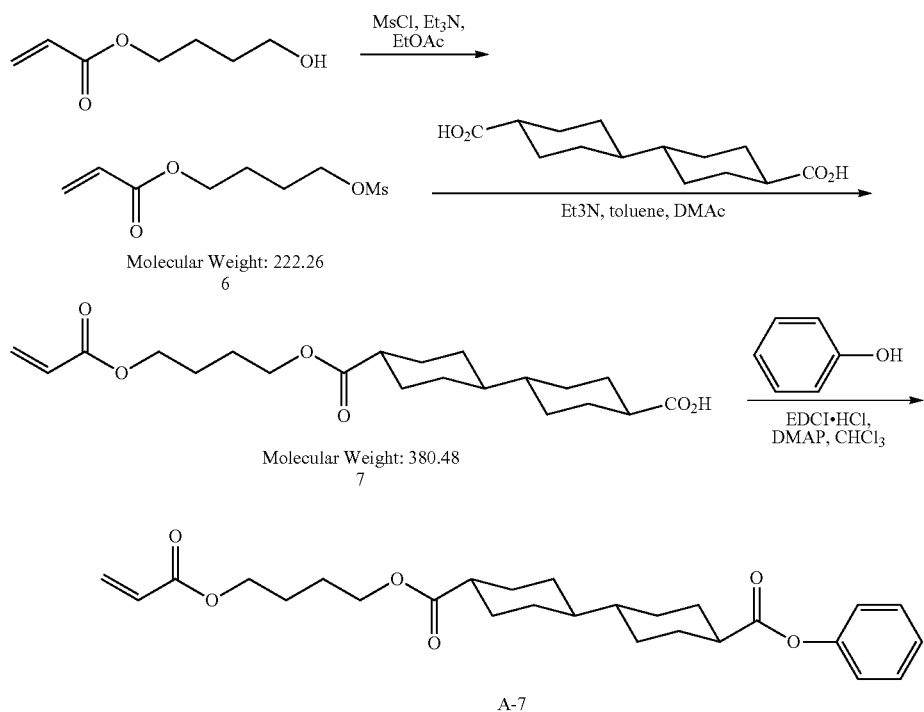

(1) Synthesis of Compound 6

4-Hydroxybutyl acrylate (50.0 g, 0.347 mol) and dibutylhydroxytoluene (190 mg, 0.862 mmol) were dissolved in ethyl acetate (250 mL), triethylamine (41.1 g, 0.406 mol) and methanesulfonic acid chloride (41.1 g, 0.406 mol) were added thereto under ice-cooling, and the mixture was stirred at room temperature for 5 hours. Water (125 mL) was added to the reaction solution and the mixture was extracted with ethyl acetate. The organic layer obtained by extraction was washed with saturated saline and mirabilite was added thereto. The obtained organic layer was filtered to recover the filtrate, dibutylhydroxytoluene (190 mg, 0.862 mmol) was then added thereto, and the solvent was evaporated under reduced pressure to obtain a compound 6 (73.7 g).

(2) Synthesis of Compound 7

The compound 6 (86.5 g, 0.389 mol) and dibutylhydroxytoluene (0.78 g, 3.5 mmol) were dissolved in a mixed solvent of toluene (180 mL) and dimethylacetamide (200 mL), bicyclohexyl-1,1'-dicarboxylic acid (90.0 g, 0.354 mol) and triethylamine (71.6 g, 0.708 mol) were added thereto at room temperature, and the mixture was stirred at 90° C. for 5 hours. The reaction solution was cooled to room temperature, a mixed solution of concentrated hydrochloric acid (23.4 g) and water (130 mL) was then added thereto, the temperature was then raised to 45° C., and the aqueous layer was removed therefrom. The obtained organic layer was washed with a mixed solution of sodium bicarbonate (13.5 g) and water (260 mL), and a mixed solution of sodium bicarbonate (2.7 g) and water (270 mL) in this order, and magnesium sulfate was added thereto. The obtained organic layer was filtered through Celite to recover the filtrate, dibutylhydroxytoluene (0.78 g, 3.5 mmol) was then added thereto, and the solvent was evaporated from the filtrate under reduced pressure. The obtained residue was dissolved in toluene (360 mL) and hexane (830 mL) was added thereto at 40° C. The solution was cooled to 5° C. under stirring and stirred for 30 minutes. The produced crystals were filtered and washed with hexane to obtain a compound 7 (28.4 g).

(3) Synthesis of Compound A-7

Phenol (1.00 g, 1.0.6 mmol) and the compound 6 (5.06 g, 13.3 mmol) were dissolved in chloroform (10 mL), 1-(3-dimethylaminopropyl)-3-ethylcarbodiimide hydrochloride (2.75 g, 14.3 mmol) and dimethylaminopyridine (64.9 mg, 0.531 mmol) were added thereto at room temperature, and the mixture was stirred at room temperature for 4 hours. The reaction solution was purified by flash column chromatography to obtain a white solid. The obtained white solid was dissolved in ethyl acetate (10 mL) and hexane (100 mL) was added thereto. The solution was cooled to 0° C. under stirring and stirred for 1 hour. The produced crystals were filtered and washed with hexane to obtain a compound A-7 (3.48 g).

The $^1$H-NMR of the obtained compound A-7 is shown below.

$^1$H-NMR (CDCl$_3$): δ=7.36 (t, 2H)), 7.24 (t, 1H), 7.06 (d, 2H), 6.42 (dd, 1H), 6.12 (dd, 1H), 5.83 (dd, 1H), 4.14 (dt, 4H), 2.44 (tt, 1H), 2.12-2.29 (m, 3H), 1.95-2.06 (at, 2H), 1.63-1.92 (m, 8H), 1.25-1.64 (m, 4H), 0.97-1.21 (m, 6H).

Example 8

A white solid compound A-8 represented by Formula A-8 was obtained according to the same procedure as in Example 7, except that compound 5 was used instead of phenol.

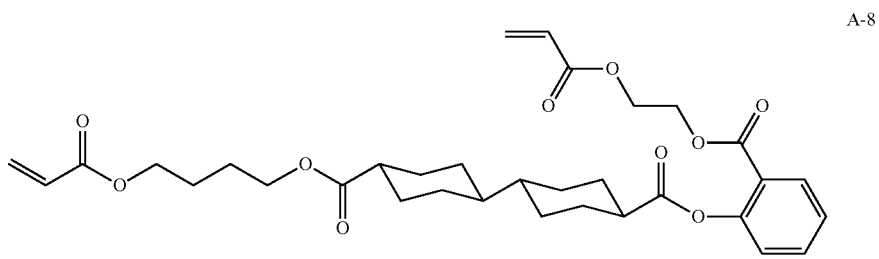 [SMILES: C=CC(=O)OCCCCOC(=O)C1CCC(C2CCC(C(=O)Oc3ccccc3C(=O)OCCOC(=O)C=C)CC2)CC1]

A-8

The $^1$H-NMR of the obtained compound A-8 is shown below.

$^1$H-NMR (CDCl$_3$): δ=7.99 (dd, 1H), 7.65 (dt, 1H), 7.33 (dt, 2H), 7.09 (dd, 1H), 6.44 (dd, 1H), 6.43 (dd, 1H), 6.16 (dd, 1H), 6.15 (dd, 1H), 5.87 (dd, 1H), 5.86 (dd, 1H), 4.44-4.52 (m, 4H), 4.14 (dt, 4H), 2.53 (tt, 1H), 2.17-2.29 (m, 3H), 1.96-2.06 (m, 2H), 1.69-1.92 (m, 8H), 1.25-1.64 (m, 4H), 0.96-1.20 (m, 6H).

Example 9

A white solid compound A-9 represented by Formula A-9 was obtained according to the same procedure as in Example 7, except that 1-naphthol was used instead of phenol.

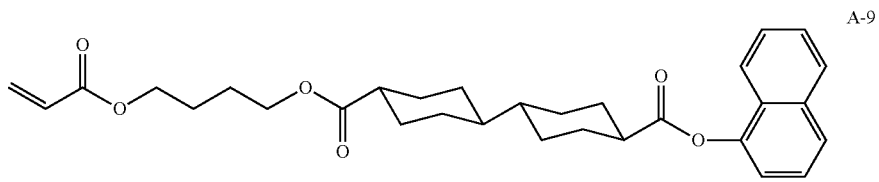 [SMILES: C=CC(=O)OCCCCOC(=O)C1CCC(C2CCC(C(=O)Oc3cccc4ccccc34)CC2)CC1]

A-9

The $^1$H-NMR of the obtained compound A-9 is shown below.

$^1$H-NMR (CDCl$_3$): δ=7.81-7.89 (m, 2H), 7.72 (d, 1H), 7.42-7.53 (m, 3H), 7.22 (dd, 1H), 6.42 (dd, 1H), 6.12 (dd, 1H), 5.83 (dd, 1H), 4.05-4.24 (m, 4H), 2.65 (tt, 1H), 2.14-2.38 (m, 3H), 1.59-2.04 (m, 10H), 1.28-1.50 (m, 4H), 0.93-1.28 (m, 6H).

Example 10

A compound A-10 represented by Formula A-10 was synthesized according to the following synthesis scheme.

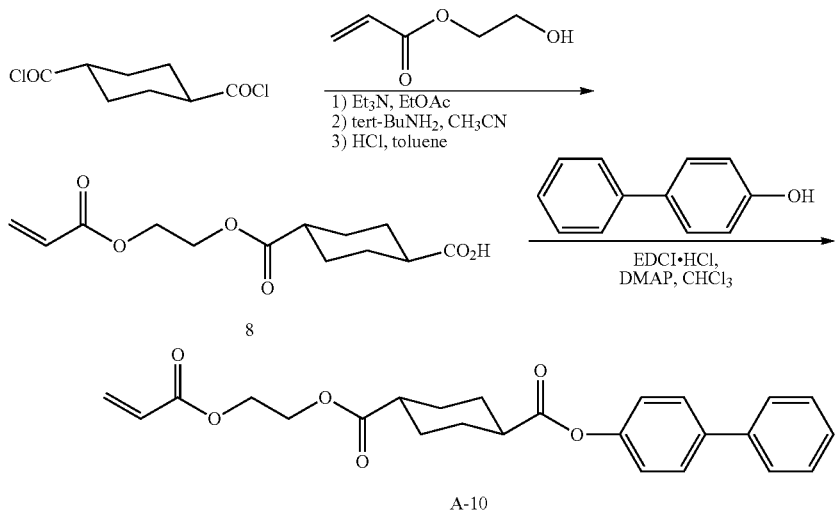

(1) Synthesis of Compound 8

1,4-Cyclohexyldicarboxylic acid dichloride (31.4 g, 0,150 mol) and dibutylhydroxytoluene (1.1 g, 5.0 mmol) were dissolved in ethyl acetate (160 mL), triethylamine (12.1 g, 0.120 mol) and 2-hydroxyethyl acrylate (11.6 g, 0.100 mol) were added thereto under ice-cooling, and the mixture was stirred at room temperature for 3 hours. A mixed solution of sodium bicarbonate (12.2 g) and water (120 mL), and 1-methylimidazole (8.0 g, 0.098 mol) were added to the reaction solution, the mixture was stirred at 40° C. for 1 hour, and the aqueous layer was then removed therefrom. The obtained organic layer was washed with 0.1 N hydrochloric acid (160 mL) and 5% saline (160 mL) in this order, and magnesium sulfate was added thereto. The obtained organic layer was filtered through Celite to recover the filtrate, dibutylhydroxytoluene (1.1 g, 5.0 mmol) was then added thereto, and the solvent was evaporated from the filtrate under reduced pressure. The obtained residue was dissolved in acetonitrile (310 mL) and tert-butylamine (5.78 g, 0,079 mol) was added thereto under ice-cooling. The solution was stirred for 1 hour, and the produced crystals were filtered and washed with acetonitrile.

Next, toluene (25 mL) and water (20 mL) were added to 10.0 g of the obtained crystals, a mixed solution of concentrated hydrochloric acid (3.3 g) and water (0.3 mL) was added thereto under ice-cooling, the mixture was stirred at room temperature for 30 minutes, and the aqueous layer was then removed therefrom. The obtained organic layer was washed with water (50 mL) and magnesium sulfate was added thereto. The obtained organic layer was filtered through Celite to recover the filtrate, dibutylhydroxytoluene (111 mg, 0.504 mmol) was then added thereto, and the solvent was evaporated from the filtrate under reduced pressure to obtain a compound 8 (7.25 g).

(2) Synthesis of A-1.0

4-Phenylphenol (1.34 g, 7.87 mmol) and the compound 8 (2.66 g, 9.85 mmol) were dissolved in chloroform (10 mL), 1-(3-dimethylaminopropyl)-3-ethylcarbodiimide hydrochloride (2.05 g, 10.7 mmol) and dimethylaminopyridine (48.1 mg, 0.394 mmol) were added thereto at room temperature, and the mixture was stirred at room temperature for 4 hours. The reaction solution was purified by flash column chromatography to obtain a white solid. The obtained white solid was dissolved in ethyl acetate (4 mL) and hexane (80 mL) was added thereto. The solution was cooled to 0° C. under stirring and stirred for 1 hour. The produced crystals were filtered and washed with hexane to obtain a compound A-10 (0.66 g).

The $^1$H-NMR of the obtained compound A-10 is shown below.

$^1$H-NMR (CDCl$_3$): δ=7.56 (t, 4H), 7.43 (t, 2H), 7.31-7.38 (n, 1H), 7.13 (d, 2H), 6.44 (dd, 1H), 6.15 (dd, 1H), 5.88 (dd, 1H), 4.33-4.41 (m, 4H), 2.56 (tt, 1H), 2. 38 (tt, 1H), 2.10-2.30 (m, 4H), 1.48-1.61 (m, 4H).

Example 11

A white solid compound A-11 represented by Formula A-11 was obtained according to the same procedure as in Example 10, except that 4-cyclohexylphenol was used instead of 4-phenylphenol.

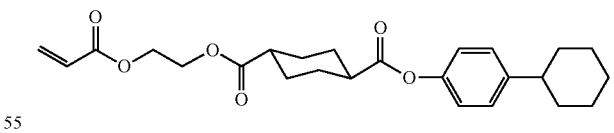

A-11

The $^1$H-NMR of the obtained compound A-11 is shown below.

$^1$H-NMR (CDCl$_3$): δ=7.19 (d, 2H), 6.96 (d, 2H), 6.42 (dd, 1H), 6.13 (dd, 1H), 5.83 (dd, 1H), 4.08-4.25 (m, 4H), 2.43-2.59 (m, 2H), 2.03-2.40 (m, 6H), 1.15-1.92 (m, 1H).

Example 12

A white solid compound A-12 represented by Formula A-12 was obtained according to the same procedure as in Example 7, except that 4-phenylphenol was used instead of phenol.

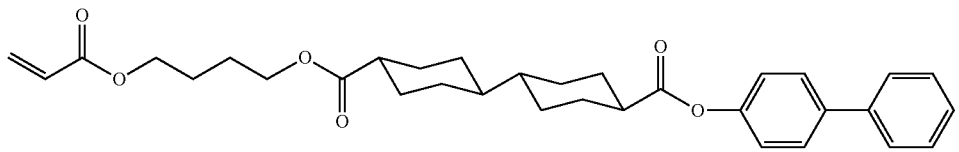

A-12

The of the obtained compound A-12 is shown below.
$^1$H-NMR (CDCl$_3$): δ=7.52-7.62 (m, 4H), 7.43 (t, 2H), 7.34 (tt, 1H), 7.13 (d, 2H), 6.41 (dd, 6.12 (dd, 1H), 5.82 (dd, 1H), 4.13 (dt, 4H), 2.48 (tt, 1H), 2.13-2.39 (m, 3H), 1.93-2.07 (m, 2H), 1.66-1.92 (m, 8H), 1.28-1.63 (m, 4H), 0.97-1.20 (m, 6H).

Example 13

A compound A-13 represented by Formula A-13 was synthesized according to the following synthesis scheme.

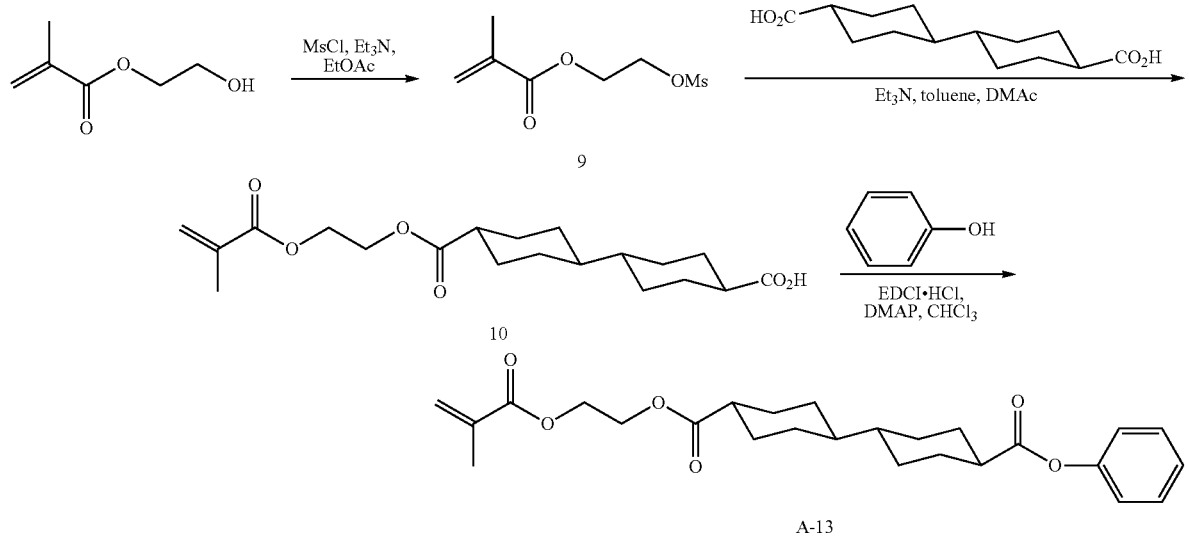

A-13

(1) Synthesis of Compound 9

2-Hydroxyethyl methacrylate (50.0 g, 0.384 mol) and dibutylhydroxytoluene (1.69 g, 7.67 mmol) were dissolved in ethyl acetate (250 mL), triethylamine (45.5 g, 0.450 mol) and methanesulfonic acid chloride (46.7 g, 0.407 mol) were added thereto under ice-cooling, and the mixture was stirred at room temperature fir 5 hours. Water (125 mL) was added to the reaction solution and the mixture was extracted with ethyl acetate. The organic layer obtained by extraction was washed with saturated saline and mirabilite was added thereto. The obtained organic layer was filtered to recover the filtrate, dibutylhydroxytoluene (0.34 g, 1.54 mmol) was then added thereto, and the solvent was evaporated under reduced pressure to obtain a compound 9 (82.6 g).

(2) Synthesis of Compound 10

The compound 9 (76.6 g, 0.368 mol) and dibutylhydroxytoluene (0.74 g, 3.4 mmol) were dissolved in a mixed solvent of toluene (170 mL) and dimethylacetamide (190 mL), bicyclohexyl-1,1'-dicarboxylic acid (85.0 g, 0.334 mol) and triethylamine (67.6 g, 0.668 mol) were added thereto at room temperature and the mixture was stirred at 90° C. for 5 hours. The reaction solution was cooled to room temperature, a mixed solution of concentrated hydrochloric acid (22.1 g) and water (120 mL) was then added thereto, the temperature was then raised to 45° C., and the aqueous layer was removed therefrom. The obtained organic layer was washed with a mixed solution of sodium bicarbonate (12.7 g) and water (240 mL), and a mixed solution of sodium bicarbonate (2.5 g) and water (250 mL) in this order, and magnesium sulfate was added thereto. The obtained organic layer was filtered through Celite to recover the filtrate, dibutylhydroxytoluene (95.7 g, 0.434 mmol) was then added thereto, and the solvent was evaporated from the filtrate under reduced pressure. The obtained residue was dissolved in toluene (340 mL) and hexane (630 mL) was added thereto at 40° C. The solution was cooled to 5° C. under stirring and stirred for 30 minutes. The produced crystals were filtered and washed with hexane to obtain a compound 10 (26.7 g).

(3) Synthesis of Compound A-13

Phenol (1.00 g, 10.6 mmol) and the compound 10 (4.87 g, 13.3 mmol) were dissolved in chloroform (1.0 mL), 1-(3-dimethylaminopropyl)-3-ethylcarbodiimide hydrochloride (2.75 g, 14.3 mmol) and dimethylaminopyridine (64.9 mg, 0.531 mmol) were added thereto at room temperature, and the mixture was stirred at room temperature for 4 hours. The reaction solution was purified by flash column chromatography to obtain a white solid. The obtained white solid was dissolved in chloroform (5 mL) and methanol (100 mL) was added thereto. The solution was cooled to 0° C. under stirring and stirred for 1 hour. The produced crystals were filtered and washed with methanol to obtain a compound A-13 (3.71 g).

The $^1$H-NMR of the obtained compound A-13 is shown below.
$^1$H-NMR (CDCl$_3$): δ=7.37 (t, 2H), 7.23 (t, 1H), 7.04 (d, 2H), 6.11 (s, 1H), 5.59 (s, 1H)), 4.27-4.39 (m, 4H), 2.43 (tt, 1H), 2.12-2.31 (m, 3H), 1.93-2.06 (m, 5H), 1.76-1.90 (m, 4H), 1.22-1.61 (m, 4H), 0.93-1.20 (m, 6H).

Example 14

A white solid compound A-14 represented by Formula A-14 was obtained according to the same procedure as in Example 10, except that 2-hydroxyethyl methacrylate was used instead of 2-hydroxyethyl acrylate.

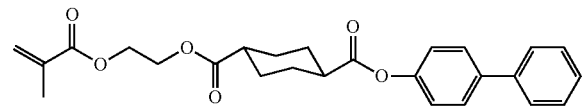

A-14

The $^1$H-NMR of the obtained compound. A-14 is shown below.

$^1$H-NMR (CDCl$_3$): δ=7.52-7.62 (m, 4H), 7.43 (t, 2H), 7.33 (t, 1H), 7.13 (d, 2H), 6.12 (s, 1H), 5.59 (s, 1H), 4.33 (br s, 4H), 2.52 (tt, 1H), 2.33 (tt, 1H), 2.09-2.28 (m, 4H), 1.95 (s, 3H), 1.46-1.69 (m, 4H).

Example 15

Synthesis Example (1)

A compound A-15 represented by Formula A-15 was synthesized according to the following synthesis scheme.

(1) Synthesis of Compound 11

The compound A-15 was dissolved in 2-(4-hydroxyphenyl)ethanol (50.0 g, 0.362 mol) and dimethylacetamide (340 mL), acryloyl chloride (36.0 g, 0.398 mol) was added thereto under ice-cooling, and the mixture was stirred at room temperature for 4 hours. The reaction solution was diluted with ethyl acetate (400 mL), 1 N hydrochloric acid (250 mL) was then added thereto, and the mixture was extracted with ethyl acetate. The organic layer obtained by the extraction was washed with saturated aqueous sodium bicarbonate and saturated saline in this order, and magnesium sulfate was added thereto. The obtained organic layer was filtered to recover the filtrate, dibutylhydroxytoluene (0.14 g, 0.64 mmol) was then added thereto, and the solvent was evaporated under reduced pressure to obtain a compound 10 (69.6 g).

(2) Synthesis of Compound 12

1,4-Cyclohexyldicarboxylic acid (55.0 g, 0.319 mol) was suspended in tetrahydrofuran (550 mL), methanesulfonyl chloride (20.2 g, 0.176 mol) and triethylamine (19.4 g, 0.192 mol) were added thereto under ice-cooling, and the mixture was stirred at room temperature for 1 hour. Dibutylhydroxytoluene (0.18 g, 0.82 mmol), dimethylaminopyridine (1.95 g, 16.0 mmol), and the compound 11 (30.7 g, 0.160 mol) were added to the reaction solution, triethylamine (19.4 g, 0,192 mol) was then added thereto under ice-cooling, and the mixture was stirred at room temperature for 2 hours. The reaction solution was filtered through Celite and diluted with ethyl acetate (300 mL), 1 N hydrochloric acid (100 mL) was then added thereto, and the mixture was extracted with ethyl acetate. The obtained organic layer was washed with saturated aqueous sodium bicarbonate and saturated saline in this order, and magnesium sulfate was added thereto. The obtained organic layer was filtered to recover the filtrate, dibutylhydroxytoluene (0.14 g, 0.64 mmol) was then added thereto, and the solvent was evaporated under reduced pressure. The obtained residue was dissolved in chloroform (130 mL) and hexane (260 mL) was added thereto. The solution was stirred for 1 hour, and the produced crystals were filtered and washed with hexane to obtain a compound 11 (29.8 g).

(3) Synthesis of Compound A-15

Phenol (0.94 g, 10 mmol) and compound 11 (3.46 g, 9.99 mmol) were dissolved in chloroform (15 mL), 1-(3-dimethylaminopropyl)-3-ethylcarbodiimide hydrochloride (2.30 g, 12.0 mmol) and dimethylaminopyridine (0.06 g, 0.5 mmol) were added thereto at room temperature, and the mixture was stirred at room temperature for 2 hours. The reaction solution was purified by flash column chromatography to obtain a white solid. The obtained white solid was dissolved in ethyl acetate (15 mL) and methanol (50 mL) was added thereto. The solution was stirred for 1 hour, and the produced crystals were filtered and washed with methanol to obtain a compound A-15 (2.60 g).

The $^1$H-NMR of the obtained compound A-15 is shown below.

$^1$H-NMR (CDCl$_3$): δ=7.38 (t, 2H), 7.21-7.24 (m, 3H), 7.08 (d, 2H), 7.02 (d, 2H), 6.39 (d, 1H), 6.12 (dd, 1H), 5.81

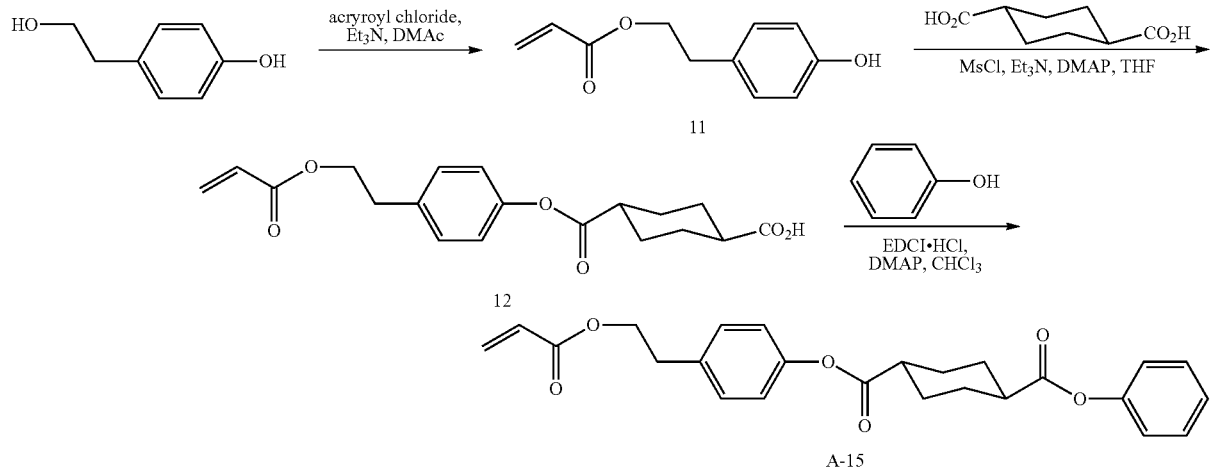

(d, 1H), 4.36 (t, 2H), 2.98 (t, 2H), 2.68-2.50 (m, 2H), 2.18-2.37 (m, 4H), 1.58-1.78 (3n, 4H).

Synthesis Example (2)

A compound A-15 represented by Formula A-15 was synthesized according to the following synthesis scheme.

(2) Synthesis of Compound 12A 1,4-Cyclohexyldicarboxylic acid dichloride (79.9 g, 0.38 mol) was dissolved in ethyl acetate (89 mL) and tetrahydrofuran (194 mL), and cooled by setting the external temperature to 5° C., and a 67% solution of phenol (27.7 g, 0.294 mol) in THF was added thereto. Triethylamine (35.7 g, 0.35 mol) was added dropwise thereto, and the mixture

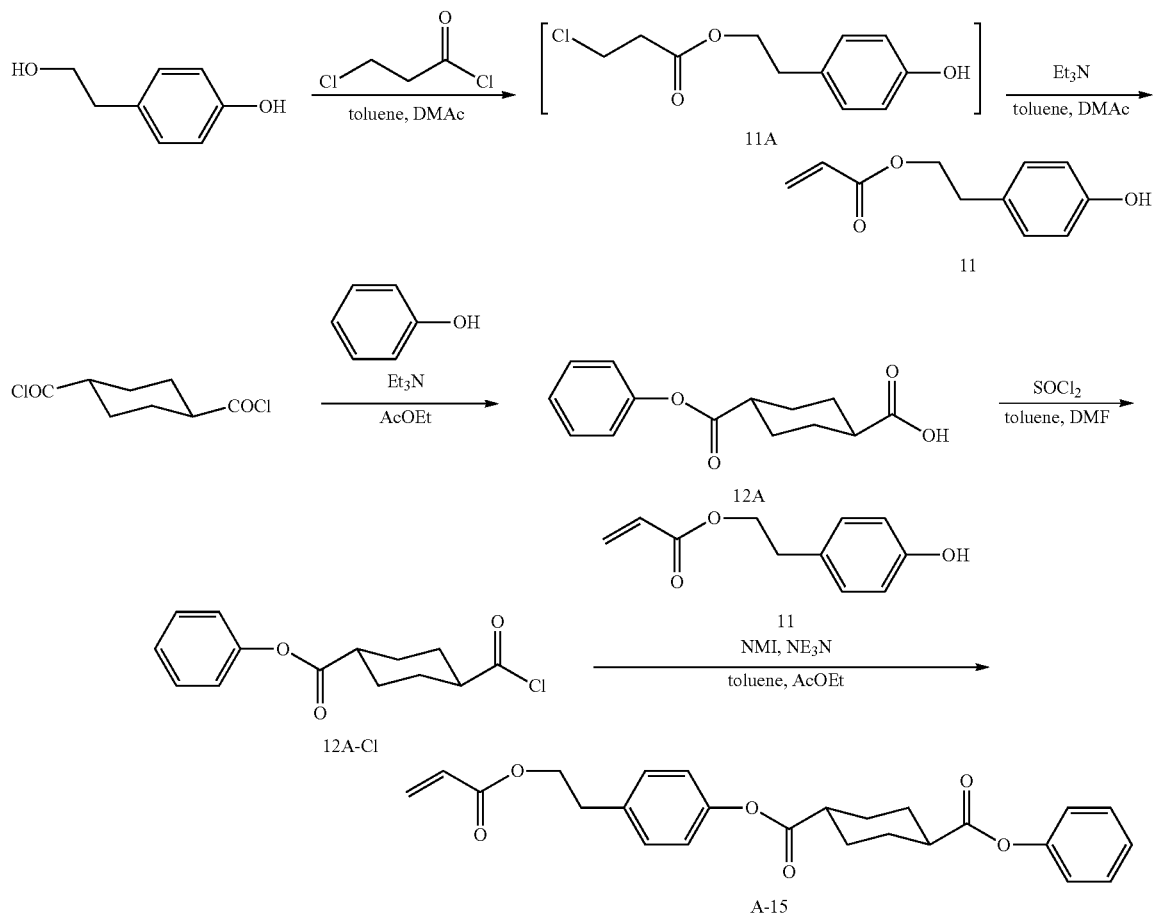

(1) Synthesis of Compound 11

2-(4-Hydroxyphenyl)ethanol (19.3 g, 0.14 mol) was dissolved in toluene (80 mL) and dimethylacetamide (24 mL) and heated to 60° C., and 3-chloropropionyl chloride (17.8 g, 0.14 mol) was added dropwise thereto, and the mixture was reacted at 60° C. to 70° C. for 2 hours. 2,6-Di-tert-butyl-p-cresol (0.15 g), triethylamine (42.5 g, 0.42 mol) was added dropwise thereto, and the mixture was then reacted at 60° C. to 70° C. for 2 hours. After completion of the reaction, the internal temperature was lowered to 25° C. or lower, and water (51 mL) and concentrated hydrochloric acid (16 g) were added to mixture to perform a liquid separation operation. Water (68 mL) was added to the organic layer obtained by the extraction to perform a liquid separation operation again, thereby obtaining an organic layer. 2,6-Di-tert-butyl-p-cresol (0.3 g) was added to the organic layer and toluene was evaporated under reduced pressure. Further, toluene (42 g) was added to the residue, and the mixture was evaporated under reduced pressure again to obtain a compound 11 (23 g).

was reacted at an internal temperature of 5° C. to 15° C. for 0.5 hours, After completion of the reaction, water (29 mL) was added dropwise, and then a mixed solution of water (76 mL) and a 40% aqueous sodium hydroxide solution (62 g) was added dropwise thereto. Then, the mixture was reacted at an internal temperature of 15° C. to 25° C. for 0.5 hours, N-methylimidazole (18 g) was then added dropwise thereto, and the mixture was reacted at an internal temperature of 35° C. to 40° C. for another 1 hour. Then, acetic acid (2.7 g) was added dropwise thereto to perform a liquid separation operation. Next, water (58 mL) and concentrated hydrochloric acid (17.7 g) were added to the organic layer to perform a liquid separation operation. Finally, water (133 mL) and salt (2.9 g) were added thereto, and the liquid separation operation was performed to extract the organic layer. Toluene (70 mL) was added to this organic layer, followed by performing evaporation under reduced pressure, and toluene (70 mL) was further added thereto, followed by further performing evaporation reduced pressure. Toluene (388 mL) was added thereto, the mixture was filtered under reduced pressure, washed with a mixed solution of cyclohexane (29 mL) and isopropanol (7.5 mL), and dried at room temperature overnight to obtain a compound 12A (33 g).

(3) Synthesis of Compound A-15

The compound 12A (28.4 g, 0.114 mol) was dissolved in toluene (59 mL) and dimethylformamide (22 mL), thionyl chloride (15.1 g, 0.127 mol) was added dropwise thereto so that the internal temperature reached 20° C. to 40° C., and the mixture was reacted at an internal temperature of 30° C. to 40° C. for 1 hour. Thereafter, the mixture was left to stand to remove the underlayer, ethyl acetate (91 mL) was then added to the residue, and the internal temperature was lowered to 5° C. N-methylimidazole (1.9 g) was added dropwise to the mixture and 2,6-di-tert-butyl-p-cresol (0.25 g) was added thereto. A solution of the compound 11 (39.5 g, 0.104 mol) in ethyl acetate (30 mL) was added dropwise to the reaction solution, triethylamine (21.1 g, 0.21 mol) was then added dropwise thereto, and the mixture was reacted at an internal temperature of 30° C. to 40° C. for 2 hours. Then, methanol (5.7 mL) was added dropwise thereto, the mixture was stirred for 15 to 30 minutes, and subsequently, water (34 mL) and ethyl acetate (28 mL) were added thereto to perform dust removal filtration. Water (165 mL) and concentrated hydrochloric acid (1.4 g) were added to the residue to perform a liquid separation operation. Next, water (180 mL) and a salt (20 g) were added to the extracted organic layer to perform a liquid separation operation, thereby extracting the organic layer. A mixed solution of methanol (400 mL) and water (140 mL) was added dropwise to the obtained organic layer, the internal temperature was lowered to 5° C., and the mixture was stirred for 0.5 hours and then filtered under reduced pressure to obtain a compound A-15 (35 g).

Example 16

A white solid compound A-16 represented by Formula A-16 was obtained according to the same procedure as in Example 15, except that methacryloyl chloride was used instead of acryloyl chloride.

A-16

The $^1$H-NMR of the obtained compound A-16 is shown below.

$^1$H-NMR (CDCl$_3$): δ=7.4 (t, 2H), 7.2-7.3 (m, 3H), 7.1 (d, 2H), 7.0 (d, 2H), 6.1 (s, 1H), 5.55 (s, 1H), 4.3 (t, 2H), 3.0 (t, 2H), 2.5-2.65 (m, 2H), 2.3 (m, 4H), 1.9 (s, 3H), 1.6-1.7 (m, 4H)

Example 17

A white solid compound A-17 represented by Formula A-17 was obtained according to the same procedure as in Example 15, except that o-methoxyphenol was used instead of phenol.

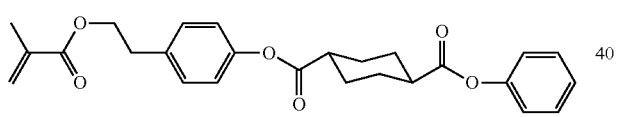

A-17

The $^1$H-NMR of the obtained compound A-17 is shown below.

$^1$H-NMR (CDCl$_3$): δ=7.2-7.3 (m, 3H), 6.9-7.1 (m, 5H), 6.4 (d, 1H), 6.1 (dd, 1H), 5.80 (d, 1H), 4.35 (t, 2H), 3.8 (s, 3H), 3.0 (t, 3H), 2.5-2.7 (m, 2H), 2.2-2.4 (m, 4H), 1.6-1.8 (m, 4H).

Comparative Example 1

A compound B-1 represented by Formula B-1 was synthesized according to the description in JP2010-100609A.

B-1

Comparative Example 2

A compound B-2 represented by Formula B-2 was synthesized according to the description in JP2011-246365A.

B-2

Comparative Example 3

A compound B-3 represented by Formula B-3 was synthesized according to the description in JP2018-77465A.

B-3

Comparative Example 4

A compound B-4 represented by Formula B-4 was synthesized according to the description of WO2012/002140A.

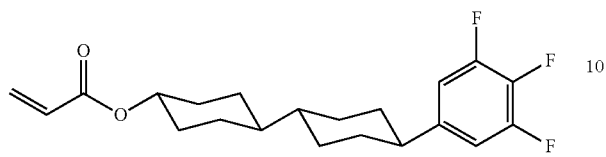

B-4

Comparative Example 5

A compound B-5 represented by Formula B-5 was synthesized according to the description in JP2015-166887A.

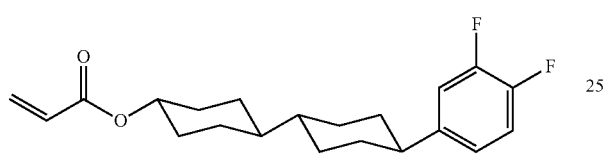

B-5

Comparative Example 6

A compound B-6 represented by Formula B-6 was synthesized according to the description in JP2013-152439A.

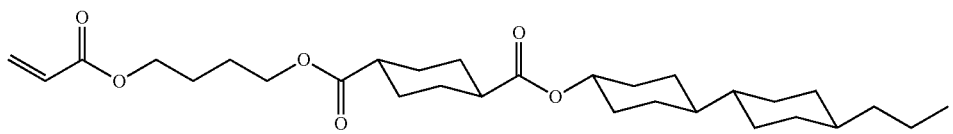

B-6

Comparative Example 7

A compound B-7 represented by Formula B-7 was synthesized according to the description in JP2016-126941A.

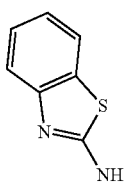
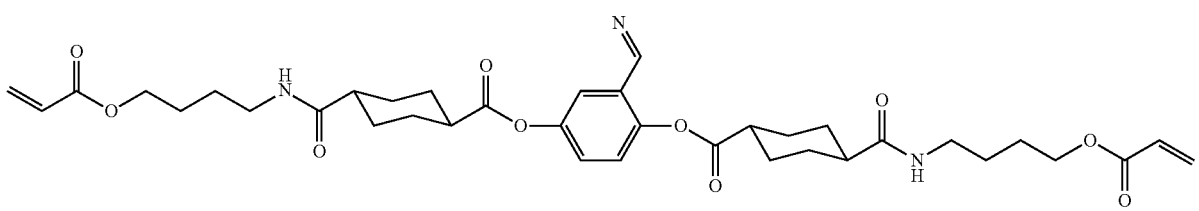

B-7

[Manufacture of Optical Film]

<Manufacture of Substrate with Alignment Film>

The following coating liquid for forming an alignment film was applied onto a glass substrate that had been washed, using a #5 bar coater, and the glass substrate was dried with hot air at 100° C. for 120 seconds and then subjected to a rubbing treatment to manufacture a substrate with an alignment film.

| (Coating Liquid for Forming Alignment Film) | |
|---|---|
| Polyvinyl alcohol (PVA 203 manufactured by Kuraray Co., Ltd.) | 2.0 parts by mass |
| Water | 98.0 parts by mass |

<Formation of Positive A-Plate>

The following composition was applied onto a substrate with an alignment film by a spin coating method. The coating film formed on the substrate with an alignment film was heated to 150° C. with hot air and then cooled to 105° C., and the coating film was irradiated with ultraviolet rays at 10 mJ/cm² at a wavelength of 365 nm in a nitrogen atmosphere using a high-pressure mercury lamp and subsequently irradiated with ultraviolet rays at 500 mJ/cm² under heating to 120° C. to fix the alignment of the liquid crystal compound, thereby manufacturing an optical film including a positive A-plate.

| (Composition) | |
|---|---|
| The following polymerizable liquid crystal compound L-1 | 20.00 parts by mass |
| The following polymerizable liquid crystal compound L-2 | 40.00 parts by mass |
| The following polymerizable liquid crystal compound L-3 | 40.00 parts by mass |
| A compound described in Table 4 below | 8.00 parts by mass |
| The following polymerization initiator PI-1 | 0.50 parts by mass |
| The leveling agent T-1 | 0.20 parts by mass |
| Cyclopentanone | 235.00 parts by mass |

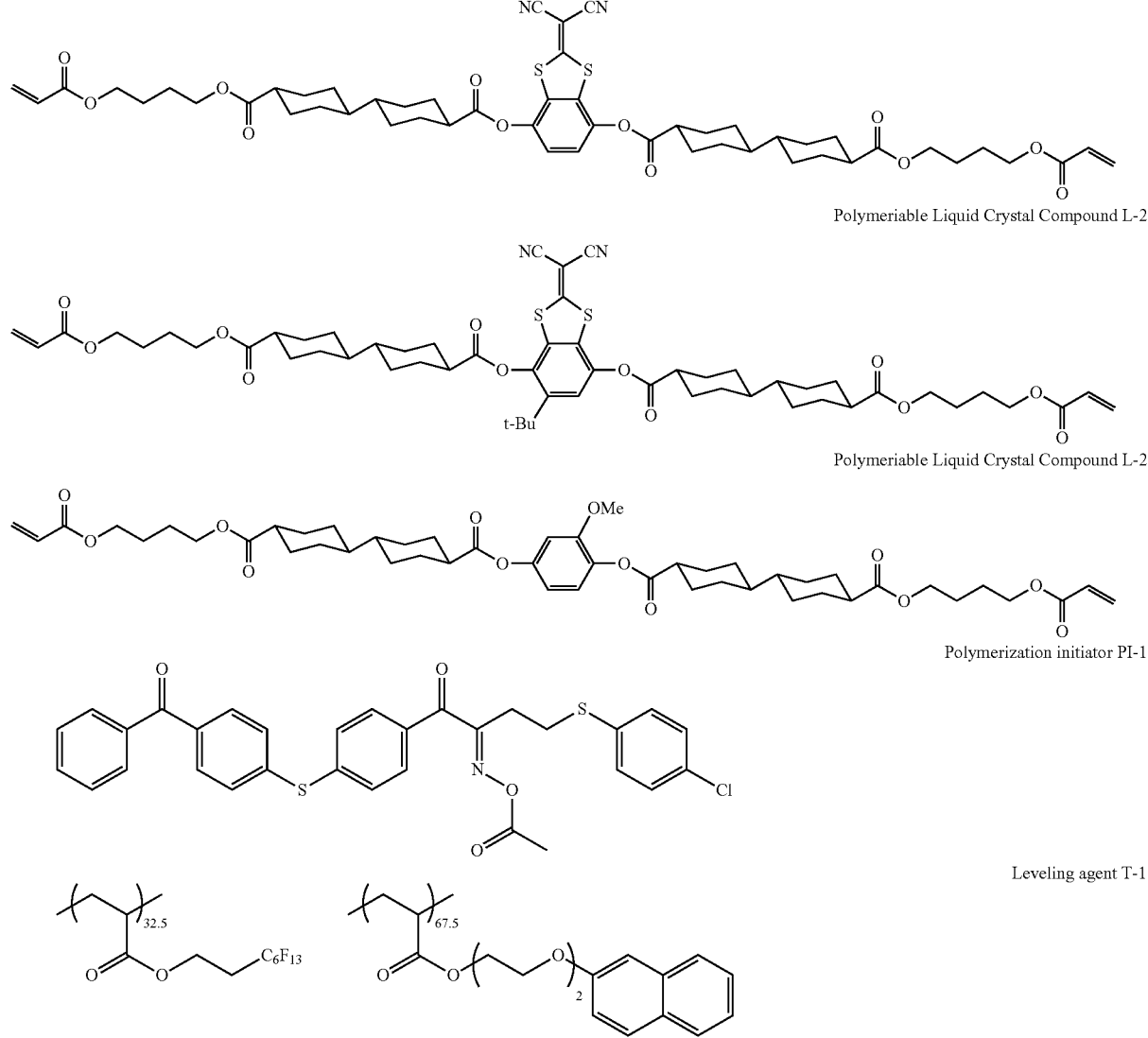

[Evaluation]
<Moisture-Heat Resistance>

A glass plate and a coated surface of the manufactured positive A-plate were bonded together using a pressure sensitive adhesive (SK-2057, manufactured by Soken Chemical & Engineering Co, Ltd.), the substrate with an alignment film was peeled from the glass plate, only the positive A-plate was transferred onto the glass plate and compared with the same sample, which was, however, not exposed to a high temperature and a high humidity, after a lapse of 136 hours at 100° C. and a humidity of 95%, and thus, a Re change rate was evaluated. In Table 4 below, "A" represents a Re change rate of less than 5%, "B" represents a Re change rate of 5% or more and less than 10%, and "C" represents a Re change rate of 10% or more.

<Measurement of Tilt Angle>

The tilt angle refers to as a value obtained by measurement of the positive A-plate on the manufactured substrate with an alignment film as it was, using light at a wavelength of 550 nm, with AxoScan OPMF-1 (manufactured by Opto Science, Inc.). In Table 4 below, "A" represents a tilt angle of less than 7.0°, "B" represents a tilt angle of 7.0° or more and less than 9.3°, "C" represents a tilt angle of 9.3° or more and less than 10.0°, and "D" represents a tilt angle of 10.0° or more.

TABLE 4

| Table 4 | Compound | Evaluation | |
|---|---|---|---|
| | | Moisture-heat resistance | Tilt angle |
| Example 1 | A-1 | B | A |
| Example 2 | A-2 | B | A |
| Example 3 | A-3 | B | A |
| Example 4 | A-4 | B | A |
| Example 5 | A-5 | A | A |
| Example 6 | A-6 | B | A |
| Example 7 | A-7 | B | B |
| Example 8 | A-8 | A | B |
| Example 9 | A-9 | B | B |
| Example 10 | A-10 | B | B |
| Example 11 | A-11 | B | C |
| Example 12 | A-12 | B | C |
| Example 13 | A-13 | B | A |
| Example 14 | A-14 | B | A |
| Example 15 | A-15 | B | B |
| Example 16 | A-16 | B | A |
| Example 17 | A-17 | B | B |
| Comparative Example 1 | B-1 | B | D |
| Comparative Example 2 | B-2 | B | D |
| Comparative Example 3 | B-3 | C | D |
| Comparative Example 4 | B-4 | B | D |
| Comparative Example 5 | B-5 | B | D |
| Comparative Example 6 | B-6 | B | D |
| Comparative Example 7 | B-7 | B | D |

From the results shown in Table 4 above, it was found that in a case where compounds B-1 to B-7 not corresponding to Formula (I) were used, the tilt angles of the liquid crystal molecules were 10° or more (Comparative Examples 1 to 7).

In contrast, it was found that in a case where compounds A-1 to A-14 not corresponding to Formula (1) were used, the tilt angles of the liquid crystal molecules were smaller (Examples 1 to 17).

In particular, from the comparison results of Examples 1 and 3 to 6 and the comparison results of Examples 7 and 8, it was found that in a case where $A^2$ in Formula (I) is an aromatic ring having a substituent R, the substituent R is a substituent represented by -Z-Sp-P and the moisture-heat resistance is improved.

Furthermore, it was found that in a case where Sp in Formula (1) is a linear or branched alkylene group having 1 to 3 carbon atoms or in a case where m in Formula (I) is 0, the tilt angles of the liquid crystal molecules are smaller.

In addition, from the comparison between Example 10 and Example 14, it was found that in a case where the compound (I) and the polymerizable liquid crystal compound had different polymerizable groups, the tilt angles of the liquid crystal molecules are smaller.

Examples 18 and 19

[Manufacture of Optical Film]
<Manufacture of Substrate with Alignment Film>

The following coating liquid for forming an alignment film was applied onto a glass substrate that had been washed, using a #5 bar coater, and the glass substrate was dried with hot air at 100° C. for 120 seconds and then subjected to a rubbing treatment to manufacture a substrate with an alignment film.

(Coating Liquid for Forming Alignment Film)

| | |
|---|---|
| Polyvinyl alcohol (PVA 203 manufactured by Kuraray Co., Ltd.) | 2.0 parts by mass |
| Water | 98.0 parts by mass |

<Formation of Positive A-Plate>

The following composition was applied onto a substrate with an alignment film by a spin coating method. The coating film formed on the substrate with an alignment film was heated to 150° C. with hot air and then cooled to 1.05° C., and the coating film was irradiated with ultraviolet rays at 10 mJ/cm$^2$ at a wavelength of 365 nm in a nitrogen atmosphere using a high-pressure mercury lamp and subsequently irradiated with ultraviolet rays at 500 mJ/cm$^2$ under heating to 120° C. to fix the alignment of the liquid crystal compound, thereby manufacturing an optical film including a positive A-plate.

(Composition)

| | |
|---|---|
| The following polymerizable liquid crystal compound L-1 | 20.00 parts by mass |
| The following polymerizable liquid crystal compound L-2 | 40.00 parts by mass |
| The following polymerizable liquid crystal compound L-13 | 40.00 parts by mass |
| A compound described in Table 5 below | 8.00 parts by mass |
| The polymerization initiator PI-1 | 0.50 parts by mass |
| The leveling agent T-1 | 0.20 parts by mass |
| Cyclopentanone | 235.00 parts by mass |

Polymerizable Liquid Crystal Compound L-1

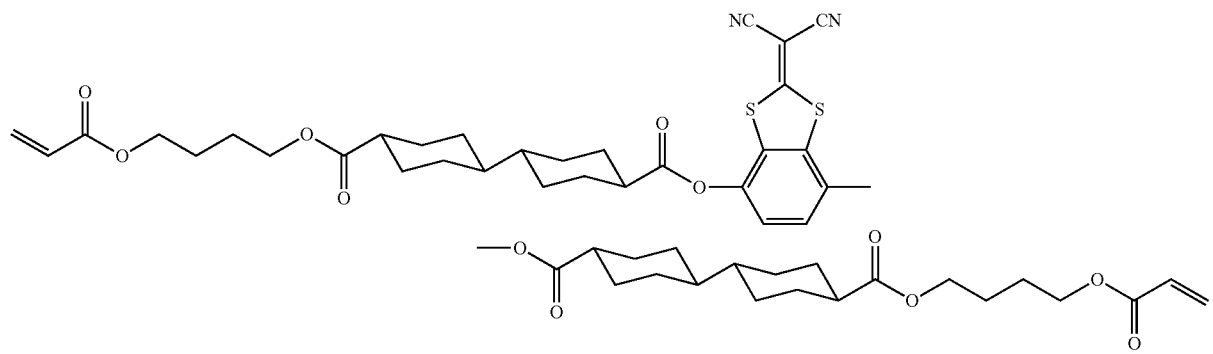

Polymerizable Liquid Crystal Compound L-2

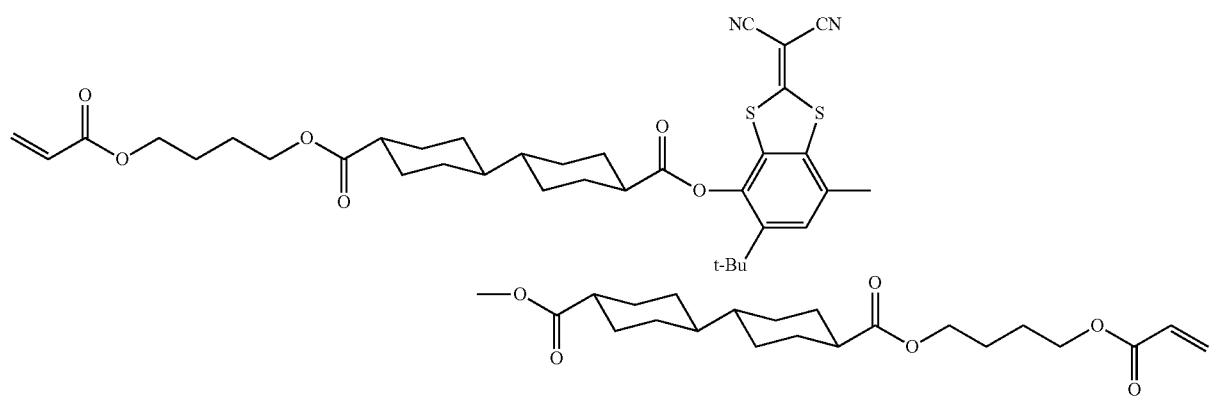

Polymerizable Liquid Crystal Compound L-13

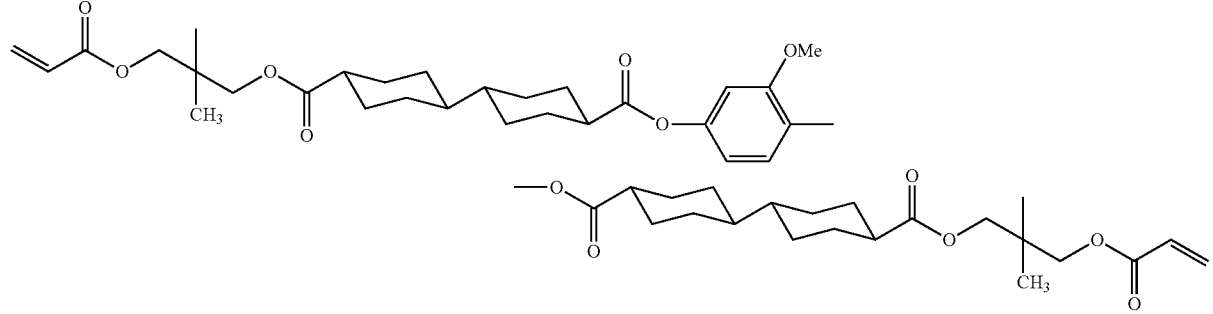

For the optical films manufactured in Examples 18 and 19, the tilt angle of the positive A-plate on the substrate with the alignment film was measured by the above-mentioned method. The results are shown in Table 5 below. Further, in Table 5 below, "A" represents a tilt angle of less than 7.0°.

TABLE 5

| Table 5 | Compound | Evaluation Tilt angle |
|---|---|---|
| Example 18 | A-1 | A |
| Example 19 | A-13 | A |

Examples 20 and 21

An optical film including a positive A-plate was prepared in the same manner as in Example 18, except that the method for forming a positive A-plate was changed to involve the method and the composition shown below.

<Formation of Positive A-Plate>

The following composition was applied onto a substrate with an alignment film by a spin coating method. The coating film formed on the substrate with an alignment film was heated to 150° C. with hot air and then cooled to 105° C., and the coating film was irradiated with ultraviolet rays at 10 mJ/cm² at a wavelength of 365 nm in a nitrogen atmosphere using a high-pressure mercury lamp and subsequently irradiated with ultraviolet rays at 500 mJ/cm² under heating to 120° C. to fix the alignment of the liquid crystal compound, thereby manufacturing an optical film including a positive A-plate.

| (Composition) | |
|---|---|
| The polymerizable liquid crystal compound L-1 | 20.00 parts by mass |
| The polymerizable liquid crystal compound L-2 | 40.00 parts by mass |
| The following polymerizable liquid crystal compound L-14 | 20.00 parts by mass |

-continued

| (Composition) | |
|---|---|
| The following polymerizable liquid crystal compound L-15 | 20.00 parts by mass |
| A compound described in Table 6 below | 8.00 parts by mass |
| The polymerization initiator PI-1 | 0.50 parts by mass |
| The leveling agent T-1 | 0.20 parts by mass |
| Cyclopentanone | 235.00 parts by mass | coating film formed on the substrate with an alignment film was heated to 150° C. with hot air and then cooled to 60° C., and the coating film was irradiated with ultraviolet rays at 10 mJ/cm² at a wavelength of 365 nm in a nitrogen atmosphere using a high-pressure mercury lamp and subsequently irradiated with ultraviolet rays at 500 mJ/cm² under heating to 120° C. to fix the alignment of the liquid crystal compound, thereby manufacturing an optical film including a positive A-plate.

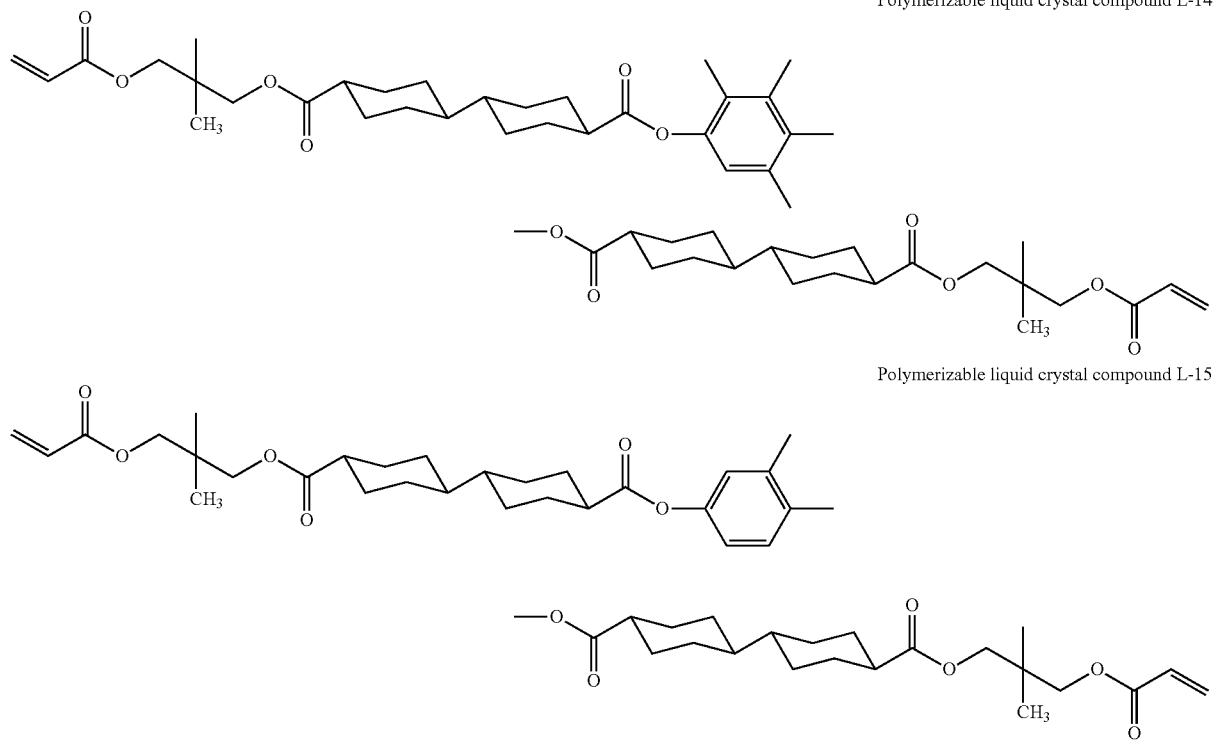

Polymerizable liquid crystal compound L-14

Polymerizable liquid crystal compound L-15

For the optical films manufactured in Examples 20 and 21, the tilt angle of the positive A-plate on the substrate with the alignment film was measured by the above-mentioned method. The results are shown in Table 6 below. In Table 6 below, "A" represents a tilt angle of less than 7.0°.

TABLE 6

| Table 6 | Compound | Evaluation Tilt angle |
|---|---|---|
| Example 20 | A-1 | A |
| Example 21 | A-13 | A |

Examples 22 to 26 and Comparative Examples 8 and 9

An optical film including a positive A-plate was prepared in the same manner as in Example 18, except that the method for forming a positive A-plate was changed to involve the method and the composition shown below.

<Formation of Positive A-Plate>

The following composition was applied onto a substrate with an alignment film by a spin coating method. The

| (Composition) | |
|---|---|
| The following polymerizable liquid crystal compound L-4 | 46.00 parts by mass |
| The following polymerizable liquid crystal compound L-5 | 46.00 parts by mass |
| A compound described in Table 7 below | 8.00 parts by mass |
| The polymerization initiator PI-1 | 0.50 parts by mass |
| The leveling agent T-1 | 0.20 parts by mass |
| Cyclopentanone | 235.00 parts by mass |

Furthermore, a group adjacent to the acryloyloxy group in Structural Formulae of the polymerizable liquid crystal compound L-4 and the polymerizable liquid crystal compound L-5 shown below represents a propylene group (a group obtained by substituting a methyl group with an ethylene group), and the polymerizable liquid crystal compounds L-4 and L-5 each represent a mixture of position isomers having different positions of the methyl groups.

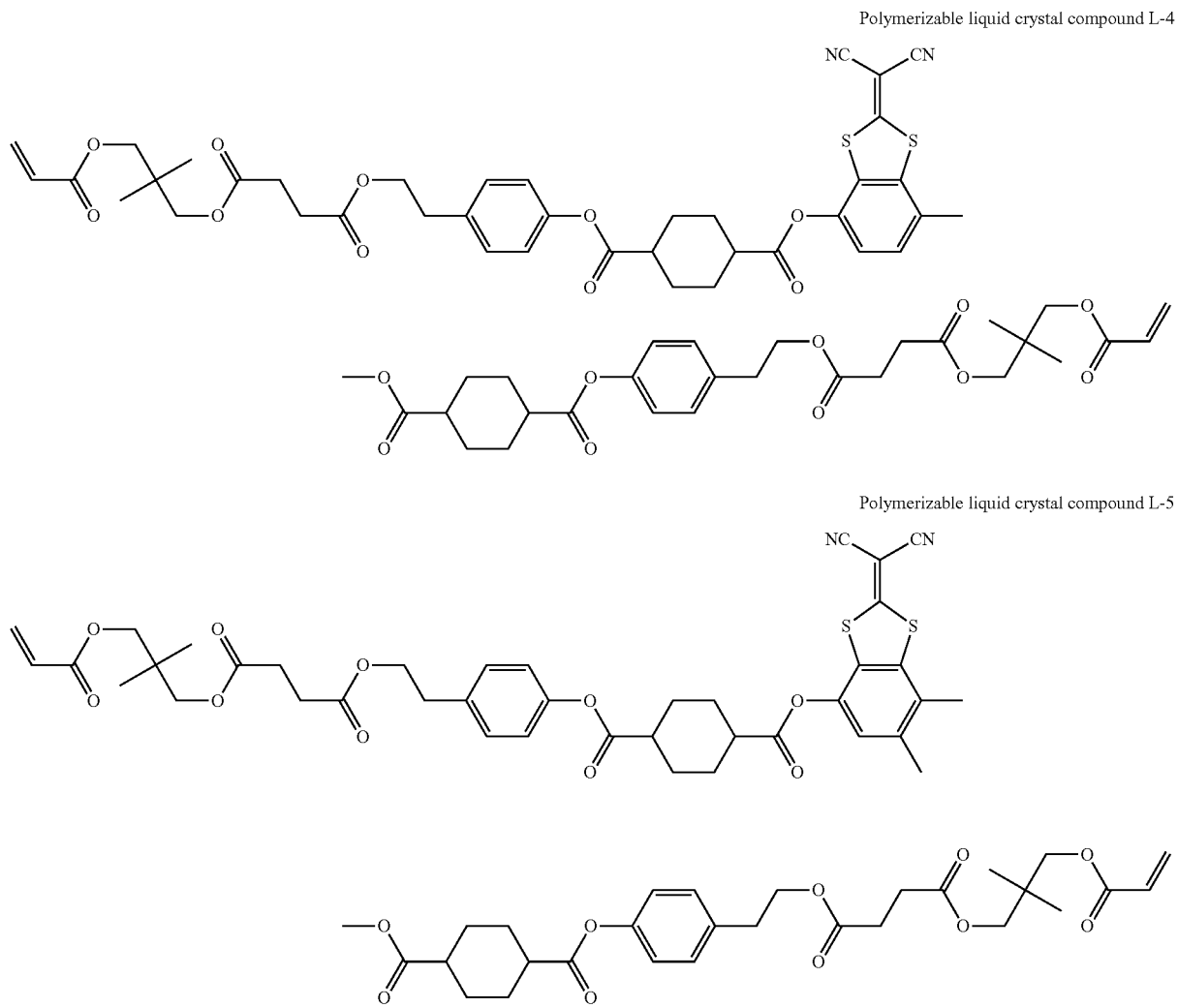

Polymerizable liquid crystal compound L-4

Polymerizable liquid crystal compound L-5

For the optical films manufactured in Examples 22 to 26, and Comparative Examples 8 and 9, the tilt angle of the positive A-plate on the substrate with an alignment film was measured by the above-mentioned method. The results are shown in Table 7 below. Further, in Table 7 below, "A" represents a tilt angle of less than 7.0°, "B" represents a tilt angle of 7.0° or more and less than 9.3°, and "D" represents a tilt angle of 10.0° or more.

TABLE 7

| Table 7 | Compound | Evaluation Tilt angle |
|---|---|---|
| Example 22 | A-1 | A |
| Example 23 | A-9 | A |

TABLE 7-continued

| Table 7 | Compound | Evaluation Tilt angle |
|---|---|---|
| Example 24 | A-13 | A |
| Example 25 | A-15 | A |
| Example 26 | O-3 | B |
| Comparative Example 8 | B-1 | D |
| Comparative Example 9 | B-6 | D |

In Table 7 above, the structures of compound A-1 and the like are as shown in Example 1 and the like, and the structure of a compound O-3 is as shown below.

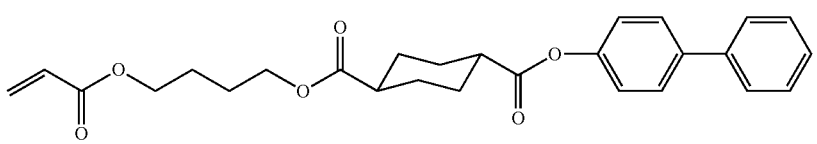 [SMILES: C=CC(=O)OCCCCOC(=O)C1CCC(C(=O)Oc2ccc(-c3ccccc3)cc2)CC1]

Examples 27 to 61 and Comparative Examples 10 to 16

An optical film including a positive A-plate was prepared in the same manner as in Example 18, except that the method for forming a positive A-plate was changed to involve the method and the composition shown below.
<Formation of Positive A-Plate>
An optical film including a positive A-plate was prepared in the same manner as in Example 22, except that the temperature at which the coating film was irradiated with ultraviolet rays using the following composition was 35° C. lower than the phase transition temperature between a smectic phase and a nematic phase of the polymerizable liquid crystal compound in Table 8 below.

| (Composition) | |
|---|---|
| Polymerizable liquid crystal compound L shown in Table 8 below | 92.00 parts by mass |
| A compound described in Table 8 below | 8.00 parts by mass |
| The polymerization initiator PI-1 | 0.50 parts by mass |
| The leveling agent T-1 | 0.20 parts by mass |
| Cyclopentanone | 235.00 parts by mass |

For the optical films manufactured in Examples 27 to 61 and Comparative Examples 10 to 16, the tilt angle of the positive A-plate on the substrate with the alignment film was measured by the above-mentioned method. The results are shown in Table 8 below. Further, in Table 8 below, "A" represents a tilt angle of less than 7.0°, "B" represents a tilt angle of 7.0° or more and less than 9.3°, "C" represents a tilt angle of 9.3° or more and less than 10.0°, and "D" represents a tilt angle of 10.0° or more.

TABLE 8

| Table 8 | Polymerizable liquid crystal compound | Compound | Evaluation Tilt angle |
|---|---|---|---|
| Example 27 | L-6 | A-1 | B |
| Example 28 | L-6 | A-10 | B |
| Example 29 | L-6 | A-15 | B |

TABLE 8-continued

| Table 8 | Polymerizable liquid crystal compound | Compound | Evaluation Tilt angle |
|---|---|---|---|
| Example 30 | L-6 | O-3 | B |
| Example 31 | L-6 | O-5 | B |
| Example 32 | L-7 | A-1 | B |
| Example 33 | L-7 | A-10 | B |
| Example 34 | L-7 | A-15 | B |
| Example 35 | L-7 | O-3 | B |
| Example 36 | L-7 | O-5 | B |
| Example 37 | L-8 | A-1 | B |
| Example 38 | L-8 | A-10 | B |
| Example 39 | L-8 | A-15 | B |
| Example 40 | L-8 | O-3 | B |
| Example 41 | L-8 | O-5 | B |
| Example 42 | L-9 | A-1 | B |
| Example 43 | L-9 | A-10 | B |
| Example 44 | L-9 | A-15 | B |
| Example 45 | L-9 | O-3 | B |
| Example 46 | L-9 | O-5 | B |
| Example 47 | L-10 | A-1 | B |
| Example 48 | L-10 | A-10 | B |
| Example 49 | L-10 | A-15 | B |
| Example 50 | L-10 | O-3 | B |
| Example 51 | L-10 | O-5 | B |
| Example 52 | L-11 | A-1 | B |
| Example 53 | L-11 | A-10 | B |
| Example 54 | L-11 | A-15 | B |
| Example 55 | L-11 | O-3 | B |
| Example 56 | L-11 | O-5 | B |
| Example 57 | L-12 | A-1 | B |
| Example 58 | L-12 | A-10 | B |
| Example 59 | L-12 | O-3 | B |
| Example 60 | L-12 | O-3 | B |
| Example 61 | L-12 | O-5 | B |
| Comparative Example 10 | L-6 | B-6 | D |
| Comparative Example 11 | L-7 | B-6 | D |
| Comparative Example 12 | L-8 | B-6 | D |
| Comparative Example 13 | L-9 | B-6 | D |
| Comparative Example 14 | L-10 | B-6 | D |
| Comparative Example 15 | L-11 | B-6 | D |
| Comparative Example 16 | L-12 | B-6 | D |

In Table 8 above, the structures of compound A-1 and the like are as shown in Example 1 and the like, and the structures of the polymerizable liquid crystal compounds and the compounds O-3 and O-5 are as shown below.

Polymerizable liquid crystal compound L-6

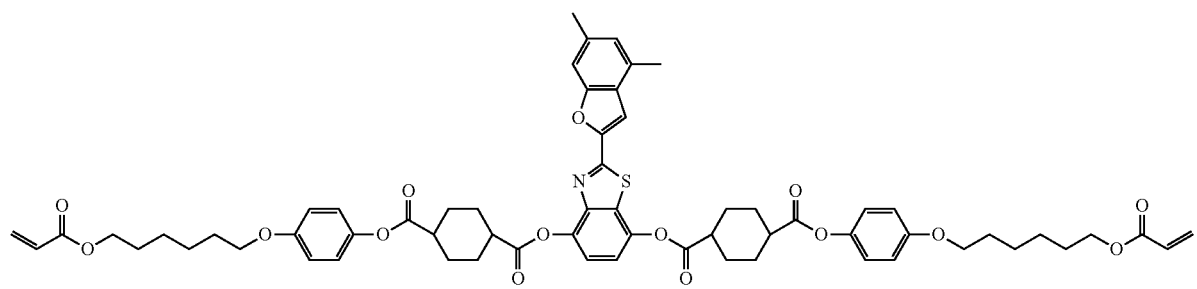

Polymerizable liquid crystal compound L-7

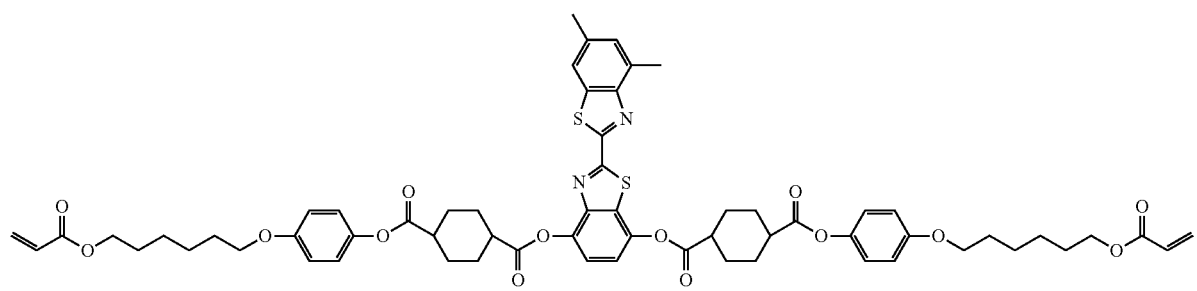

-continued
Polymerizable liquid crystal compound L-8
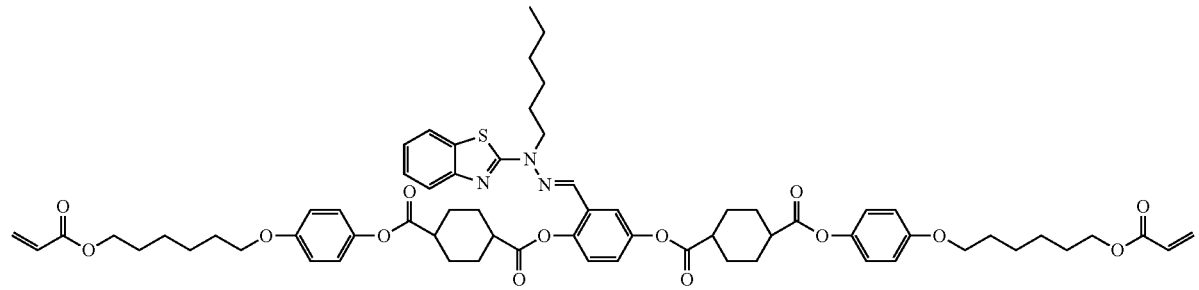
Polymerizable liquid crystal compound L-9
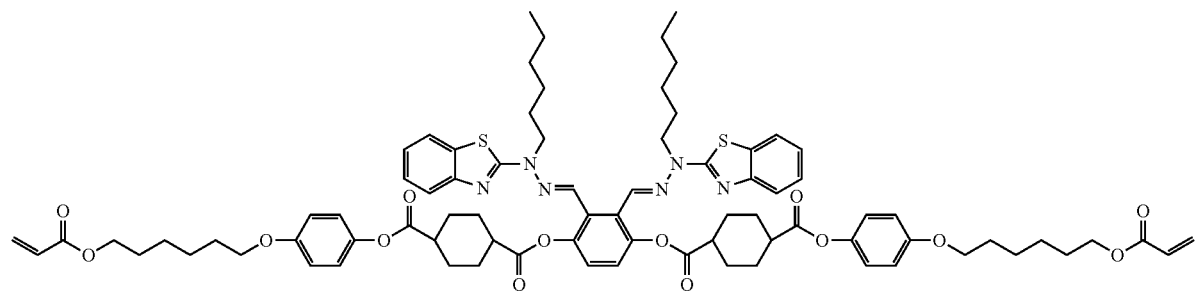
Polymerizable liquid crystal compound L-10
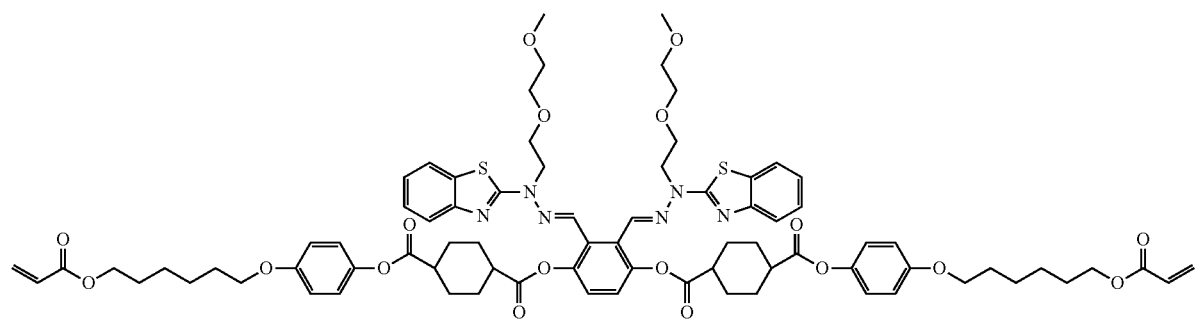
Polymerizable liquid crystal compound L-11
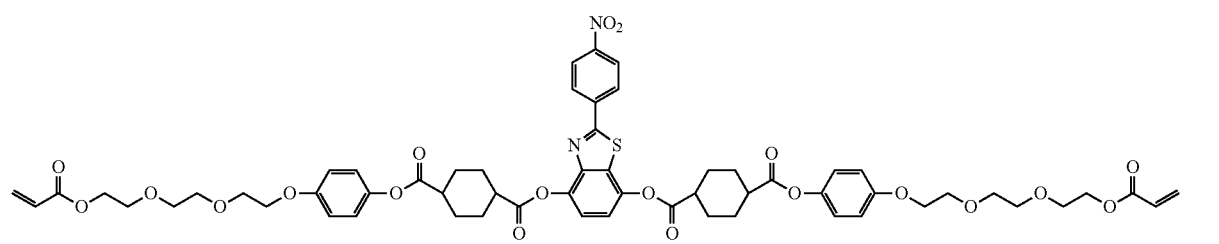
Polymerizable liquid crystal compound L-12
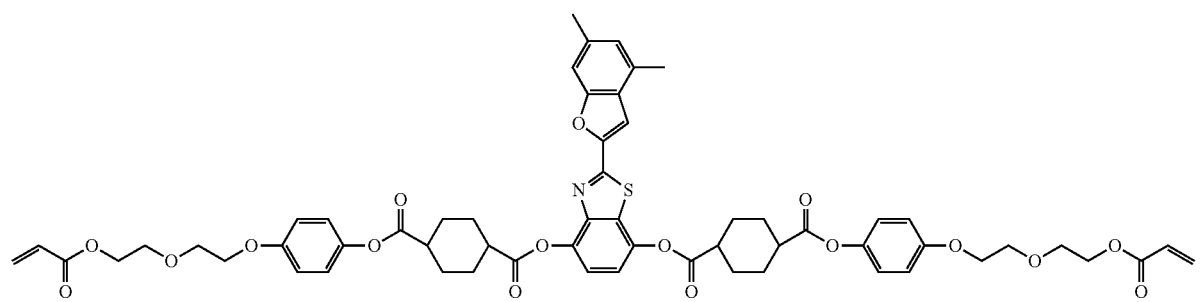

-continued

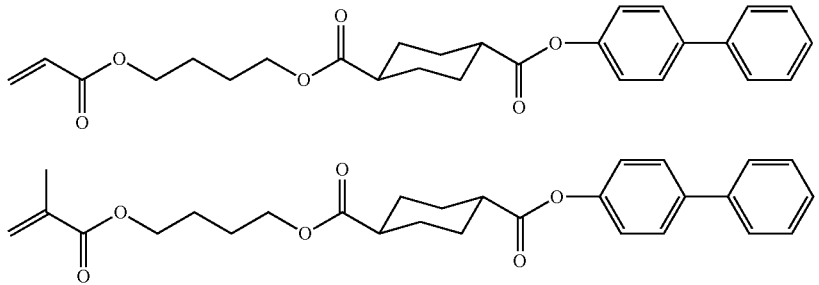

Compound O-3

Compound O-5

EXPLANATION OF REFERENCES

10: optical film
12: optically anisotropic layer
14: alignment film
16: support
18: hard coat layer

What is claimed is:
1. A compound represented by Formula (I),

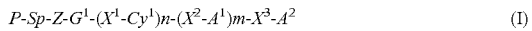  (I)

in Formula (I),

Sp represents a single bond, a linear alkylene group having 1 to 12 carbon atoms, a branched alkylene group having 3 to 12 carbon atoms, or a divalent linking group obtained by substituting one or more of —$CH_2$—'s constituting the linear or branched alkylene group with —O—, —S—, —NH—, —N(Q)-, —CO—, —COO—, —OCO—, —CO—NH—, or —NH—CO—, and Q represents a substituent, Z represents a single bond, —O—, —S—, —NH—, —N(Q)-, —CO—, —COO—, —OCO—, —CO—NH—, or —NH—CO—, and Q represents a substituent, $X^1$, $X^2$, and $X^3$ each independently represent a single bond, —COO—, —OCO—, —CO—NH—, or —NH—CO—, $G^1$ represents an aromatic ring which may have a substituent or a 1,4-cyclohexylene group which may have a substituent, $Cy^1$ represents a 1,4-cyclohexylene group which may have a substituent, $A^1$ represents an aromatic ring which may have a substituent, $A^2$ represents an aromatic ring which may have a substituent R, or an unsubstituted cyclohexane ring, the substituent R represents a linear alkoxy group having 1 to 11 carbon atoms, a branched alkoxy group having 3 to 11 carbon atoms, a linear alkyl group having 1 to 12 carbon atoms, a branched alkylene group having 3 to 12 carbon atoms, or -Z-Sp-P, and Z and Sp are each the same as described above, provided that in a case where $A^2$ is a 6-membered aromatic ring, $A^2$ has no substituent R at a para position with respect to a bonding position with $X^3$, and in a case where the substituent R is -Z-Sp-P, two Z's, two Sp's, and two P's which are present in the formula may be the same as or different from each other, n represents 0 or 1, m represents an integer of 0 to 2, and n+m represents an integer of 1 to 3, and in a case where m is 2, both of two $X^2$'s and two $A^1$'s which are present in the formula may be the same as or different from each other, P represents a polymerizable group, provided that in a case where $A^2$ is an aromatic ring having -Z-Sp-P as the substituent R, one of the two P's which are present in the formula represents a polymerizable group and the other represents a hydrogen atom or a polymerizable group, in a case where $G^1$ is the aromatic ring which may have a substituent, n is 0, and m is 1, $X^3$ represents —COO—, —OCO—, —CO—NH—, or —NH—CO—, and in a case where $G^1$ is the aromatic ring which may have a substituent, n is 1, m is 0, and $A^2$ is the aromatic ring which may have the substituent R, Z represents a single bond, —S—, —NH—, —N(Q)-, —CO—, —COO—, —OCO—, —CO—NH—, or —NH—CO—, and Q represents a substituent, provided that in a case where Z is the single bond, an atom adjacent to $G^1$ among the divalent linking groups constituting Sp is not an oxygen atom.

2. The compound according to claim 1, wherein $A^1$ in Formula (1) represents an unsubstituted aromatic ring.

3. The compound according to claim 1, wherein $A^1$ in Formula (1) represents an aromatic ring having a substituent, and the substituent is an alkyl group, an alkoxy group or a halogen atom.

4. The compound according to claim 1, wherein a total of n and m in Formula (1) is 1.

5. The compound according to claim 1, wherein Sp in Formula (1) is a linear alkylene group having 1 to 3 carbon atoms or a branched alkylene group having 3 carbon atoms.

6. The compound according to claim 1, wherein $A^2$ in Formula (1) is the aromatic ring which may have the substituent R.

7. The compound according to claim 1, wherein $A^2$ in Formula (1) is a 6-membered aromatic ring having the substituent R at an ortho position or meta position with respect to a bonding position with $X^3$.

8. The compound according to claim 1, wherein the substituent R is -Z-Sp-P.

9. The compound according to claim 1, wherein the substituent R is -Z-Sp-P, one of the two P's in the formula represents a polymerizable group, and another one represents a hydrogen atom.

10. The compound according to claim 1, wherein $A^2$ in Formula (1) is an unsubstituted 6-membered aromatic ring.

11. The compound according to claim 1,
wherein $A^2$ in Formula (1) is a benzene ring which may have the substituent R.

12. The compound according to claim 1,
wherein m in Formula (1) is 0.

13. The compound according to claim 1,
wherein n in Formula (1) is 1.

14. The compound according to claim 1,
wherein n in Formula (1) is 0.

15. The compound according to claim 1,
wherein P in Formula (1) is a polymerizable group represented by any of Formulae (P-1) to (P-9),

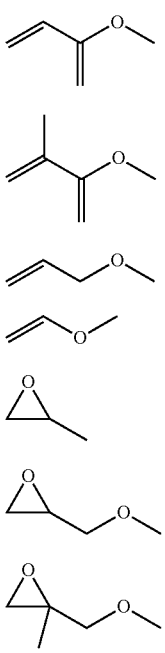

(P-1)
(P-2)
(P-3)
(P-4)
(P-5)
(P-6)
(P-7)

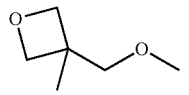

(P-8)

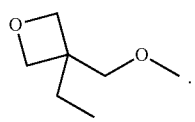

(P-9)

16. The compound according to claim 1,
wherein $G^1$ in Formula (1) is a 1,4-cyclohexylene group which may have a substituent.

17. The compound according to claim 1,
wherein $G^1$ in Formula (1) is the aromatic ring which may have a substituent.

18. A polymerizable composition comprising the compound according to claim 1.

19. The polymerizable composition according to claim 18, comprising a polymerizable liquid crystal compound different from the compound.

20. The polymerizable composition according to claim 19,
wherein the compound and the polymerizable liquid crystal compound have polymerizable groups that are different from each other.

21. The polymerizable composition according to claim 18, comprising a polymerization initiator.

22. A cured product obtained by curing the polymerizable composition according to claim 18.

23. An optical film comprising the cured product according to claim 22.

24. A polarizing plate comprising:
the optical film according to claim 23; and
a polarizer.

25. An image display device comprising the optical film according to claim 23.

* * * * *